(12) United States Patent
Crnko et al.

(10) Patent No.: US 7,291,203 B2
(45) Date of Patent: Nov. 6, 2007

(54) NEGATIVE TEMPERATURE PROFILING USING MICROWAVE GC APPARATUS

(75) Inventors: John S. Crnko, Spring, TX (US); Scott K. Warren, Houston, TX (US)

(73) Assignee: Petroleum Ana Ryzes Company LP, Houston, TX (US)

( * ) Notice: Subject to any disclaimer, the term of this patent is extended or adjusted under 35 U.S.C. 154(b) by 183 days.

(21) Appl. No.: 10/798,233

(22) Filed: Mar. 10, 2004

(65) Prior Publication Data
US 2005/0199121 A1  Sep. 15, 2005

(51) Int. Cl.
*B01D 53/02* (2006.01)
(52) U.S. Cl. ............................. 95/87; 96/101; 73/23.39
(58) Field of Classification Search .................... 95/87; 96/101; 73/23.35, 23.39
See application file for complete search history.

(56) References Cited

U.S. PATENT DOCUMENTS 5,808,178 A * 9/1998 Rounbehler et al. ........ 73/23.39
5,939,614 A * 8/1999 Walters et al. ............. 73/23.39

* cited by examiner

*Primary Examiner*—Robert Hopkins
(74) *Attorney, Agent, or Firm*—Robert W Strozier

(57) ABSTRACT

A method is disclosed for performing GC separations using a separation protocol including at least one negative temperature ramp, where the negative temperature ramp is controlled either by the introduction of a gaseous coolant at a controlled and adjustable rate or by the introduction of the coolant along with the application of microwave radiation to a column capable of absorbing microwave radiation, where the rate of coolant introduction or the rate of coolant introduction and radiation introduction is sufficient to achieve a desired rate of cooling.

9 Claims, 37 Drawing Sheets

*Fig. 22*
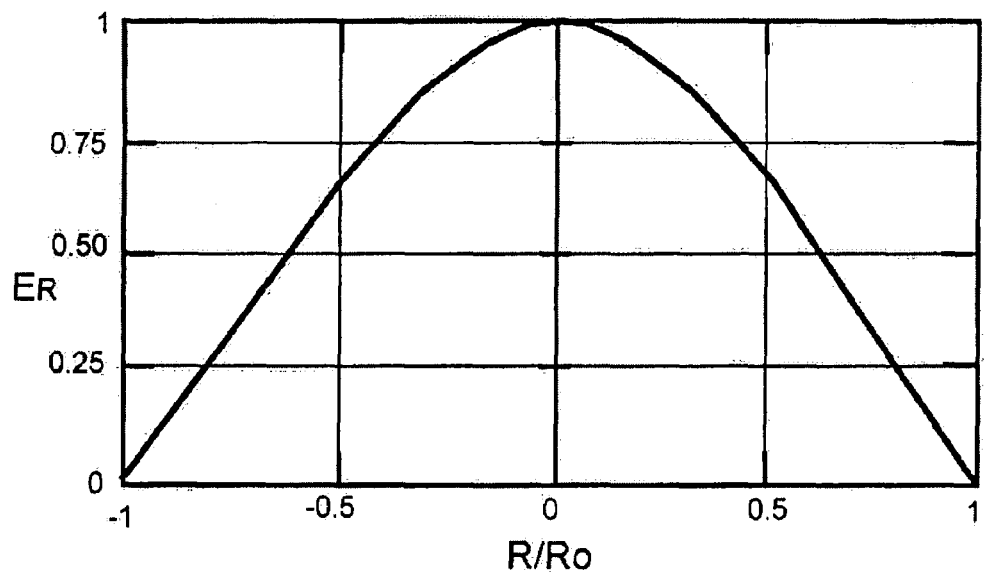
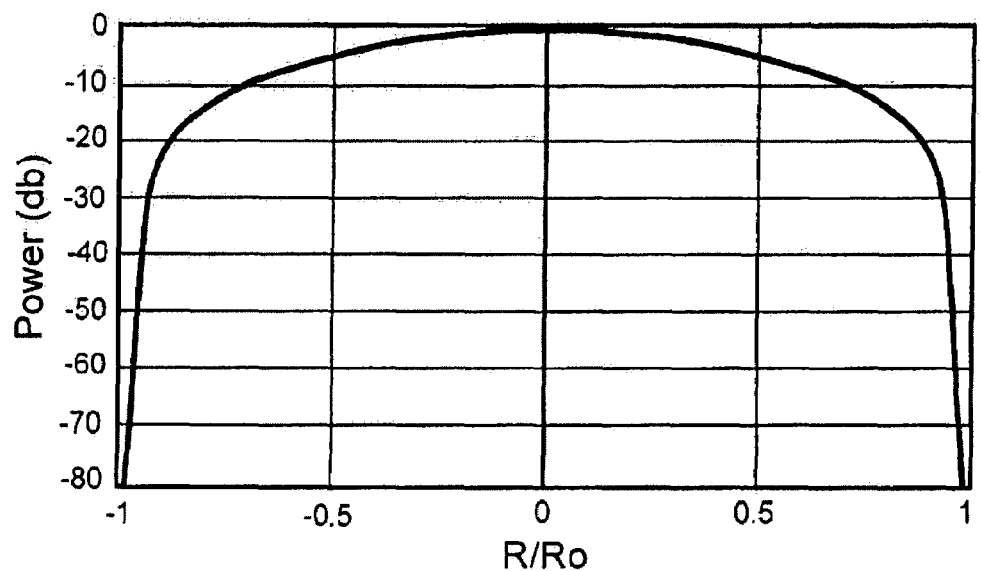
*Fig. 23*

Linear Column Temperature Profile

Periodic Column Temperature Profile

NEGATIVE TEMPERATURE PROFILING USING MICROWAVE GC APPARATUS

BACKGROUND OF THE INVENTION

1. Field of the Invention

The present invention relates to a method for performing negative temperature profiling using a microwave heated gas chromatography instrument.

More particularly, the present invention relates to a method for performing negative temperature profiling using a microwave heated gas chromatography instrument, where the method includes the steps of supplying a gaseous coolant to an interior of a microwave oven including a gas chromatography column having a microwave sensitive coating, where the coolant is supplied at a rate sufficient to cool the column at a desired rate. The method can also include supplying a gaseous coolant to an interior of the microwave oven and irradiating the column with microwave energy so that the combined coolant and irradiation cools the column at a desired rate.

2. Description of the Related Art

Gas and liquid chromatography are physical methods for the separation, identification, and quantification of chemical compounds. These methods are used extensively for applications that include the measurement of product purity in analytical chemistry, the determination of environmental contamination, the characterization of natural substances, and the development of pharmaceuticals.

The fundamental methods used in gas and liquid chromatographs to separate chemical constituents are similar. A sample mixture is injected into a flowing neutral carrier stream and the combination then flows through a tube or chromatographic column. The inner surface of the column is coated or packed with a material called the stationary phase. As the sample mixture and carrier stream flow through the column, the components within the mixture are retained by the stationary phase to a greater or lesser degree depending on the relative volatility (in the case of gas chromatography) or the relative solubility (in the case of liquid chromatography) of the individual components and on their respective affinities for the stationary phase. When the individual mixture components are released into the carrier stream by the stationary phase, they are swept towards the column outlet where they are detected and measured with a detector. Different chemical compounds are retained for different times by the stationary phase. By measuring the retention times, the specific compounds in the mixture can be identified. The relative concentration of the compounds is determined by comparing the peak amplitudes measured with the detector for each compound. The primary difference between gas and liquid chromatography is the mode of separation. In gas chromatography, the sample is volatilized and propelled down the analytical column by a moving stream of gas. In liquid chromatography, the sample is dissolved and propelled down the analytical column in a moving stream of liquid. Another difference between gas and liquid chromatography is that the columns used in liquid chromatography are generally filled or packed with the stationary phase, while those used in gas chromatography can also have the stationary phase coated or bonded to the interior wall, instead.

GC and LC measurements are facilitated by the application of heat to the chromatographic column to change its temperature. The use of a heated column oven in gas chromatographic systems greatly increases the number of compounds that can be analyzed and speeds up the time required for each analysis by increasing the volatility of higher molecular weight compounds. Heating an LC column affects the relative solubility of the mixture's components in the two phases and can enhance the separation as well as improve the repeatability of the elution times of the component chemicals.

Many methods have been described for heating chromatographic columns. The simplest and most commonly used method utilizes resistive heating elements to heat air which is in turn circulated through an insulated oven in which the column is placed. For example, U.S. Pat. No. 3,527,567 to Philyaw et al. describes a GC oven heated with resistive elements.

The resistive element heating method has several limitations. To achieve even heating of the column, a large volume of air is rapidly circulated around the chromatographic column. In addition to heating the column, the air heats the oven itself. Because the thermal mass of the oven is much larger than that of the column, the rate at which the column can be heated is commensurately reduced. A related problem is cooling time. After heating the oven to a high temperature during an analysis, it takes significantly longer to cool the oven plus the column to their initial temperature so that the next sample may be analyzed than it would to cool the column alone. Together, these limitations reduce the throughput of the chromatograph.

Attempts to localize the resistive heat element onto the column itself so as to reduce or eliminate peripheral heating of the 'oven' are described in U.S. Pat. No. 3,169,389 to Green et al., U.S. Pat. No. 3,232,093 to Burow et al., and in U.S. Pat. No. 5,005,399 to Holtzclaw et al. Each of these patents describe methods for directly wrapping or cladding the chromatographic column with a resistive heating element. Methods are also described for positioning the resulting metal clad column adjacent to a cooling source to decrease cooling times. This method of heating can be difficult to implement in practice because of uneven heating of the column due to local hot or cold spots in the resistive heating element surrounding the column. Uneven heating of the column in turn compromises the quality of the analysis.

Yet another limitation of all resistively heated chromatographic devices is that if operated improperly, they can be driven to temperatures higher than the maximum tolerated by a given column resulting in damage to or destruction of the column.

An alternative method for heating chromatographic columns is microwave heating as described in U.S. Pat. No. 4,204,423 to Jordan. Potential advantages of microwave heating are efficiency and selectivity. Suitable objects placed in a microwave oven will be heated when the oven is operated, but the temperature of the oven itself will not change. Microwave heating occurs in materials which absorb the microwave energy and convert it into heat. Current chromatographic columns are generally made of materials that do not absorb microwave energy at an appreciable rate. For example, most GC capillary columns are made of polyimide and fused silica. Consequently, such columns will not heat at an appreciable rate when placed in a microwave oven. The apparatus taught by Jordan is not practicable with these columns.

Jordan teaches that any column material can be placed in a microwave oven except for conductive materials such as metals which will reflect the electromagnetic energy (by shorting out the electric field) in the microwave oven, thus rendering it inoperable. Indeed any such non-metal material can be placed in a microwave oven, but they will not necessarily be heated by the oven.

U.S. Pat. No. 3,023,835 to Brashear describes an apparatus for heating packed chromatographic columns by exposing them to radio frequency (RF) radiation. Brashear describes heating chromatographic columns via dielectric heating or via inductive heating (i.e., magnetic heating). In the case of dielectric heating, Brashear specifies that the column and the packing filler are constructed of electrically insulating materials. Most insulating materials, including those used to make chromatographic columns, do not absorb electromagnetic energy at a high enough rate to make dielectric heating as taught by Brashear practical. In the case of inductive heating, Brashear specifies that: (1) the column is constructed of a metal containing some magnetic components to enable inductive heating to occur; (2) the filler contains a metal powder to promote heat conduction from the column into the filler; and (3) the metal powder may also be magnetic to promote local inductive heating. In practice, inductive heating of the filler would not occur inside the metal column because it would be shielded from the electromagnetic field by the metal column in which it is sheathed. Moreover, metal-filled packing material inside columns is not generally a good scheme. The sample material passing down the column can be exposed to the metal. If the metal is not chemically inert, then some components of the sample can react with the metal thus distorting the resulting chromatogram.

Neither of the packed column constructions described by Brashear would be of practical usage in a microwave heating apparatus as taught by Jordan where the whole of the column is placed inside a cavity and exposed to high intensity electromagnetic radiation. The insulating low-loss column would not heat rapidly enough to be of practical use. The metal column would short out the electric field to such a significant extent that the microwave oven would not function properly and the column, if heated at all, would not be heated evenly.

Further background information can be found in U.S. Pat. Nos. 6,029,498; 6,093,921; 6,157,015; 6,316,759; and 6,514,316 and U.S. Pat. Appln. Pub. No. 20010000403, incorporated herein by reference.

Thus, there is a need in the art for a method to affect separation of components in a sample by including at least one so called negative temperature ramp in the GC profile by supplying either a gaseous coolant to a microwave GC oven including a column capable of being heated with microwave radiation or supplying to the microwave GC a combination of the coolant and microwave radiation so that a desired cooling rate can be achieved.

SUMMARY OF THE INVENTION

The present invention provides a method for improving separation efficiencies including at least one negative temperature ramp in a gas chromatographic separation protocol by supplying a gaseous coolant to a microwave GC oven including a column capable of being heated with microwave radiation or supplying to the microwave GC a combination of the coolant and microwave radiation so that a desired cooling rate can be achieved.

The present invention also provides a method for improving separation efficiencies including at least one negative temperature ramp in a gas chromatographic separation protocol by supplying a gaseous coolant to a microwave GC oven including a column capable of being heated with microwave radiation or supplying to the microwave GC a combination of the coolant and microwave radiation so that a desired cooling rate can be achieved and at least one positive temperature ramp so that the column is heated at a desired heating rate.

The present invention also provides a method for improving separation efficiencies including at least one negative temperature ramp or step in a gas chromatographic separation protocol, where the step is accomplished by supplying a gaseous coolant to a microwave GC oven including a column capable of being heated with microwave radiation or supplying to the microwave GC a combination of the coolant and microwave radiation so that a desired cooling rate can be achieved, at least one positive temperature ramp so that the column is heated at a desired heating rate, and at least one hold step separating any two temperature ramps, negative or positive, where the hold step is for a time sufficient to achieve a desired separation result.

The present invention also provides an apparatus improving separation efficiencies including a microwave oven and a supply of sub-ambient temperature coolant so that controlled negative temperature ramps can be produced in a desired GC separation protocol.

DESCRIPTION OF THE DRAWINGS

The invention can be better understood with reference to the following detailed description together with the appended illustrative drawings in which like elements are numbered the same:

FIGS. 22 and 23 are graphs showing the radial electric field and resultant microwave power distributions respectively for the $TM_{010}$ mode in a cylindrical resonant cavity.

DETAILED DESCRIPTION OF THE INVENTION

The inventor has found that superior GC separations can be achieved when samples includes closely clustered analytes or groups of analytes by including at least one negative temperature ramp in a GC separation profile. The negative temperature ramp can be anywhere in the profile and preferably is separated from other temperature ramps (positive or negative) by a temperature hold step. Such negative temperature ramps, steps or profiles can be used to allow lower boiling components to travel through the column while maintaining little or no separation of higher boiling components and to increase separation efficiency for components with close boiling points or groups of components with close boiling points.

The present invention broadly relates to a method for improving separation efficiencies including at least one negative temperature ramp in a gas chromatographic separation protocol by supplying a gaseous coolant to a microwave GC oven including a column capable of being heated with microwave radiation or supplying to the microwave GC a combination of the coolant and microwave radiation so that a desired cooling rate can be achieved. The method for improving separation efficiencies including at least one negative temperature ramp in a gas chromatographic separation protocol by supplying a gaseous coolant to a microwave GC oven including a column capable of being heated with microwave radiation or supplying to the microwave GC a combination of the coolant and microwave radiation so that a desired cooling rate can be achieved and at least one positive temperature ramp so that the column is heated at a desired heating rate. The method for improving separation efficiencies including at least one negative temperature ramp or step in a gas chromatographic separation protocol, where the step is accomplished by supplying a gaseous coolant to a microwave GC oven including a column capable of being heated with microwave radiation or supplying to the microwave GC a combination of the coolant and microwave radiation so that a desired cooling rate can be achieved, at least one positive temperature ramp so that the column is heated at a desired heating rate, and at least one hold step separating any two temperature ramps, negative or positive, where the hold step is for a time sufficient to achieve a desired separation result.

The present invention broadly relates to an apparatus improving separation efficiencies including a microwave oven and a supply of sub-ambient temperature coolant so that controlled negative temperature ramps can be produced in a desired GC separation protocol.

Negative Temperature Protocols

Figure 1:
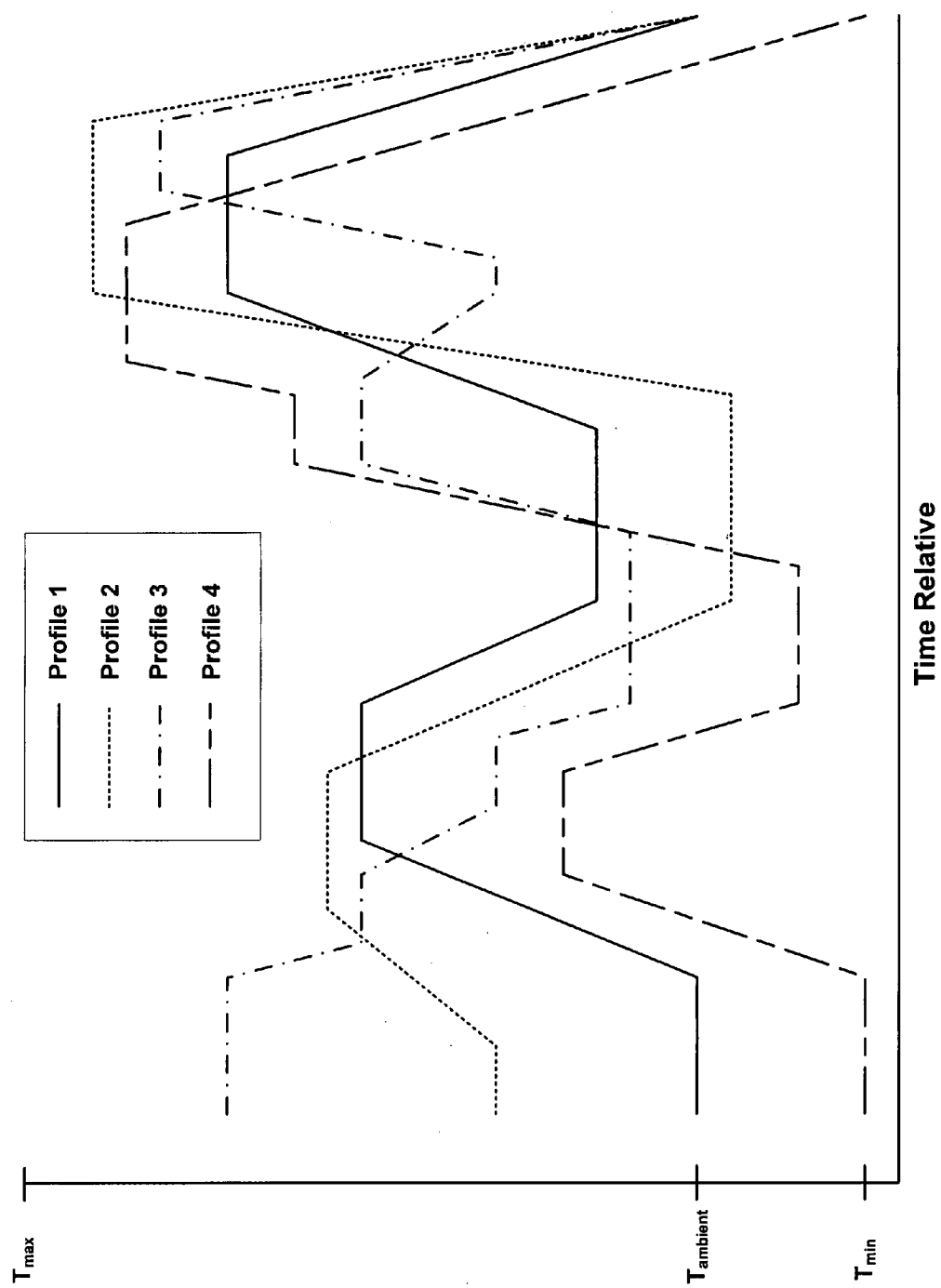
FIG. 1 depicts a set of GC separation profiles or protocols including at least one negative temperature ramp and at least one hold between ramps.

Referring now to FIG. 1, a set of four GC separation profiles are shown. Each profile, profiles 1–4, includes at least one negative temperature ramp, where the rate of decrease or a slope of the ramp is controlled by either a temperature and a flow rate of a gaseous coolant or by a combination of the temperature and the flow rate of the gaseous coolant with radiative microwave heating so that any realistic cooling rate can be achieved. Generally, the heating and/or cooling rates are between about 1° C./minutes and about 300° C./minute, preferably, between about 1° C./minutes and about 200° C./minute, particularly, between about 1° C./minutes and about 180° C./minute, and especially between about 1° C./minutes and about 150° C./minute; although, higher or lower rates can be accommodated, limited only by mechanical and electrical limitations. A maximum temperature $T_{max}$ is generally about 10° C. below a break down temperature of a most thermally unstable component of the column, but is generally around 300° C. Of course, $T_{max}$ will vary with column construction, composition or the like and may be higher or lower depending of column characteristics. A minimum temperature $T_{min}$ is generally a temperature at which the column material can no longer function as a separation medium and may have a practical limit of absolute zero, but is generally, near liquid nitrogen temperatures. Obviously, for colder applications, the limit can be near liquid helium temperatures. Hold times can be from about 0 minutes to about 30 minutes, preferably, from about 0.1 minutes to about 20 minutes, and particularly, from about 0.5 minutes to about 10 minutes; although, longer holds can be easily accommodated.

Microwave Heated GC Columns

Potential advantages to be derived from heating chromatographic columns in microwave ovens are heating selectivity, efficiency, and speed. Suitable objects placed in a microwave oven will be heated when the oven is operated, but the oven itself will not be heated. In the descriptions of microwave ovens for chromatographic column described herein, the term "microwave" is used broadly to refer to electromagnetic radiation in the frequency range from 10 MHz to 100 GHz.

Microwave heating can occur in a material if its dielectric or magnetic loss factor is significantly greater than zero. When such a material is exposed to a high frequency electric or magnetic field, the material will absorb power from the field and convert this power into heat. The average power per unit volume absorbed by a given material is described by the following equation:

$$P_{av} = \omega \in_0 \in''_{\mathit{eff}} E_{rms}^2 + \omega \mu_0 \mu''_{\mathit{eff}} H_{rms}^2 \quad (1)$$

where (a) $\omega$ is the angular frequency of the electromagnetic radiation, (b) $\in_0$ is the permittivity of free space, (c) $\in''_{\mathit{eff}}$ is the dielectric loss factor, (d) $E_{rms}$ is the rms electric field strength, (e) $\mu_0$ is the permeability of free space, (f) $\mu''_{\mathit{eff}}$ is the magnetic loss factor, and (g) $H_{rms}$ is the rms magnetic field strength.

The dielectric loss factor $\in''_{\mathit{eff}}$ is a parameter which describes losses associated with the movement of electrical charge in a material; i.e. conduction losses. There are two distinct sources of conduction losses. The first is associated with very short range electrical currents called displacement currents that result from the rotation of permanent dipoles within a material in response to an electric field. The second source of conduction loss is associated with long range charge transport within a dielectric material that is somewhat conductive. For the purposes of this description, the dielectric loss factor includes all electrical losses associated with the conduction of electrical charge through a material in response to an electric field.

The material will heat at a rate in ° C./sec given by:

$$\text{Heating Rate} = P_{av}/\rho c_p \quad (2)$$

where $\rho$ is the density of the material, and $c_p$ is the specific heat of the material, As shown by equations (1) and (2), the rate at which the temperature of a material will heat when exposed to microwave radiation is proportional to the dielectric and magnetic loss factors of the material.

Table 1 summarizes the properties of some materials at 25° C. and at a frequency of 2.5 GHz, which is a frequency commonly used for microwave heating.

TABLE 1

| Material | $\in''_{\mathit{eff}}$ | $\mu''_{\mathit{eff}}$ | $\rho$ (g/cc) | $c_p$ (J/g ° C.) |
|---|---|---|---|---|
| Silica Glass | 0.0004 | 0.0 | 2.2 | 0.75 |
| Polyimide | <0.008 | 0.0 | 1.4 | 1.674 |
| Air | <0.0001 | 0.0 | — | 1.0 |
| polytetra-fluoroethylene | <0.0003 | 0.0 | 2.15 | — |
| Silicone Rubber | 0.05 | 0.0 | 1.15 | 2.0 |

TABLE 1-continued

| Material | $\epsilon''_{eff}$ | $\mu''_{eff}$ | ρ (g/cc) | $c_p$ (J/g ° C.) |
|---|---|---|---|---|
| Fresh Water | 9.5 | 0.0 | 1.0 | 4.18 |
| Alumina | <0.01 | 0.0 | 3.9 | 0.92 |
| Ferrite (Crowley 20 from H. L. Crowley) | 0.54 | 2.5 | — | — |
| Iron-Filled Epoxy (Eccosorb CRS 1 from Emerson & Cuming) | 1.9 | 2.55 | 4.55 | 2.92 |

Figure 2:
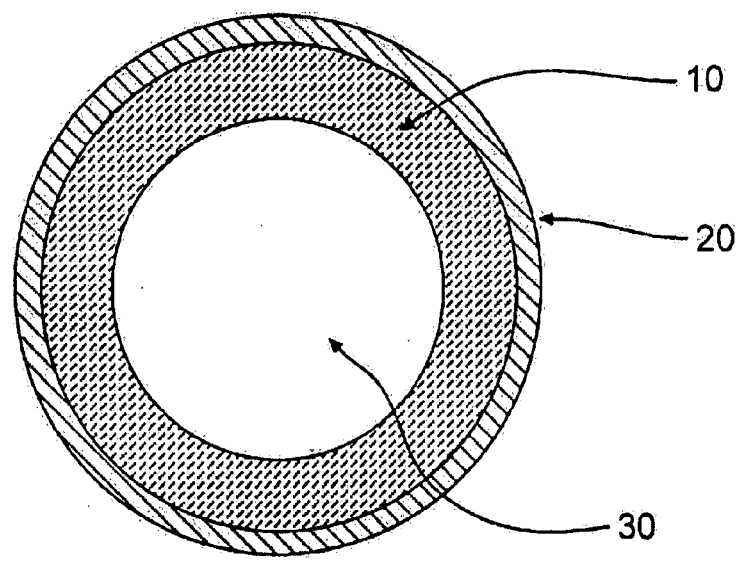
FIG. 2 shows the cross section of a typical chromatograph column.

FIG. 2 shows the cross section of the most common type of GC capillary column. It is a tube fabricated of fused silica (glass) 10 coated externally with polyimide 20 for added strength. The fused silica has an ID ranging from 0.1 to 0.53 mm in diameter. The wall thickness of the fused silica is 0.1 to 0.2 mm. The wall thickness of the polyimide is typically about 5 μm. The interior 30 of tube 10 consists of a thin stationary phase of typically 1 μm or less that is bonded to the inside of the fused silica (not shown in FIG. 2) and the remainder is gas most of which is the inert carrier gas. The total length of the capillary column varies typically from 15 to 60 m.

An LC column generally consists of a metal or plastic tube packed with a porous support material such as crushed silica to which is bound a stationary phase. Tube dimensions generally range from an internal diameter of 1 mm to 10 mm and a length of 5 cm to 30 cm. Taking FIG. 2 as an LC column, element 10 is the tube and element 30 is the packed support material and stationary phase. The external coating 20 is not used with a LC column.

The major non-metal components of these columns are crushed or fused silica glass, polyimide, and plastic. As indicated in Table 1, these materials have very low dielectric and magnetic loss factors. Most plastics and glasses have loss factors less than that shown for polyimide. If placed in a microwave heating apparatus and exposed to an electromagnetic field of equal intensity, these materials will absorb power at a rate about 1000 times slower than will water. It is not feasible to increase the electric field intensity enough to compensate for the low loss factors owing to dielectric breakdown problems. Consequently, it is not practical to heat standard chromatograph columns in microwave heating devices. To correct this limitation and to make the attractive aspects of microwave heating possible in chromatographic applications, appropriate high loss factor material(s) must be added to the columns or placed adjacent to them so that this material(s) will heat up when exposed to microwave radiation and then heat the column via heat conduction or convection.

Many types of high loss factor materials could be used to increase the heating rate of a chromatographic column in a microwave heating apparatus. High loss factor in this case means any material with a high enough loss factor to enable a chromatographic column to be heated at a rate of at least a few degrees Centigrade per minute and preferably at a rate of 100° C. per minute or more. Such a material would likely have a loss factor of at least 0.05. However, microwave absorbing materials having loss factors less than 0.05 can be used if they are heated in microwave heating apparatuses with very high quality factors. A microwave heating apparatus with a high quality factor will not itself absorb much microwave power. In general, the total microwave losses in a microwave absorbing material used to heat a column or column assembly in a microwave heating apparatus should be at least as great as the total losses that occur elsewhere in the microwave heating apparatus, such that the microwave heating apparatus is at least 50% efficient in delivering available microwave power in the microwave heating apparatus to the microwave absorbing material.

Microwave absorbing materials with high dielectric or magnetic loss factors could be used. Examples of materials with high dielectric loss factors include carbon and some forms of titanium oxide. Examples of materials with high magnetic loss factors include ferrites, iron, nickel, and cobalt. Carbon, iron, nickel, and cobalt are electrically conductive and as such not good microwave absorbing material candidates by themselves in a microwave heating application because they will tend to short out or distort the electromagnetic field in a microwave heating apparatus. However, when used as an additive in an electrically insulating material such as epoxy, rubber, or plastic, the resulting matrix typically has a much lower conductivity and so does not disable a microwave heating apparatus, yet retains a significant portion of the microwave absorbing characteristics of the additive. The iron-filled epoxy in Table 1 is such a mixture. Carbon-loaded materials are another example of such mixtures. In carbon-loaded mixtures, moderately conductive carbon is added to a dielectric material in precise quantities to give the resulting mixture a desired volume resistivity. Such mixtures are the basis for carbon-film resistors.

The term "microwave absorbing material" refers broadly to any material with a high enough dielectric or magnetic loss factor that can be heated in a microwave heating apparatus at a sufficiently fast rate and to a high enough temperature to be of practical value in gas or liquid chromatographic applications. This typically requires a loss factor of at least 0.05. "Microwave absorbing material" also includes materials such as iron or carbon that are electrically conductive and therefore are not good absorbers by themselves, but are good microwave absorbers when added in powdered form as fillers to nonconductive materials, such as epoxies or plastics. In such a mixture, it is the filler material that absorbs the microwave energy and is heated as a result. For such material matrices, the term "microwave absorbing material" refers to the filler material that actually absorbs the microwave energy, rather than to the matrix as a whole. It should be clear to one of ordinary skill in the art that "microwave absorbing material" refers to any material or combination of materials that can be used to significantly enhance microwave heating of a chromatographic column.

The term "microwave absorbing matrix" will be used to refer to mixtures of microwave absorbing materials and insulating materials. These material mixtures will often have specific advantages in chromatographic applications in that they overcome common physical limitations of most microwave absorbing materials by themselves. Gas chromatographic columns must typically be flexible, chemically inert, and capable of withstanding frequent temperature cycling. Similarly, liquid chromatographic columns must typically be chemically inert, and capable of withstanding high pressure and frequent temperature cycling. Few, if any microwave absorbing compounds or elements by themselves meet these requirements. However, when a microwave absorbing material is mixed into an insulating material with suitable physical properties, such as polyimide, the resulting mixture has physical properties similar to those of the insulating material yet absorbs microwave energy because of the microwave absorbing filler. Thus, microwave absorbing matrices can be engineered that combine good physical and microwave absorbing properties. Here again, the resulting material matrix should typically have an overall loss factor of at least 0.05. Preferred embodiments of such microwave absorbing matrices include mixtures of a high grade plastic such as polyimide or polyetherether ketone (PEEK) and an additive such as iron, ferrite, nickel, cobalt, or carbon. In the descriptions of the chromatographic column assemblies herein, the term "microwave" will also be used broadly to cover electromagnetic radiation in the frequency range from 10 MHz to 1000 GHz.

Chromatographic columns can be augmented with a microwave absorbing material in two ways to enhance the effectiveness of microwave heating devices in heating the columns. First, a microwave absorbing material can be added directly to a column resulting in direct conductive heating of the reminder of the column (e.g., a combination of a continuous phase material and the microwave absorbing material). Second, microwave absorbing material can be placed adjacent to (i.e., in thermal contact with, or in close proximity to) a column such that the column is heated indirectly by thermal conduction or convection. There are many arrangements of microwave absorbing material and a column which achieve one or both of these configurations.

Figure 3:
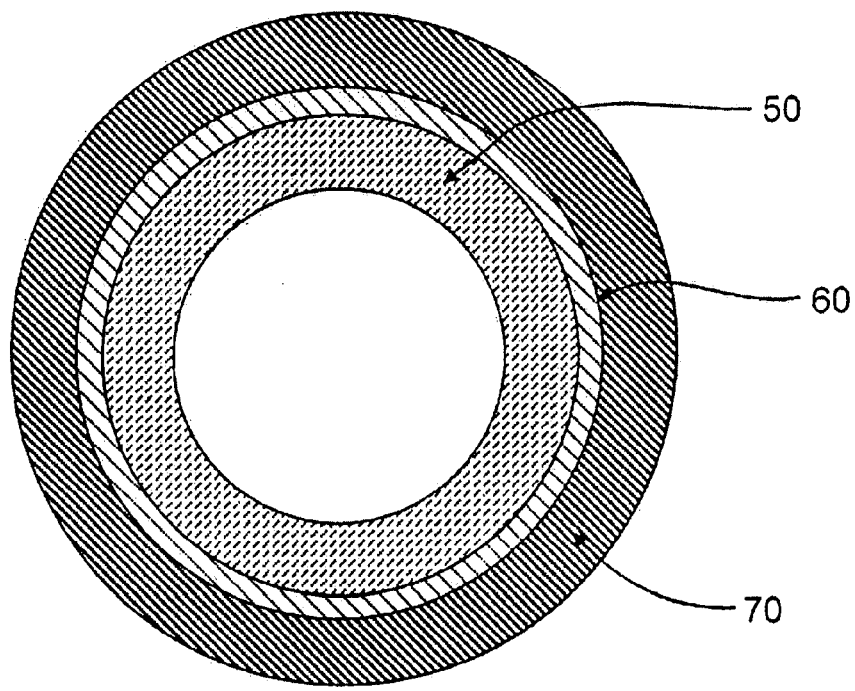
FIGS. 3 and 4 show the cross-sections of a two chromatograph columns with a microwave absorbing material added in accordance with the present invention.

Adding a Microwave Absorbing Material to a Column. FIG. 3 shows the cross section of a chromatographic column where an external layer 70 comprising microwave absorbing material is added to the outside of an existing column. For a fused silica or glass GC capillary column, tube 50 represents a fused silica or glass tube. It is coated with an optional layer of a polymer 60, such as polyimide. The polyimide layer 60 is optional for this modified chromatograph column because the microwave absorbing layer 70 could provide the same function as the polyimide layer in existing columns. For chromatographic columns other than fused silica or glass capillary columns, such as packed GC columns or an LC columns, tube 50 is a glass or plastic tube. Tube 50 could even be metal if the microwave absorbing material 70 shields it sufficiently to prevent the metal from short circuiting the electric field in a microwave heating apparatus. For columns with a glass, plastic, or metal tube 50, the polymer layer 60 would not be present.

Figure 4:
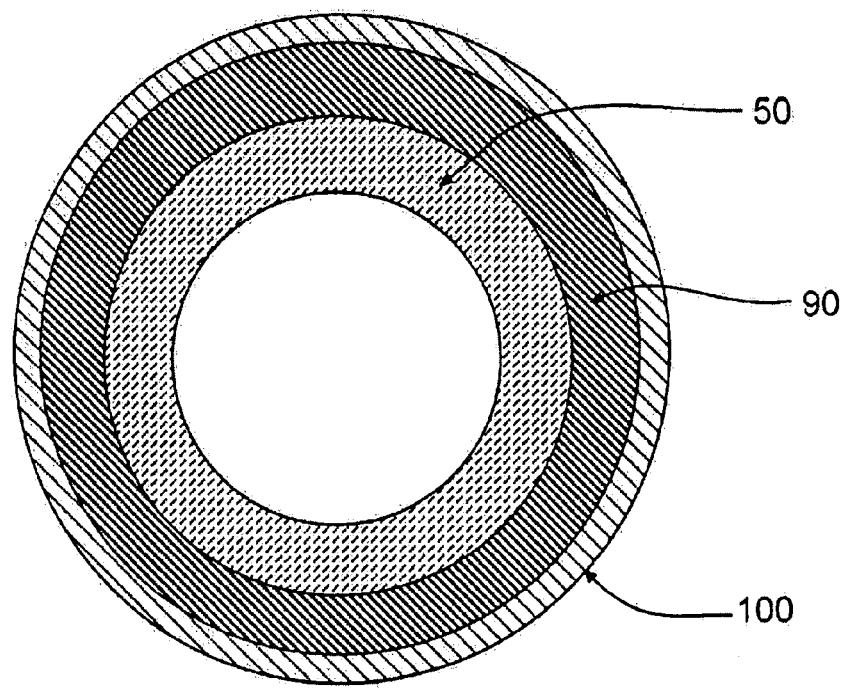

A better configuration is shown in FIG. 4. In this embodiment, a microwave absorbing material layer 90 is added to the existing chromatograph column tube 50. The tube 50 could be fused silica, glass, plastic, or metal. The polymer sheath 100 covers the outside of the microwave absorbing material 90. Together, the tube 50 and sheath 100 physically isolate the microwave absorbing layer 90 from the environment. Sheath 100 could consist of a material such as polyimide or polytetrafluoroethylene, sold under the trademark TEFLON.

Figure 5:
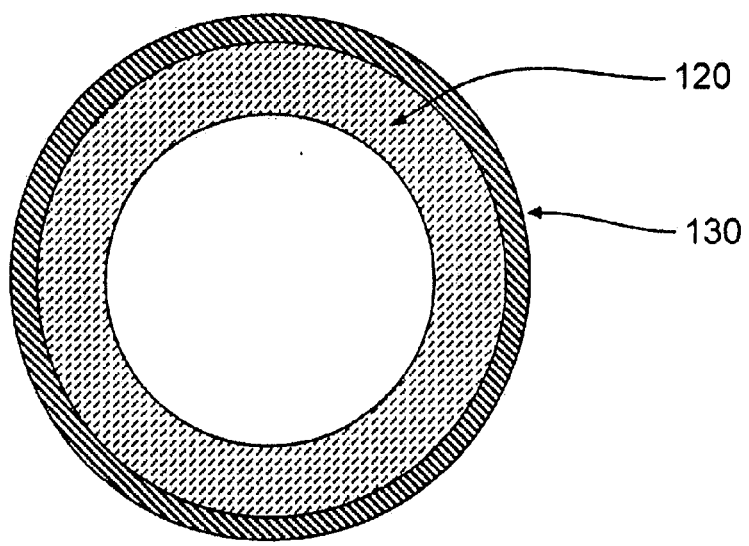
FIG. 5 shows the cross-section of a chromatograph column with a microwave absorbing material mixed into one of the existing column layers accordance with the present invention.

Another manner in which a microwave absorbing material can be added to a chromatographic column is to mix a microwave absorbing material into one of the materials already used in a column so as to make a microwave absorbing matrix. In FIG. 5, column tube 120 is a fused silica, glass, or plastic tube in which a microwave absorbing material has been mixed. The resulting microwave absorbing matrix can be readily heated in a microwave heating apparatus. Where applicable, tube 120 is coated with a thin layer 130 of material such as polyimide to strengthen and environmentally isolate the column.

Alternatively, the microwave absorbing material could be mixed into the outer polymer layer 130 rather than into the tube 120. The electrical effect on the column would be much the same. In effect, this structure is illustrated in FIG. 3 where the microwave absorbing layer 90 consists of a polyimide-microwave absorbing material mixture and the sheath 100 is absent. For example, the polyimide can be impregnated with iron, nickel, ferrite, carbon, or other microwave absorbing materials to form a composite material that can be readily extruded over the column during manufacture.

In another embodiment, an inner layer of fused silica, glass, or plastic is surrounded by an intermediate layer containing a microwave absorbing material. A polymer, such as polyimide, is then applied over the intermediate layer to form a third, outer layer that provides a degree of physical protection, thermal insulation, and added strength for the column assembly.

There are many different physical configurations with which a microwave absorbing material can be added to a chromatographic column so as to make it possible to heat the column in a microwave heating apparatus. The microwave absorbing material can be mixed into one of the column components or it can be bonded to the column as an exterior or interior layer. Some combination of these physical configurations could also be used. It should be clear to one of average skill in the art that the invention lies in the addition of the microwave absorbing material to an existing chromatographic column and not in the manner in which it is added.

Column Assemblies With A Microwave Absorbing Material Adjacent To A Column. A chromatographic column can be heated in a microwave heating apparatus by a microwave absorbing material if the column is located adjacent to the microwave absorbing material such that heat is transferred by the absorbing material to the column via thermal conduction, convection, or radiation. Ideally, the column assembly should keep the temperature difference between the microwave absorbing material and the column to a minimum.

Figure 6:
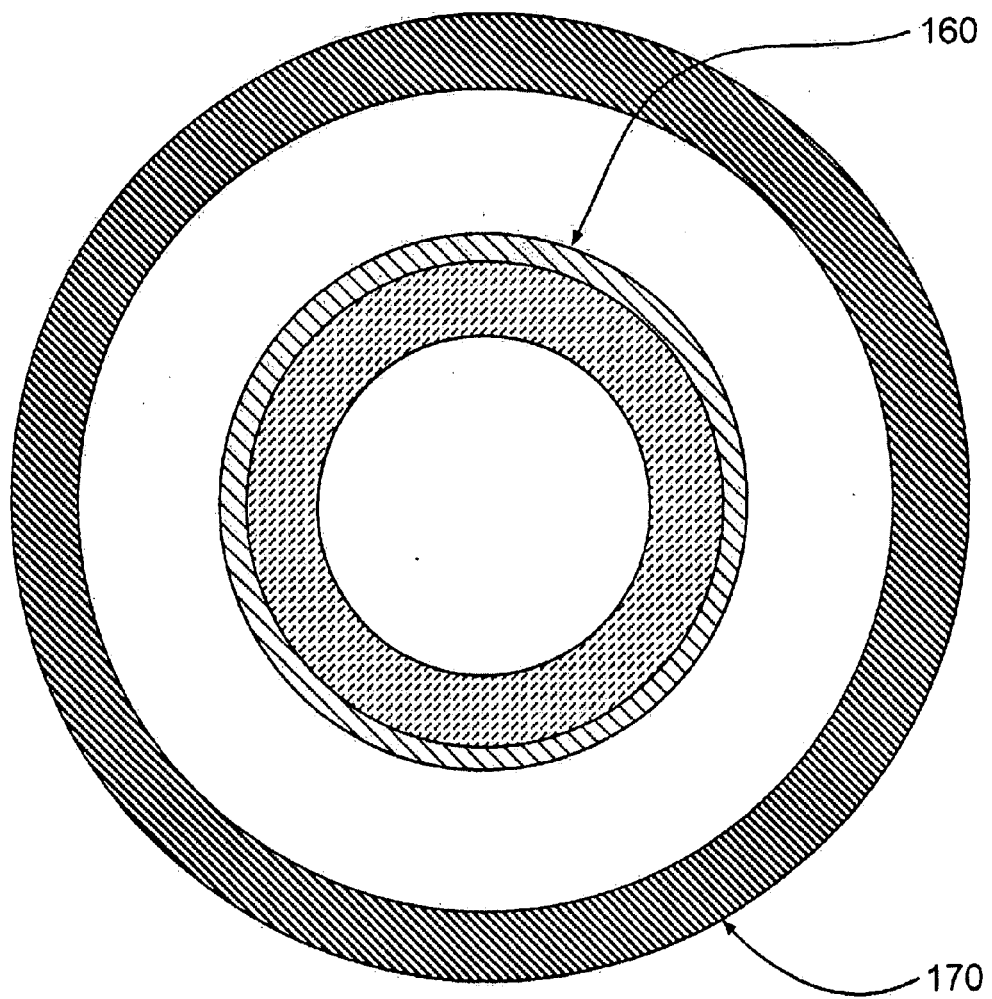
FIG. 6 shows the cross-section of a chromatograph column assembly constructed in accordance with the present invention where an existing column is inserted inside a second tube made at least in part with a microwave absorbing material.

FIG. 6 shows the cross-section of one column assembly built in accordance with the present invention. At least a portion of a standard chromatographic column 160 is inserted into a larger sleeve or tube 170 made of a microwave absorbing material. The inner diameter of microwave absorber tube 170 must be large enough as compared to the outside diameter of column 160 to facilitate threading many tens of meters together. The gap should be small enough to keep the interior of the microwave absorber tube 170 at isothermal conditions over the cross-section.

Figure 7:
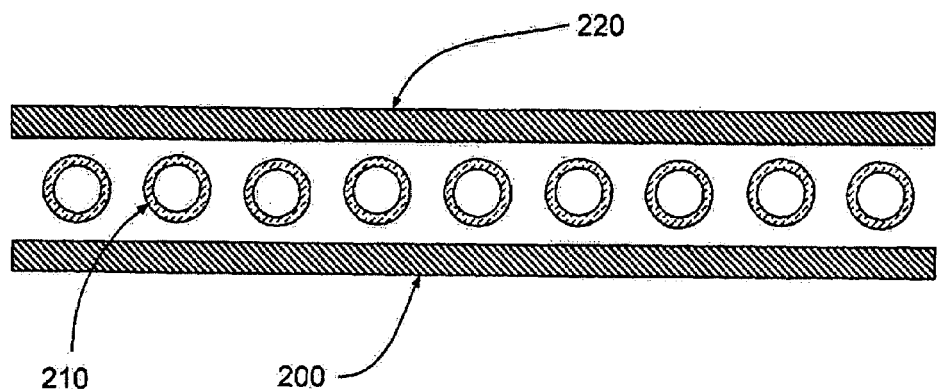
FIGS. 7 and 8 show two different views of a chromatograph column assembly constructed in accordance with the present invention where an existing column is placed adjacent to sheets of microwave absorbing material.
Figure 8:
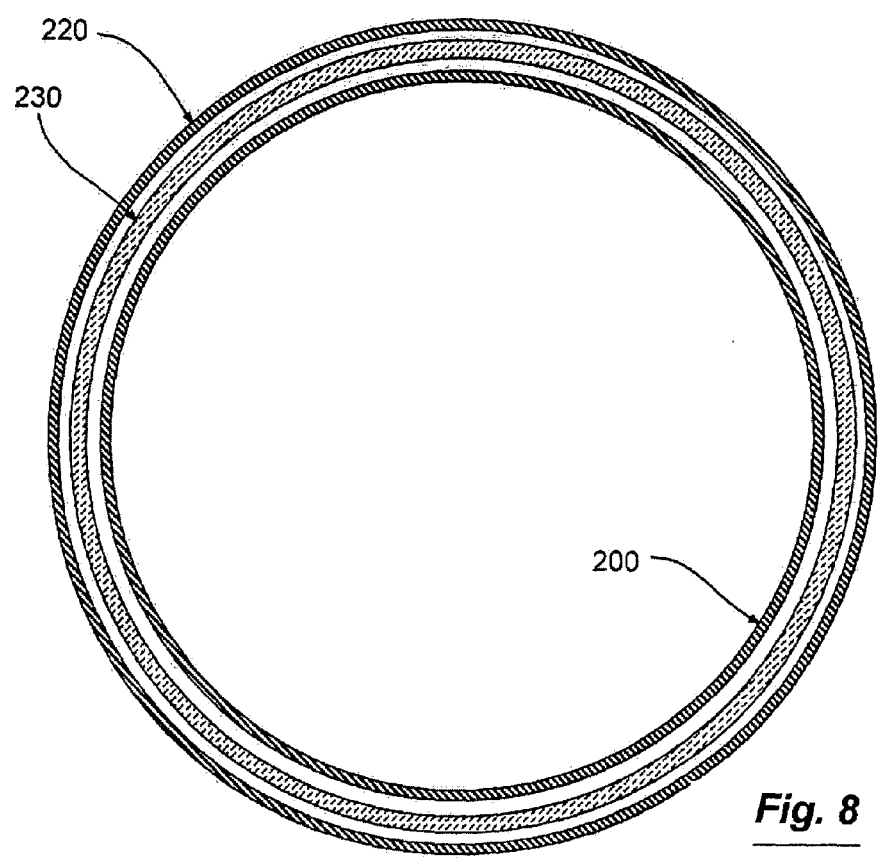

FIGS. 7 and 8 show two views of another column assembly built in accordance with this invention. This assembly is easier to implement than that shown in FIG. 6. Chromatographic columns are often very long and slender— up to 100 meters in length by less than 1 mm in diameter. To make such columns easier to handle, they are usually coiled and held in a spool. An effective column assembly for microwave heating purposes can be constructed by coiling a chromatographic column adjacent to a heating member containing a microwave absorbing material. For example, the column assembly can be constructed by coiling an existing chromatographic column around a core containing a microwave absorbing material. FIG. 7 shows the cross section of such an assembly. FIG. 7 highlights several adjacent column sections 210 sandwiched between two layers 200 and 220 containing a microwave absorbing material. The sandwich can help maintain more stable thermal conditions at different points along the column. FIG. 8 shows a side view of the column assembly. A loop of the column 230 is coiled around a sheet 200 containing a microwave absorbing material. A second microwave absorbing sheet 220 is wrapped outside the column 230. The column 230 and the microwave absorbing sheets 200 and 220 are in effect the concentric cylinders slipped together. If only one microwave absorbing sheet is used instead of two, it could be positioned either inside or outside the column coil. The chromatography column can also be coiled inside a container made of a microwave absorbing material.

It should be understood that the column can be placed adjacent to the heating member containing a microwave absorbing material in any of a number of possible configurations. For example, the column can be placed directly in contact with the microwave absorbing material, or placed adjacent to the microwave absorbing material to provide adequate heat transfer.

There are many different possible assemblies of microwave absorbing materials and chromatographic columns that will keep the column in proximity to the heating member such that the column is heated indirectly by the absorbing material in a microwave heating apparatus. It should be clear to one of average skill in the art that the invention lies in combining a microwave absorbing material and a chromatographic column in an assembly that makes microwave heating possible and not in the specific physical configuration of the assembly.

Microwave absorbing materials used in chromatographic column or column assemblies built in accordance with this invention must have dielectric or magnetic loss factors that are high enough to make microwave heating feasible. Dielectric and magnetic loss factors are often temperature dependent. This characteristic can be utilized to design column assemblies that can only be heated in a microwave heating apparatus to a target temperature and no higher. This design feature can prevent over-temperature conditions that can damage or destroy a column.

Intrinsic over-temperature protection is achieved by selecting a microwave absorber for which the dielectric or magnetic loss factor decreases rapidly at temperatures approaching the maximum desired use temperature of the chromatographic column. As the loss factor of the selected microwave absorber decreases with increasing temperature, the rate at which it absorbs energy in a microwave heating apparatus will also decrease. At some critical point, the temperature will stabilize at a fixed value. This mechanism is illustrated in FIGS. 9 and 10.

Figure 9:
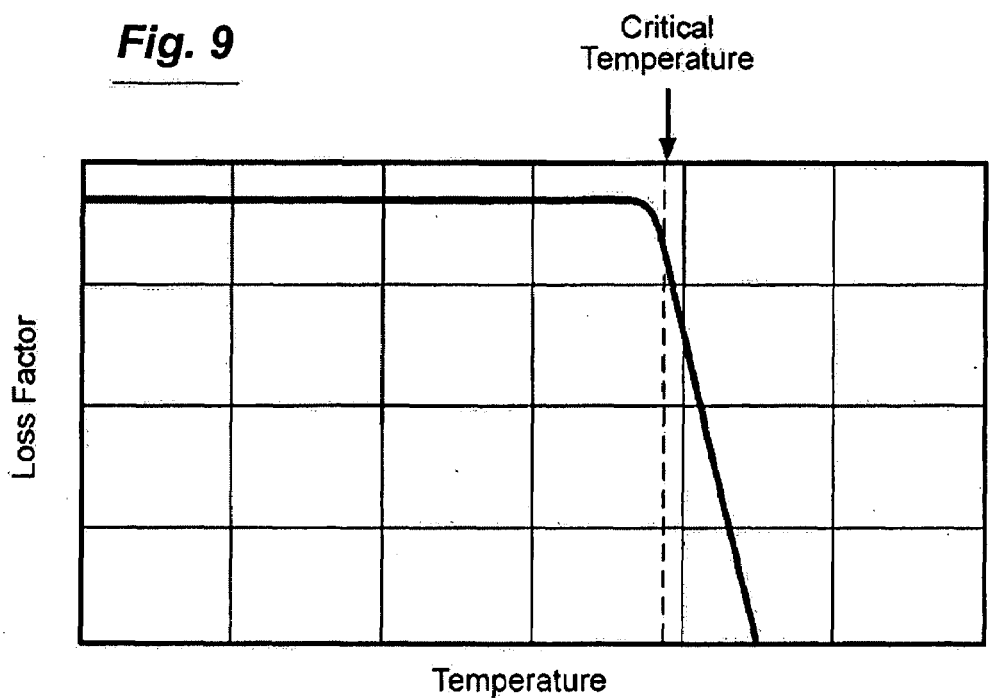
FIG. 9 is a graph illustrating the loss factor of a microwave absorbing material that could be used to limit the maximum temperature to which a chromatographic column assembly built in accordance with this invention can be heated in a microwave heating apparatus.

FIG. 9 shows the loss factor as a function of temperature for a microwave absorbing material that could be used to give a chromatographic column intrinsic over-temperature protection. The loss factor is stable at lower temperatures, but decreases rapidly above some critical temperature. In practice, the loss factor of a suitable microwave absorbing material need not be constant at low temperatures as shown in FIG. 9. The loss factor must simply remain high enough for microwave heating to be efficient at temperatures below the critical temperature, but decrease rapidly over a narrow temperature range to a level at which microwave heating is no longer efficient.

Figure 10:
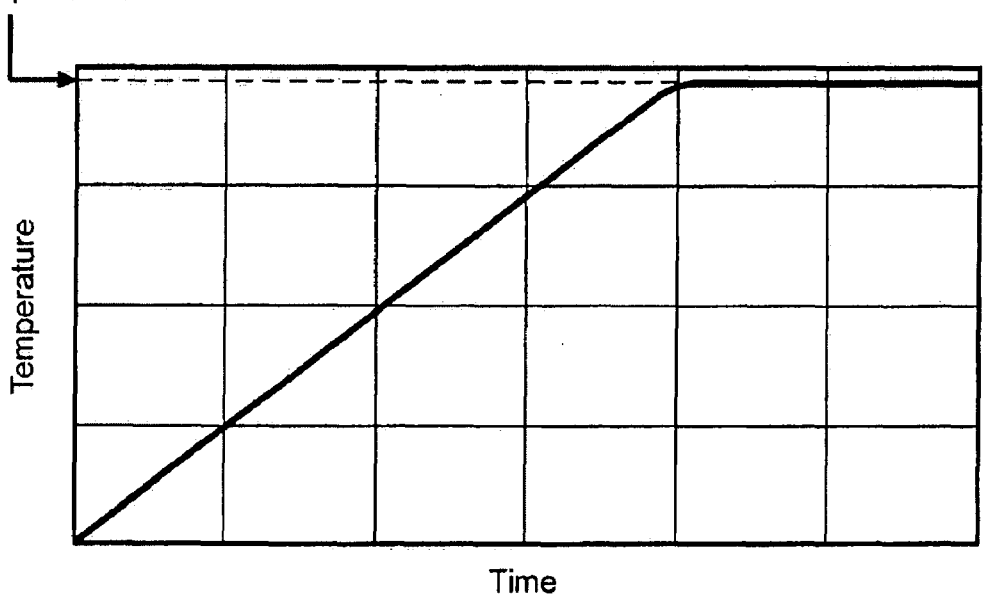
FIG. 10 is a graph showing the heating profile of a column assembly built with intrinsic over-temperature protection in accordance with this invention.

FIG. 10 shows the heating profile for a chromatographic column that is heated in a microwave apparatus where the column is built with a microwave absorbing material that has the loss factor vs. temperature characteristic shown in FIG. 9. At temperatures below the critical loss factor temperature, the rate of temperature increase is substantially constant. At the critical temperature where the loss factor of the microwave absorbing material begins to decrease, the rate of temperature increase slows down. At the temperature at which the heat generated in the microwave absorbing material by the absorption of microwave energy matches the heat lost to the environment, the temperature stabilizes at a fixed value. This temperature is the maximum operating temperature of the column.

Intrinsic over-temperature protection can be achieved by selecting a microwave absorbing material that is ferromagnetic and has an appropriate Curie temperature. The Curie temperature of ferromagnetic materials is the temperature at which they cease to be ferromagnetic and becomes paramagnetic. The Curie temperature also indicates the temperature at which the material's magnetic loss factor approaches zero Thus, a ferromagnetic material cannot be readily heated in a microwave oven beyond its Curie temperatures provided that its dielectric loss factor is also very low. Table 2 shows the Curie temperature of some ferromagnetic materials.

TABLE 2

| Material | Curie Temperature (° C.) |
|---|---|
| Iron | 770 |
| Nickel | 358 |
| Cobalt | 1131 |

Of these materials, nickel is the most suitable for preventing over-temperature conditions in polyimide for which the maximum use temperature is approximately 400° C. Ferrite materials are available with a range of Curie temperatures less than approximately 450° C.

One of the advantages of microwave heating of chromatographic columns over more conventional methods is that thermal energy can be specifically applied to appropriately designed columns or column assemblies and not to the rest of the oven. Because the column or column assemblies have little total material or mass, they also have little thermal mass; therefore, they can be heated or cooled quickly. However, in some circumstances the thermal mass may be so small that heating rates can be compromised by heat lost to the column's environment. Even air surrounding the column may carry away a significant fraction of the thermal energy. An additional problem can arise when cooling the column. If a column is kept at high temperatures for a long period of time, heat loss to the oven environment can eventually raise the temperature of other parts of the oven enough to make quick cooling of the column and the oven difficult. To address these problems, column assemblies built in accordance with this invention can be packaged in a manner which allows the heat flow from the column to be better controlled.

The first element needed to control heat loss from the column is thermal insulation. Columns can be packed in a thermally insulating envelope to minimize the heat loss from them to the rest of the microwave oven. It is not standard practice in the chromatograph business to thermally insulate columns because the columns are heated indirectly in large resistively heated ovens.

Figure 11:
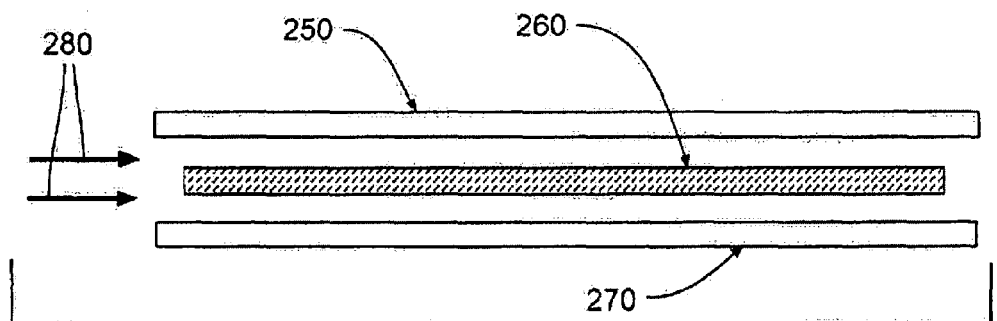
FIGS. 11 and 12 show the cross sections of apparatuses designed to help control the heat loss from column assemblies built in accordance with this invention.

FIG. 11 shows one embodiment of a column insulating system. The perspective in FIG. 11 is the same as in FIG. 7. A column or column assembly 260 built in accordance with this invention may be sandwiched between two thermal insulators 250 and 270 which reduce the heat loss from the column to the environment. In a preferred embodiment, the column assembly insulators 250 and 270 are made into concentric cylinders with the column assembly 260 coiled between them. This structure is as shown in FIG. 8. Insulators 250 and 270 need not be the same material and one or the other may be eliminated in some circumstances. A gap can be left between the thermal insulators 250, 270 and the column assembly 260 for ventilation to facilitate rapid cooling of the column assembly 260 after completion of the heating cycle.

Besides the need to cool the column down after an analysis, column cooling is also needed in order to introduce a negative or cooling temperature ramp into a separation protocol. Under such conditions, the cooling rate must be controlled in such as way as to obtain a given rate of cooling. Although the rate of cooling can be performed simply by the introduction of a gaseous coolant having a temperature and flow rate sufficient to generate a desired negative temperature ramp across the column, in many instances, the coolant temperature and flow rate have to be controlled coupled with a given supply of microwave radiation. By using a combination of heating and cooling, any desired negative temperature ramp can be created in a separation protocol. Thus, the coolant can any inert gas capable of being cooled including, nitrogen, helium, neon, argon, or the like or mixtures or combinations thereof. Preferably, the gaseous coolant is nitrogen and the nitrogen is source is a liquid nitrogen tank. The use of liquid nitrogen permits large negative temperature gradients to be imposed across the column.

Figure 12:
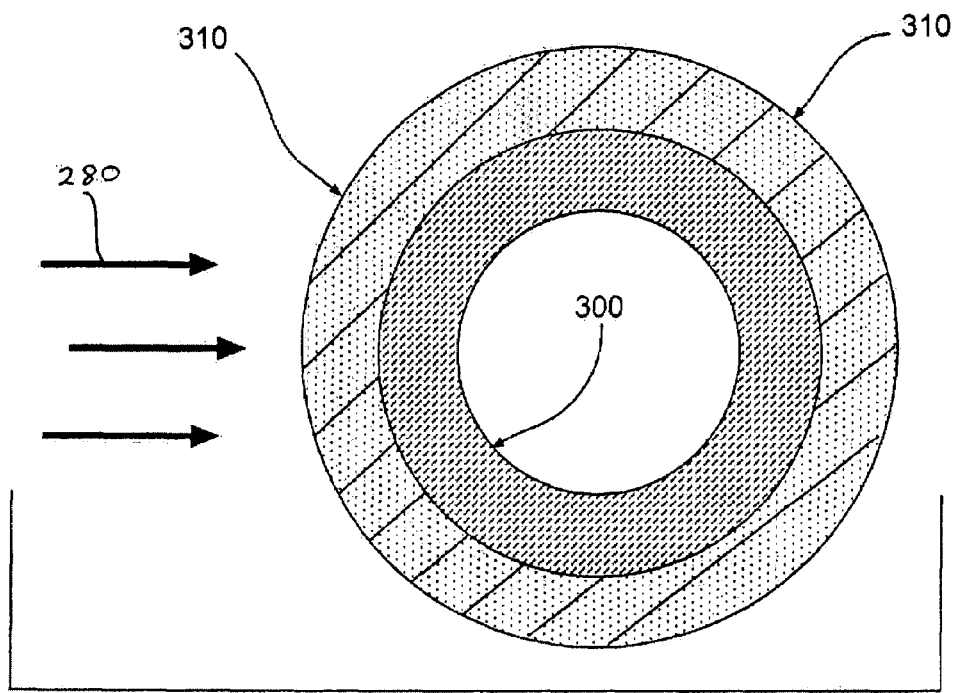

In another preferred embodiment as shown in FIG. 12, a column 300 built in accordance with this invention is sheathed within a layer of thermal insulation 310 that reduces heat loss from the column. If the material layer 100 in FIG. 4 is a good thermal insulator, a separate layer of thermal insulation may not be necessary. As described in reference to FIG. 4, an outer layer of polyimide is attractive because it helps to shield the microwave absorbing material 90 from the environment. As polyimide is a good insulator, it can also help thermally shield the column.

There are many different thermal insulators that could be used in this invention: plastics, ceramics, and fiberglass to name a few. Another possible insulator is a vacuum. If most of the air is pumped out of a microwave heating apparatus so that a column assembly is heated in a vacuum, then very little heat will be lost from the column at useful chromatographic temperatures. The two requirements for the insulation material are that: (1) it must be transparent to high frequency electromagnetic radiation such that it does not shield the column assembly from this radiation and thus prevent the column assembly from heating; and (2) it must have low dielectric and magnetic loss factors so that it will not be heated directly by microwave radiation.

The second element needed to control heat loss from the column is a means for quickly removing the heat from the column or column assembly when cooling is required. In other words, a means of circumventing the thermal insulation and accelerating thermal loss. Accelerated thermal loss is most easily achieved by blowing cool air, a cryogenic gas, or some other convenient material 280 over the column assembly as shown in FIGS. 11 and 12 until the temperature is reduced to the desired level. If the heating process is performed in a vacuum, then blowing cool air through the oven during the cool down cycle will quickly reduce the column temperature to the desired level. If the column assembly is equipped with an outer layer of thermal insulation as depicted in FIG. 11, a blower or ventilation system can be used to induce a flow of air through the gap between the insulation layer and the column to accelerate cooling after completion of each heating cycle.

Conductivity Limits in Columns or Column Assemblies Heated with Microwaves. Materials with high electrical conductivity, such as metals, tend to short out or significantly distort the electromagnetic field within microwave heating apparatuses thus preventing normal microwave heating. However, the electromagnetic field is only distorted significantly if a high conductivity path extends for some length parallel to the electric field. Thus, a metal wire or sheet will not disturb the electric field in a microwave heating apparatus if the sheet or wire is placed in the heating apparatus in a position that is essentially perpendicular to the electric field lines in the heating apparatus. The reason for this is that significant electric currents are not induced in a metal wire by an electric field that is perpendicular to the wire. This behavior can affect the design of columns or column assemblies to be heated in microwave heating apparatuses.

Microwave absorbing material must be added to a column or column assembly in order to heat them in microwave heating apparatuses. Many microwave absorbing materials or matrices are least partly conductive electrically. Carbon-loaded polyimide can be quite conductive for example. The conductivity of microwave absorbing materials or matrices used to heat chromatographic columns in microwave heating apparatuses must not be too high. The upper conductivity limit depends upon the orientation of the microwave absorbing material with respect to the electric field within a given microwave heating apparatus.

Figure 13:
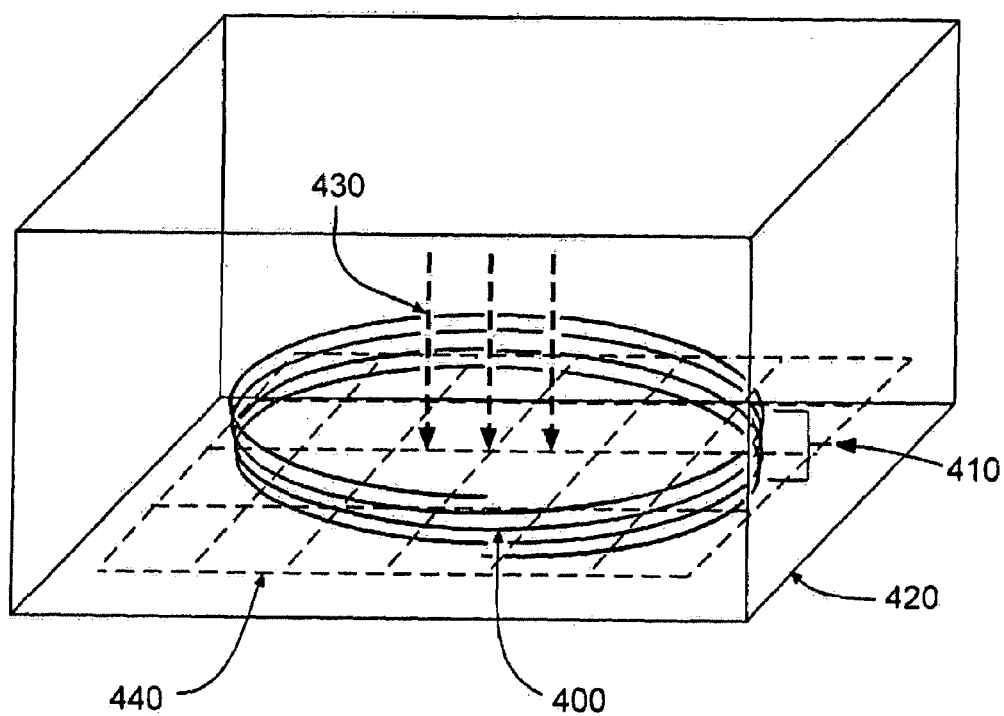
FIG. 13 shows a column configuration in which the microwave absorbing material is essentially perpendicular to the direction of the electric field in a microwave heating apparatus.

A microwave absorbing material oriented essentially perpendicular to the electric field in a microwave heating apparatus has no significant electrical current path length parallel to the electric field. An example of such a structure is shown in FIG. 13. A column 400 with a microwave absorbing material coated on the outside as shown in FIG. 3 is coiled into a circular column bundle 410. The column bundle 410 is placed in a microwave heating apparatus 420 in which the electric field 430 is perpendicular to the plane 440 of each loop of the column bundle 410. When the electrical current path in a microwave absorbing material used to heat a column or column assembly is essentially perpendicular to the electric field in a microwave heating apparatus, the volume conductivity of the microwave absorbing material can be as high as approximately 5000 mho/cm. Conversely, if the microwave absorbing material is positioned in a microwave heating apparatus such that there is a conductivity path of sufficient length (greater than 2% of the free space wavelength) that is parallel to the electric field, then the maximum conductivity of the microwave absorbing material is approximately 100 mho/cm.

An Oven Utilizing Free Space Propagation

Figure 14:
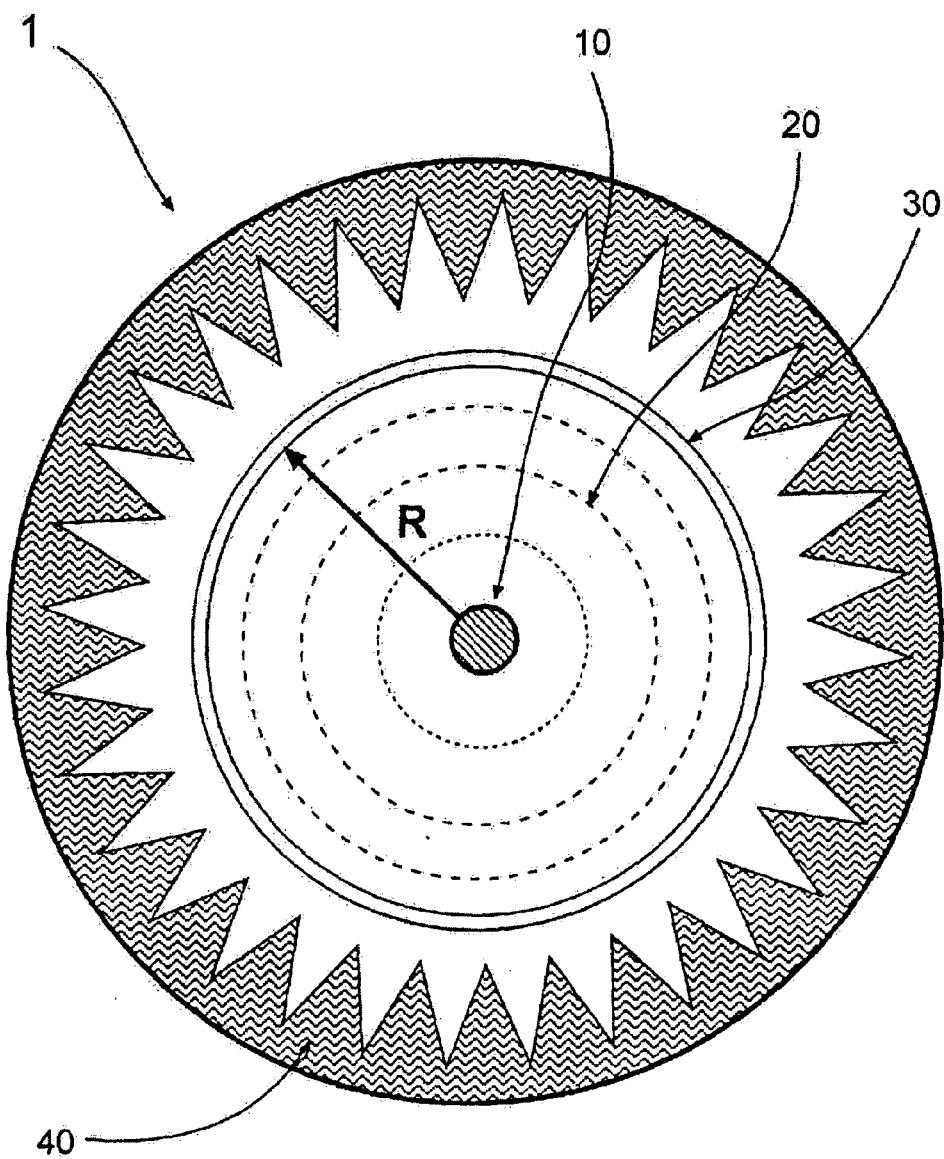
FIG. 14 is a cross-sectional view of a spherical chromatographic column microwave oven in which the chromatographic column is exposed to a constant field strength over its entire length.

FIG. 14 shows the cross section of a spherical chromatographic microwave oven 1 that could be used. A point source antenna 10 emits electromagnetic waves 20 which propagate spherically outward from the antenna 10. This is free space propagation. At the surface of any sphere a fixed distance from the point source antenna 10, the electromagnetic field strength is constant.

A chromatographic column 30 is coiled in such a manner that the whole length of the column is located an equal distance R from the source 10. The column 30 will absorb some portion of the energy in the electromagnetic field. The microwave energy that the column 30 does not absorb will continue to propagate outwards. To prevent unwanted reflection of the remaining electromagnetic waves back toward the column and the consequent disturbance of the isofield conditions which exist at R, an spherical absorber 40 encloses and isolates the oven. The absorber 40 absorbs microwave energy. The absorber 40 also prevents disturbance of the internal field by radiation from external sources.

The chromatographic microwave oven 1 is a poor design for several reasons. It is quite large and mechanically clumsy. It is also energy inefficient. Most of the microwave energy is absorbed by the absorber 40 and not by the column 30. This inefficiency compromises heating and cooling times and potentially increases the cost of the oven 1 because the lost microwave energy is expensive to generate. If the absorber 40 is substituted by a hollow metal sphere that internally reflects all electromagnetic energy, the oven 1 is a spherical resonant cavity. This structure is more energy efficient, but spherical resonators are not practical to use for this application.

Useful chromatographic column microwave ovens must generate stable and predictable electromagnetic field profiles having isofield lines that can be traced by a column. A chromatographic column with a constant microwave loss factor along its length that lies on an isofield line in a microwave oven will be heated isothermally in that oven. Long chromatographic columns can be reduced to a manageable size by winding them into a circular bundle. Microwave ovens with circular cross sections can be designed with radially symmetric electromagnetic fields having circular isofield lines. Because of this feature, most chromatographic column microwave ovens described herein have circular cross sections.

A typical coiled chromatographic column must be wound into more than one coil. A 60 m, 0.35 mm column wound to a diameter of 15 cm must be wound over 127 times. If bundled into a cylindrical coil of constant radius that is only one column thick, the resulting column cylinder is 4.45 cm long. The axial length of the coil is of the same order of magnitude as its diameter. Thus, the axial electromagnetic field distribution is as important in a chromatographic column microwave oven as the radial field distribution. Suitably designed microwave ovens having circular cross-sections combine: (1) radially symmetric electromagnetic field distributions; and (2) well defined axial electromagnetic field gradients.

Coaxial Chromatographic Column Microwave Ovens

Figure 15:
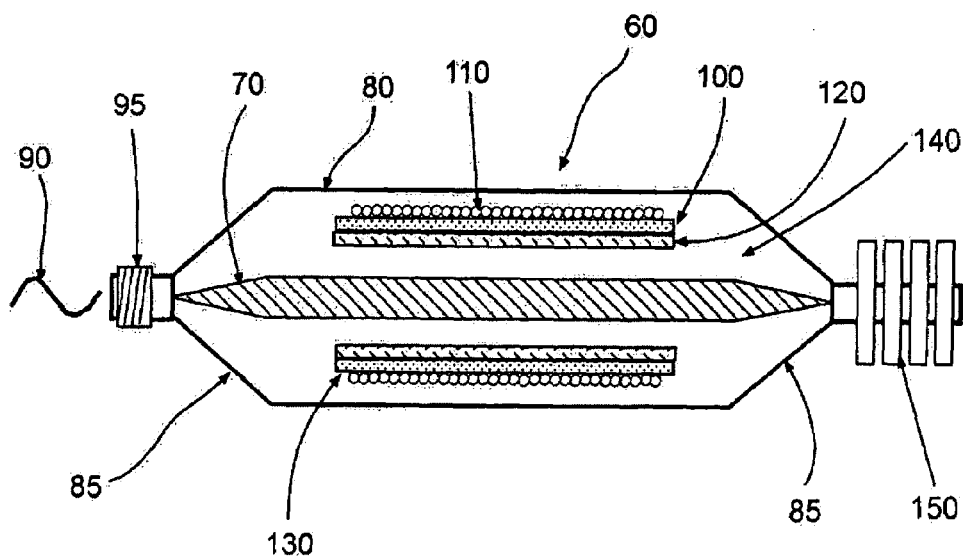
FIG. 15 and FIG. 16 are two orthogonal cross-sectional views of a chromatographic column microwave oven wherein the oven is a coaxial transmission line.
Figure 16:
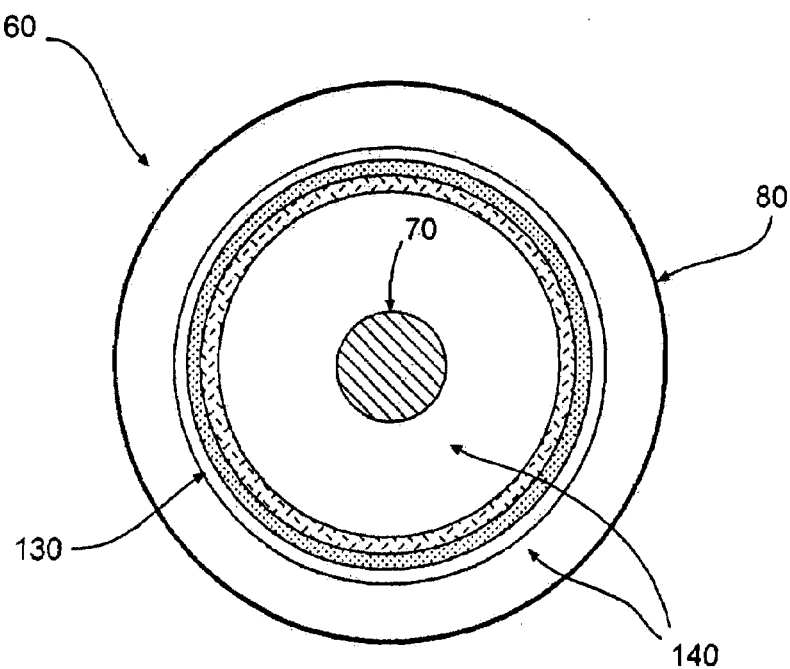

FIGS. 15 and 16 show two orthogonal cross-sectional views of one embodiment of a cylindrically shaped chromatographic microwave oven 60. The oven 60 is a coaxial transmission line structure. It is the coaxial analog of the spherical oven 1. FIG. 15 shows a cross sectional view along the central axis of the chromatographic microwave oven 60. FIG. 16 shows the radial cross section perpendicular to the central axis in the middle of the oven 60.

A microwave signal 90 is coupled into the oven 60 through a coaxial connector 95. The electromagnetic field propagates from left to right in the space 140 between a metallic cylindrical inner conductor 70 of the coaxial oven 60 and a metallic cylindrical outer wall 80. To prevent undesirable reflection of microwave energy out of the microwave oven 60 through the connector 95, a conical impedance matching section 85 is used to transition between the smaller-diameter coaxial connector 95 and the larger-diameter main section of the coaxial oven 60.

The outer enclosure of oven 60 consisting of conical impedance matching section 85 and outer wall 80 defines the boundary of a cavity which substantially prevents electromagnetic radiation from escaping from the oven 60. All of the chromatographic microwave ovens described herein comprise cavities which substantially isolate electromagnetic phenomenon within the interior space defined by the boundaries of the cavity from the environment.

A cylindrical sheet of microwave absorbing material 100 is positioned concentrically about the central axis of the oven 60 in the gap between the inner and outer conductors 70 and 80. Around and adjacent to absorbing material 100 is coiled a chromatographic column 110 which is heated together with the absorbing material 100 in the oven 60. Together, the absorbing material 100 and the adjacent column 110 constitute a microwave absorbing chromatographic column assembly. It should be understood that absorbing material 100 and the column 110 could be substituted with any microwave absorbing column assembly without materially affecting the teaching of this invention.

An optional mechanical support 120 is provided to hold the absorbing material 100 and the column 110 in place within the oven 60. As shown, the mechanical support 120 is a thin walled cylindrical structure of fixed length outside of which is wrapped the absorbing material 100 and the column 110. The mechanical support 120 need not be a cylindrical pipe nor must the absorbing material 100 and the column 110 be wrapped around it. It could just as readily be place between absorbing material 100 and the column 110 or it could lie outside of both without materially affecting the performance of the oven 60.

Taken together, the absorbing material 100, the column 120, and the mechanical support 130 constitute a common element in all chromatographic column microwave oven embodiments described herein. Henceforth, they are treated as a single element 130 and called a column heating element. The term column heating element incorporates any microwave absorbing column assembly together with an optional mechanical support. Many different embodiments and configurations of the these subcomponents are possible. It should obvious be one of average skill in the art that the invention is not limited to a specific one.

Microwave energy not absorbed by the column heating element 130 passes though a second impedance matching transition 85 and into a load element 150 which absorbs it.

All cylindrical elements within the oven 60 are concentrically oriented about the same axis. Consequently, the electromagnetic field is radially symmetric in the oven 60. The diameter of the oven 60 built in accordance with this specification is typically between 3 and 25 cm.

As specified, the oven 60 has significant drawbacks. First, the electromagnetic field strength is not constant axially in the oven 60 nor in the column heating element 130. The electromagnetic field strength decreases axially as it propagates through the oven 60 because energy is absorbed by the column heating element 130. Thus, there is a temperature gradient from high to low along the length of the column 110 in the direction of microwave propagation There are several ways to adjust the axial variation in field strength. They are described subsequently. The second weakness of the oven 60 is that it is energy inefficient. Much of the microwave energy 90 injected into the oven 60 is lost in the load 150. It does not heat the column heating element 130. The loss factor of the column heating element 130 can be increased so that a higher percentage of the microwave energy 90 is dissipated in the column heating element 130. However, this increases the gradient of the electromagnetic field in the axial direction making steeper the temperature profile of the column 110.

A coaxial resonant cavity chromatographic column microwave oven is far more energy efficient than the coaxial transmission line microwave oven 60. Resonant cavities are a special class of cavity as the term is used herein in which confined electromagnetic energy can develop into high field strength standing wave patterns as a result of multiple internal reflection. Virtually all microwave energy injected into a resonant cavity chromatographic column microwave oven will be absorbed by the column heating element. Coaxial resonant cavities have radially symmetric electric fields just as coaxial transmission lines do.

Figure 17:
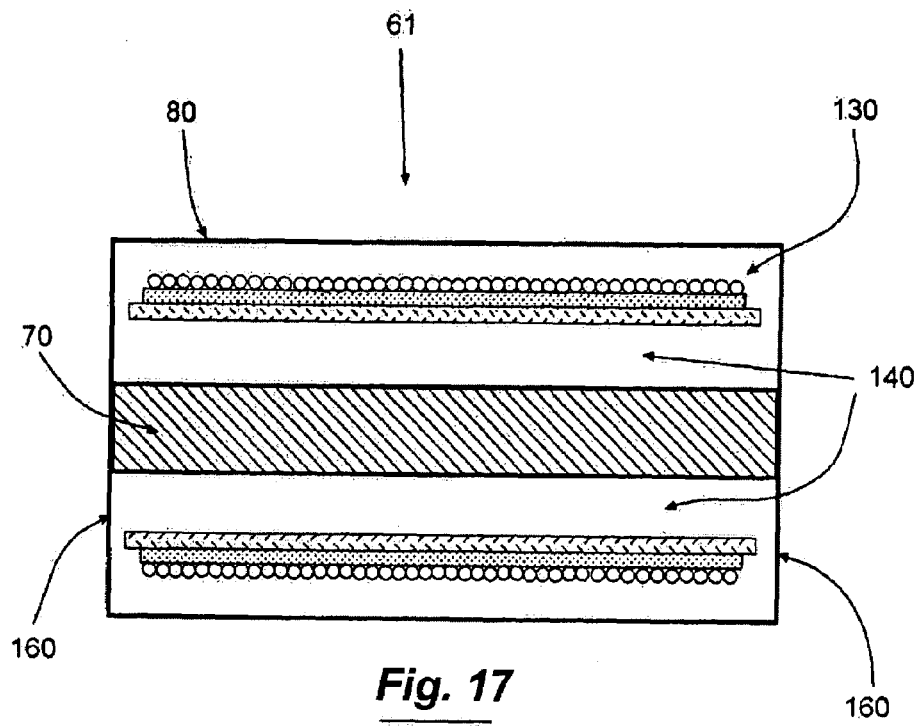
FIG. 17 is a cross-sectional view along the central axis of a chromatographic column microwave oven wherein the oven is an short-circuited coaxial resonant cavity.

FIG. 17 illustrates a chromatographic column microwave oven 61 constructed as a short circuited coaxial resonant cavity. FIG. 17 shows the cross section of the oven 61 along its central axis. The radial cross section of the oven 61 is identical to that of the oven 60 shown in FIG. 16. A metallic inner conductor 70 and a concentric metallic outer conductor 80 comprise the coaxial parts of the oven 61. They are electrically connected together at both ends with round metal discs 160 which also serve to seal the oven 61 if air in the space 140 is pumped out. A cylindrical column heating element 130 is centered around the central axis.

The internal axial length of the oven 61 is 'D'. The oven 61 will resonate at those frequencies at which the wavelength is equal to 2D, D, 2D/3, D/2, 2D/5 . . . and so on. At the lowest order resonance, the cavity is one half a wavelength long. Ignoring the absorption of the field by the column heating element 130, the axial electric field strength at a fixed radius within the oven 61 is given by the following equation:

$$E(z)=E_{max} \sin(\pi z) \quad (1)$$

where: z is the normalized axial position in the oven 61 (i.e., z=0 at one end cap 160 and z=1 at the other), E(z) is the axial electric field strength in the oven, and $E_{max}$ is the maximum axial electric field strength.

Figure 18:
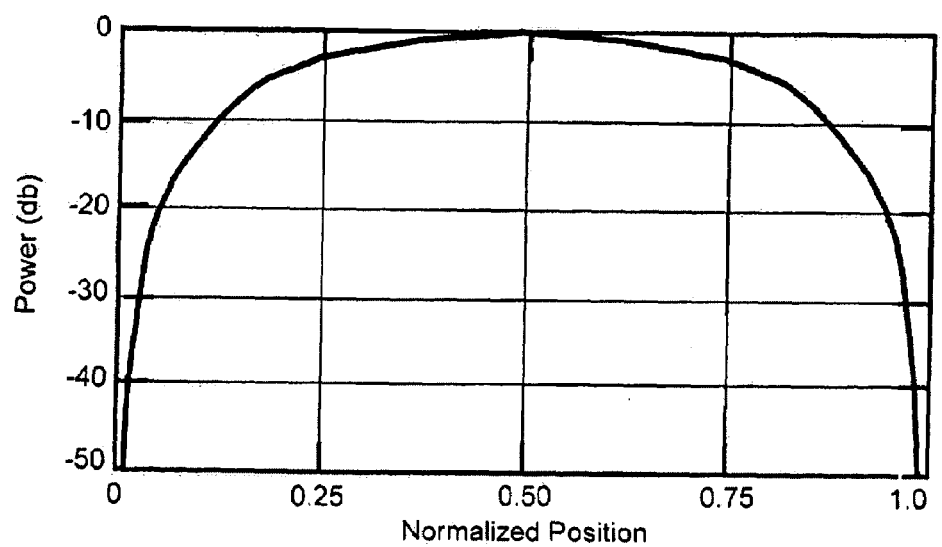
FIG. 18 is a graph showing the microwave power distribution along the length of a short-circuited coaxial resonant cavity.

The axial power distribution of the electric field is described by the following equation:

$$P=20 \log 10[E(z)/E_{max}] \quad (2)$$

where P is the power in decibels (dB) relative to the maximum power point. FIG. 18 is a graph showing the electric field power distribution in an oven 61 along its length.

Figure 19:
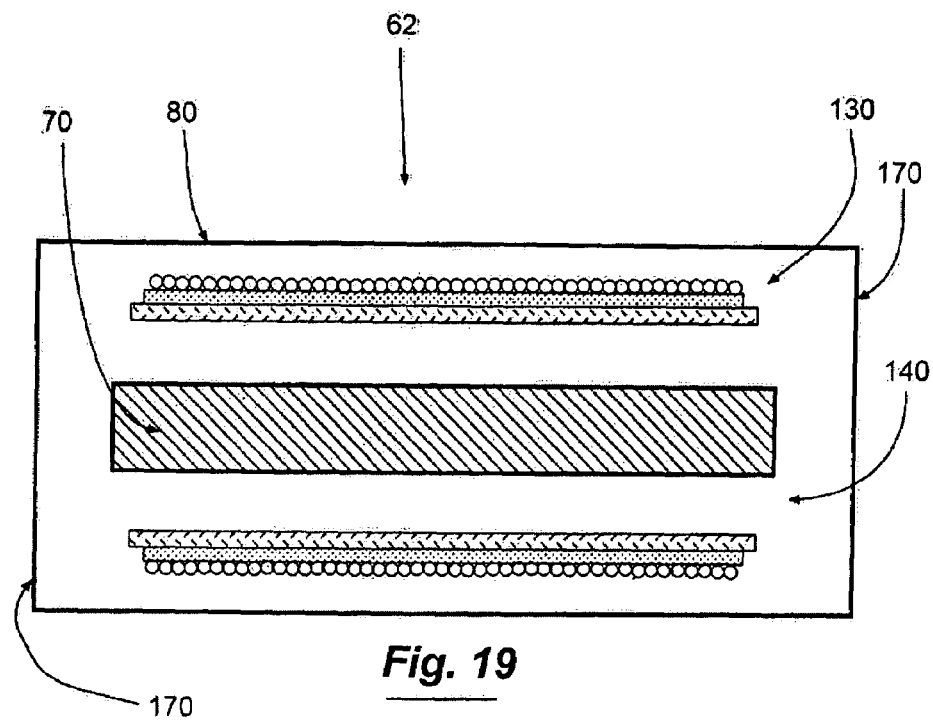
FIG. 19 is a cross-sectional view along the central axis of a chromatographic column microwave oven wherein the oven is an open-circuited coaxial resonant cavity.

FIG. 19 illustrates a similar chromatographic column microwave oven 62 constructed as an open circuited coaxial resonant cavity. FIG. 19 shows the cross section of the oven 62 along its central axis. The radial cross section of the oven 62 is identical to that of the oven 60 as shown in FIG. 16. The oven 62 has a metal cylindrical inner conductor 70, and concentric metal cylindrical outer conductor 80, between which is a concentric cylindrical oven heating element 130. The inner conductor 70 and the outer conductor 80 are not connected together electrically. The oven ends are sealed with circular endplates 170 such that the air in the space 140 inside the oven 62 can be pumped out. The endplates 170 can be metallic or nonmetallic. If metallic, then the outer conductor 80 must be longer than and not come into electrical contact with the inner conductor 70 as shown in FIG. 19.

The length of the inner conductor 70 is 'D'. The oven 62 will resonate at those frequencies at which the wavelength is equal to 2D, D, 2D/3, D/2, 2D/5 . . . and so on. At the lowest order resonance, the inner conductor 70 is one half a wavelength long. Ignoring the absorption of the field by the column heating element 130, the axial electric field strength at a fixed radius within the oven 62 is given by the following equation:

$$E(z)=E_{max} \cos(\pi z) \quad (3)$$

Figure 20:
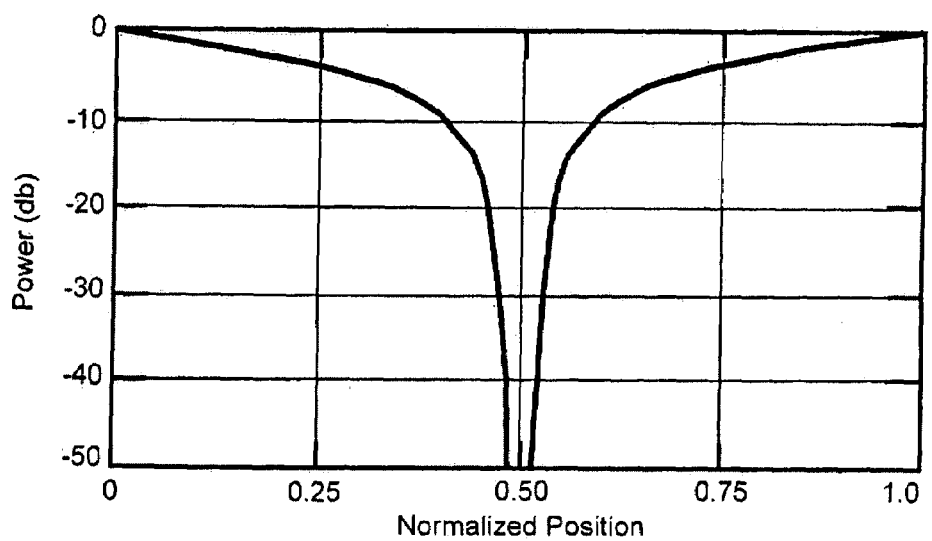
FIG. 20 is a graph showing the microwave power distribution along the length of an open-circuited coaxial resonant cavity.

FIG. 20 is a graph showing the corresponding power distribution of the oven 62 along the length of the center conductor 70.

Within the ovens 61 and 62, each single coil of the chromatographic column follows an isofield line and is thus heated isothermally. However, the axial power distributions of the electric fields in the ovens 61 and 62 respectively vary greatly as shown in FIGS. 18 and 20, respectively. The power varies by 50% (about 3 dB) over the center 50% of the oven 61. The corresponding temperature gradient would also be approximately 50% as compared to ambient temperature.

There are methods, which will be described subsequently, with which the axial power distribution of the electromagnetic field can be altered in the ovens 61 and 62. But, the axial field strength cannot be made constant over the entire oven length. Consequently, the ovens 61 and 62 would be much longer physically than the column heating element 130. The absorption of microwave energy by the column heating element 130 in the ovens 61 and 62 will somewhat alter the power distributions shown in FIGS. 18 and 20 without significantly altering the essential characteristics of these oven embodiments.

Another type of coaxial resonant cavity that could be used is a hybrid of those used the ovens 61 and 62 (i.e., a cavity with a short circuit on one side and an open circuit on the other). This cavity would resonate at frequencies where the wavelength is equal to 4D, 4D/3, 4D/5, 4D/7 . . . and so on, where D is equal to the length of the center conductor.

Operating Chromatographic Column Microwave Ovens in Vacuum

A problem common to the chromatographic column microwave ovens 60, 61, and 62 and all other oven embodiments described herein is redistribution of heat in the column heating element 130 by air. If gap 140 is filled with air at atmospheric conditions, some of the heat in column heating element 130 will be transferred to the air. Because hot air rises, air movement alters the heat distribution in the oven. Over time, the upper part of the ovens including the upper part of column heating element 130 becomes hotter than the lower parts. This undermines the isothermal conditions that a carefully designed and symmetrical oven can establish and it will slow heating and cooling times. This problem can be partially addressed by altering the geometry of the oven to compensate for the heat transport in the air. However, this is not a good solution because air driven heat transport is unpredictable. A better solution to the problem is to pump most of the air out of the interior of the oven such that the undesirable transport of thermal energy from the column heating element 130 does not occur at a significant rate. Subsequent cooling of the column heating element 130 is achieved by reintroducing air into the oven interior and even pumping air through the oven to more quickly remove the thermal energy from the column heating element 130. Heating in vacuum maximizes heating and cooling rates. The performance of all chromatographic column microwave ovens described herein is significantly improved by operating them in vacuum conditions.

Circular Cylinder Resonant Cavities

Figure 21:
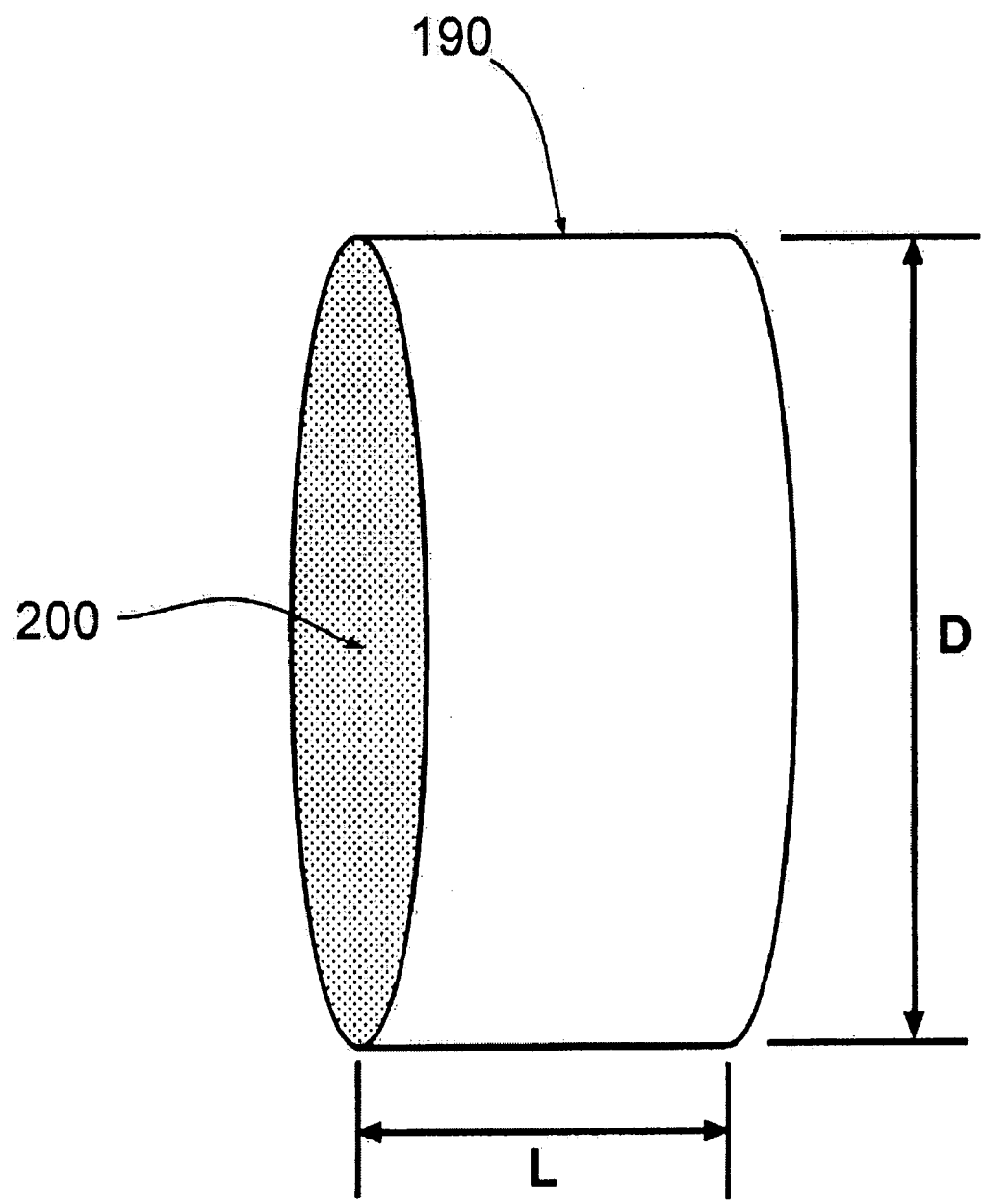
FIG. 21 is a perspective view of a cylindrical resonant cavity.

Certain modes of circular cylindrical resonant cavities have constant electromagnetic field strengths at fixed radii over their axial length and so are a better choice for a chromatographic column oven than coaxial resonator ovens. A circular cylindrical resonant cavity is essentially the same cavity shown in FIG. 17 without the center conductor. FIG. 21 is a drawing of such a resonant cavity having a diameter D and an axial length L. It consists of a cylindrical metal wall 190 with metal end caps 200 at either end oriented perpendicular to its central axis.

Circular cylindrical resonant cavities can support many modes if the wavelength is smaller than the length and/or the diameter of the cavity just as a conventional rectangular microwave cavity does. Some of the possible modes are radially symmetric. Others are not. Ideally, a chromatographic column microwave oven will only support one mode so that there is no uncertainty in the electromagnetic field distribution. If more than one mode is present, the relative power distribution between the modes can change such that the field distribution varies over time. Thus, a chromatographic column microwave oven should be a single mode oven and not a multi-mode oven.

The resonant frequencies for different modes in cylindrical resonant cavities can be calculated from cavity length L and diameter D. Table 3 shows the resonant frequency for various modes in three cylindrical resonant cavities, each with a diameter of 25 cm.

TABLE 3

| | Frequency (GHz) | | |
|---|---|---|---|
| Mode | L = 8 cm | L = 15 | L = 25 cm |
| TM010 | 0.919 | 0.919 | 0.919 |
| TE111 | 2.000 | 1.219 | 0.919 |
| TM020 | 2.108 | 2.108 | 2.108 |
| TM110 | 2.378 | 1.772 | 1.581 |
| TM011 | 2.085 | 1.354 | 1.092 |
| TE211 | 2.212 | 1.542 | 1.319 |
| TE011 | 2.379 | 1.773 | 1.582 |
| TM111 | 2.379 | 1.773 | 1.582 |
| TM210 | 1.960 | 1.960 | 1.960 |
| TE311 | 2.469 | 1.892 | 1.715 |
| TM211 | 2.712 | 2.200 | 2.049 |
| TE411 | 2.762 | 2.261 | 2.115 |

The lowest order (i.e., lowest frequency) mode in each cavity is the $TM_{010}$ mode which resonates at 0.919 GHz. As the ratio between D and L decreases, the frequency spread between the $TM_{010}$ mode and the higher order modes decreases. When D/L is one, the $TM_{010}$ and $TE_{111}$ modes resonate at the same frequency and several other modes resonate at frequencies not much higher. This is a situation to be avoided. If a chromatographic column microwave oven is made with a D:L ratio of at least 2 and preferably 3, the $TM_{010}$ mode is clearly separated from the other modes such that the oven will operate as a single mode oven.

The $TM_{010}$ mode has other attractive characteristics for a column heating application. The electromagnetic field distribution is radially symmetric. More importantly, the axial field distribution is theoretically predicted to be constant over the whole length of the cavity when no perturbations are present in the cavity. All $TM_{0n0}$ modes where n=1, 2, 3, . . . share these important properties. The electric field distribution in a $TM_{010}$ resonant cavity is given by the following equation:

$$E(z)=E_{max}J_0(R/Ro) \quad (4)$$

where: $J_0$ is the zero$^{th}$ order Bessel function, R is the radius at which E(z) corresponds, and Ro is the radius of the resonant cavity (i.e., D/2).

FIG. 22 is a graph showing the electric field distribution across the diameter of a $TM_{010}$ cavity. There is no axial variation along the length L. FIG. 23 is a graph showing the corresponding power distribution calculated by inserting Equation 4 into Equation 2.

A Single Mode $TM_{010}$ Chromatographic Column Microwave Oven

The $TM_{010}$ circular cylindrical resonant cavity is the most suitable structure for a chromatographic column microwave oven. It has a radially symmetric, axially invariant electromagnetic field distribution and higher order modes are readily inhibited.

Figure 24:
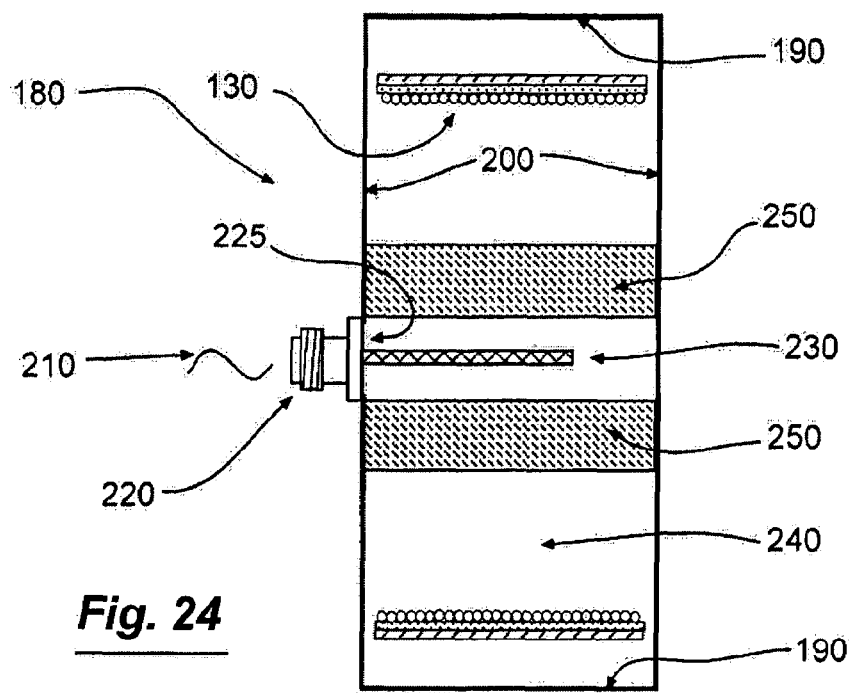
FIGS. 24 and 25 are two orthogonal cross-sectional views of a chromatographic column microwave oven wherein the oven is a cylindrical resonant cavity.
Figure 25:
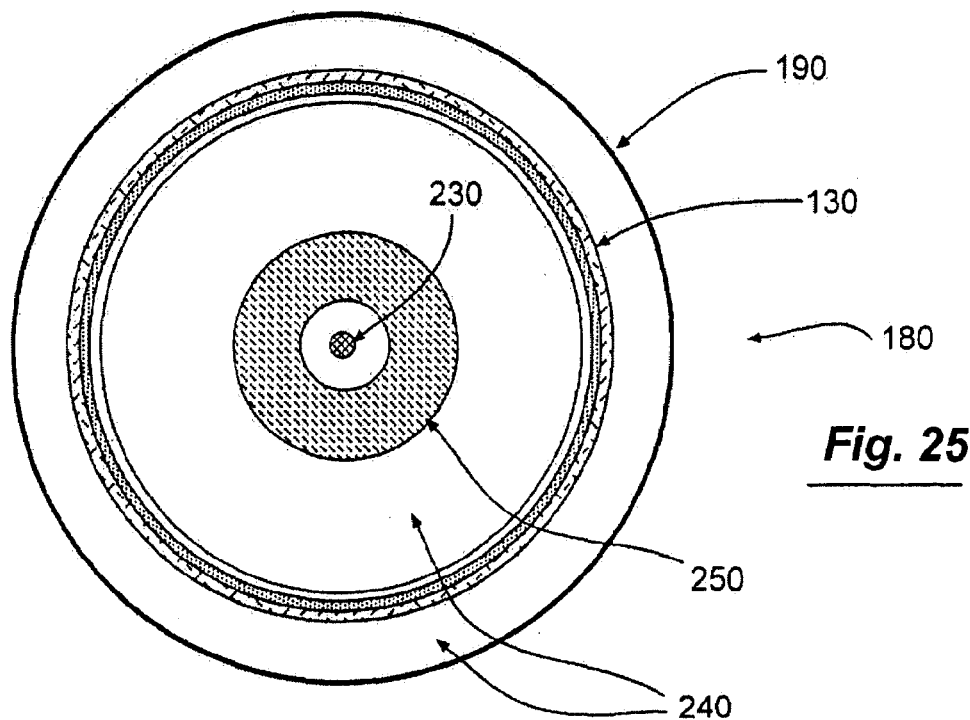

FIGS. 24 and 25 show two orthogonal cross sectional views of a chromatographic column microwave oven 180 utilizing this mode. FIG. 24 is an axial view along the central axis and FIG. 25 a radial cross section. The oven 180 consists of a circular metal cylinder 190 of length L1 and diameter D1. The cylinder 190 is closed off at either end by two circular metal caps 200 of diameter D1. Together, the metal cylinder 190 and the end caps 200 form the outer wall of the chromatographic column microwave oven 180 and form a circular cylindrical resonant cavity as shown in FIG. 21. To separate the $TM_{010}$ mode from higher order modes, diameter D1 should be at least twice as great as length L1.

A hole 225 is cut in the center of one of the end caps 200. A coaxial microwave connector 220 is connected to the center of the end cap 200 with the hole 225 in it. The center conductor 230 of the coaxial connector 220 protrudes into the oven 180 along the central axis through the hole 225 in the end cap 200. The center conductor 230 must not contact end cap 200.

A microwave signal 210 transmitted through the connector 220 will radiate in part into the oven from the center conductor 230 which acts as an antenna. That portion of the microwave signal 210 not radiated into the oven 180 is reflected back out of the oven 180 through connector 220. Inside the oven 180 is a cylindrical column heating element 130 concentric with metal cylinder 190 which absorbs the microwave energy radiated into the oven 180 by antenna 230. The space 240 inside the oven 180 can be air, but preferably the air should be pumped out during the heating process.

The efficiency of the microwave oven 180 at delivering available microwave power to column heating element 130 can be maximized by tuning the oven. To achieve maximum efficiency, the oven 180 must be operated at the resonant frequency of the $TM_{010}$. In most cases, the frequency of the microwave signal will be restricted to one of two frequency bands centered at 915 and 2450 MHz respectively. These frequency bands have been set aside for such industrial usage as microwave heating. The resonant frequency of the $TM_{010}$ mode depends on the diameter of the cavity. Thus, the diameter D1 of the oven 180 must be such that the oven will resonate at the desired frequency. If a smaller diameter is needed, a cylindrical dielectric tuning element 250 can inserted into the oven 180 to cause it to resonate at a lower frequency than could be achieved otherwise with a given diameter D1. The resonant frequency of the oven 180 can be varied by adjusting the radial thickness of the dielectric 250 or by adjusting its dielectric constant. The dielectric 250 should not absorb microwave energy appreciably or it too will be heated in the oven 180, thus compromising heating and cooling times.

To further increase the efficiency of microwave power delivery, the length of the antenna 230 is adjusted to minimize the amount of microwave energy reflected from the resonant cavity (i.e. to maximize the return loss). The optimal antenna length varies with the total loss factor of the cavity which depends in turn primarily upon the loss factor of the column heating element 130. In practice, changing the length of the antenna 230 also changes the resonant frequency of the oven 180 to some extent.

When properly tuned, the chromatographic column microwave oven 180 can be over 99% efficient in delivering available microwave energy to column heating element 130 in the form of heat. Moreover, the resonant frequency of the system is generally stable over time such that the oven 180 will remain efficient once tuned.

Figure 26:
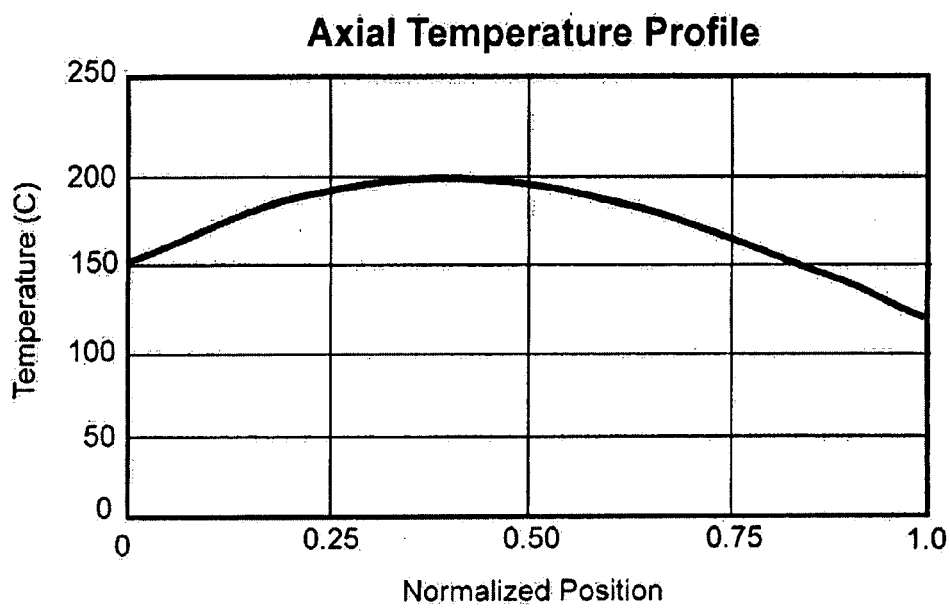
FIG. 26 is a graph showing an axial temperature distribution of a column heating element heated in the $TM_{010}$ microwave oven illustrated in FIGS. 24 and 25.
Figure 27:
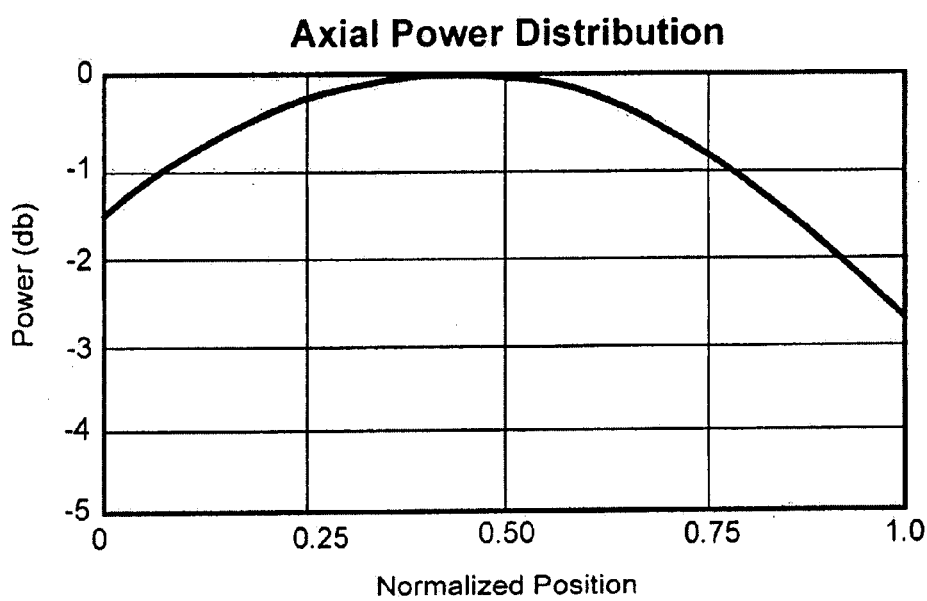
FIG. 27 is a graph showing the approximate axial microwave power distribution of the $TM_{010}$ microwave oven illustrated in FIGS. 24 and 25.

A chromatographic column microwave oven 180 built as shown in FIGS. 24 and 25 has a very even radial temperature profile in the column heating element 130 indicating that the electromagnetic field is radially symmetric as expected. The axial temperature profile is not typically isothermal, however, indicating that the electromagnetic field is not necessarily axially invariant in an oven 180 as would be theoretically expected. This is caused primarily by the presence of electromagnetic absorbing material in the column heating element 130 which disturbs the electromagnetic field distribution. FIG. 26 is a graph showing a typical axial temperature profile of a column heated in an oven 180. FIG. 27 is a graph showing the approximate axial power distribution giving rise to the temperature profile shown in FIG. 26. The microwave power absorbed by the column heating element 130 varies by less than 3 dB over the length of the oven 180. This is significantly better than in the previously described coaxial microwave ovens 61 and 62. Nevertheless, the temperature profile of the chromatographic column in oven 180 is not isothermal.

Modifying the Axial Field Gradient in Chromatographic Column Microwave Ovens

To achieve isothermal conditions (or at least conditions approaching isothermal conditions) on a column heating element in the various described chromatographic column microwave embodiments, the axial electromagnetic field gradient seen by the column heating element must typically be altered. There are several ways this can be achieved. The different methods will be illustrated in chromatographic column microwave ovens embodiments that are derived from the $TM_{010}$ cylindrical resonant cavity oven shown in FIGS. 24 and 25. However, these methods are as readily applied to the other ovens described herein and should be considered as general means for engineering desired axial electromagnetic field gradients into the chromatographic column microwave ovens taught in this invention.

The electric field strength decreases in strength in $TM_{010}$ resonant cavities as the radius increases toward the outer wall of the cavity as seen in Equation 4 and shown in FIG. 22 Assume R(z) represents the radius of a column heating element at each point z along it length and assume Ro(z) represents the radius of the resonant cavity at each point z along its length. If R(z)/Ro(z) is varied as a function of z, then the electric field strength E(z) will vary according to R(z)/Ro(z). Thus, controlling R(z)/Ro(z) provides a way of adjusting the axial microwave power distribution seen by a column heating element in a chromatographic column microwave oven. The electric field distribution in coaxial devices decreases from a maximum at the inner conductor to a minimum at the outer conductor just as it decreases from a maximum at the center of a $TM_{010}$ resonator to a minimum at the outer cylindrical wall. Thus, the methods described for modifying the axial electromagnetic field gradient work equally well in coaxial-based microwave ovens.

Figure 28:
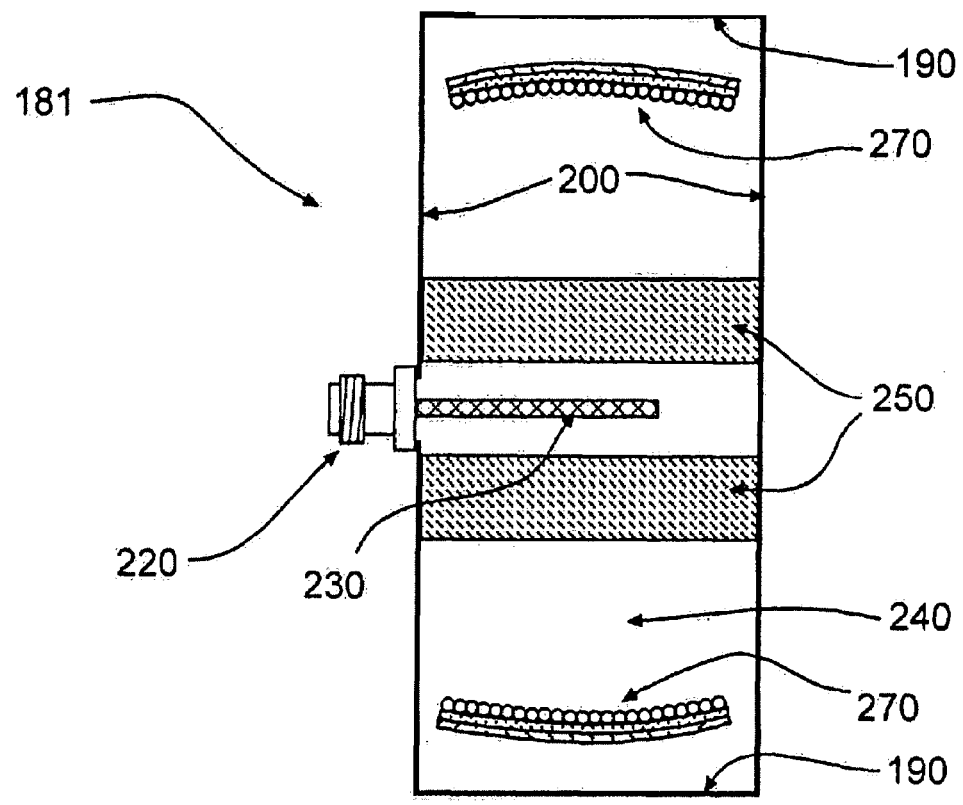
FIG. 28 is a cross-sectional view along the central axis of a chromatographic column microwave oven having a cylindrical resonant cavity in which the diameter of the column heating element varies axially.

Varying the diameter of the column heating element in a chromatographic column microwave oven alters its rate of microwave absorption along its length. FIG. 28 shows the cross section of a chromatographic column microwave oven 181 along its central axis having all of the same elements as the oven 180 shown in FIG. 24 except column heating element 270 replaces column heating element 130. The diameter of the column heating element 270 varies along its length (i.e., R(z) of the column heating element 270 varies while Ro(z) of the cavity wall 190 is constant and doesn't vary with z). R(z)/Ro(z) is smaller at the edges of the column heating element 270 than it is in the middle. Hence, it sees a higher field strength and absorbs more microwave power towards its ends than does the column heating element 130 in FIG. 24. This in turn changes the axial temperature profile of the column heating element 270 from that shown in FIG. 26. By varying the diameter of the column heating element 270 along its length, the temperature profile of the column in the column heating element 270 can be altered.

Figure 29:
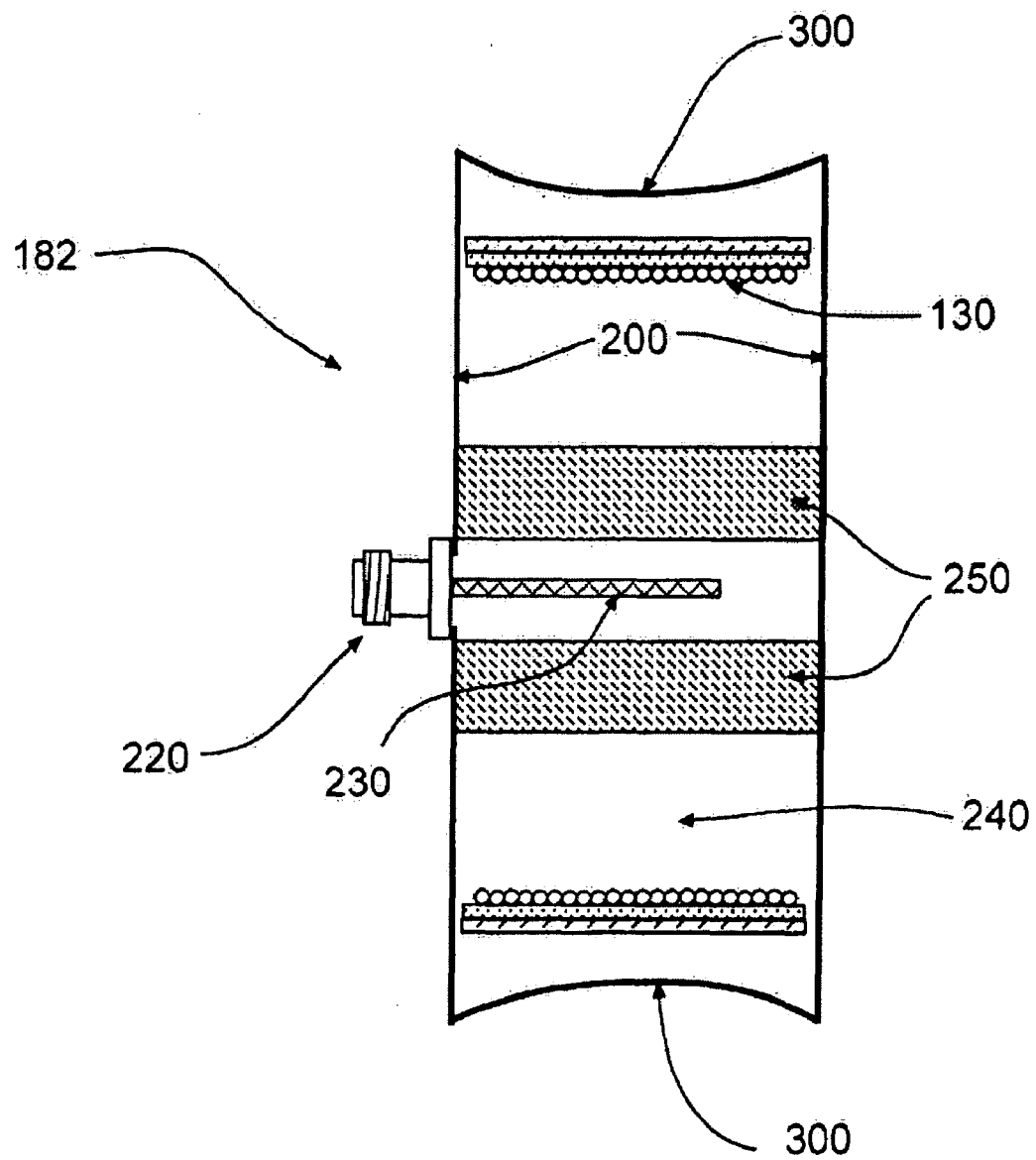
FIG. 29 is a cross-sectional view along the central axis of a chromatographic column microwave oven having a cylindrical resonant cavity in which the diameter of the cylindrical wall.

Varying the diameter of the cylindrical metal enclosure of a chromatographic column microwave oven along its length alters the rate of microwave absorption along the length of a column heating element in the oven. FIG. 29 shows the cross section of a chromatographic column microwave oven 182 along its central axis having all of the same elements as the oven 180 shown in FIG. 24 except the metal cylinder 190 is replaced with a metal enclosure 300 of circular cross section for which the diameter varies along its length. i.e. Ro(z) of the cavity wall 300 varies with z while R(z) of the column heating element 130 is a constant. Depending on the diameter of the enclosure 300 at its ends, the two end caps 200 may have different diameters. As with the oven 181, R(z)/Ro(z) is smaller at the edges of the column heating element 130 than it is in the middle. Hence, it sees a higher field strength and absorbs more microwave power towards its ends than does the column heating element 130 in FIG. 24. This in turn changes the axial temperature profile of the column heating element 130 from that shown in FIG. 26. By varying the diameter of the metal 'cylinder' 300 along its length, the temperature profile of the column in the column heating element 130 is also varied.

Figure 30:
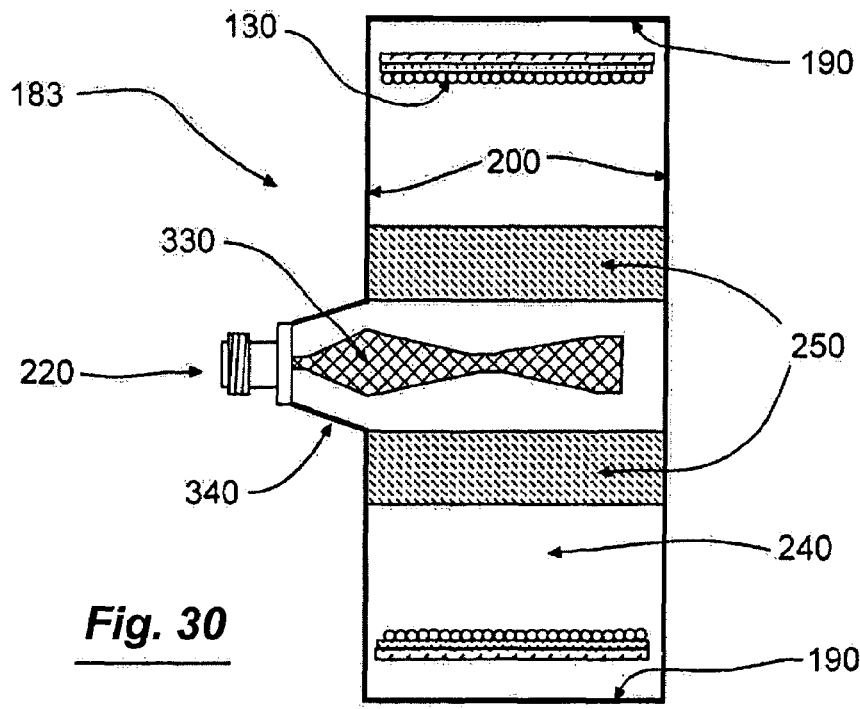
FIG. 30 is a cross-sectional view along the central axis of a chromatographic column microwave oven having a cylindrical resonant cavity in which the outer diameter of the antenna varies axially.

Varying the diameter of the antenna along its length in a chromatographic column microwave oven alters the rate of microwave absorption along the length of a column heating element in the oven. FIG. 30 shows the cross-section of a chromatographic column microwave oven 183 along its central axis having all of the same elements as the oven 180 shown in FIG. 24, except the antenna 190 is replaced with an antenna 330 having a diameter that varies along its length. R(z) of the column heating element 130 and Ro(z) of the cavity wall 190 are measured from the point of maximum electric field intensity in the cavity. The central antenna in a $TM_{010}$ resonant cavity is usually quite small in diameter as compared to the diameter of the cavity, so the point of maximum field intensity can be considered to be the central axis of the oven. However, the electric field intensity is actually highest at the surface of the antenna. In the oven 183, R(z) and Ro(z) are measured from the surface of the antenna 330 rather than from the central axis of the cavity at least at those axial points z where the antenna is present. As the diameter of the antenna 330 varies over its length, so too do R(z), Ro(z), and R(z)/Ro(z). R(z)/Ro(z) is smallest and microwave energy absorption highest in the column heating element 130 where the diameter of the antenna 330 is largest and vice-versa. By varying the diameter of the antenna 330 along its length, the temperature profile of the column in the column heating element 130 is also altered at least over the length of the antenna 330.

If the diameter of the antenna 330 is large with respect to the center conductor of the coaxial connector 220 where it passes through the end cap 200 and enters the resonant cavity, as shown in FIG. 30, then an impedance matching section 340 similar to the impedance matching sections 85 in FIG. 15 may be used to more gradually adjust the diameters of the inner and outer conductors before entering the cavity.

Figure 31:
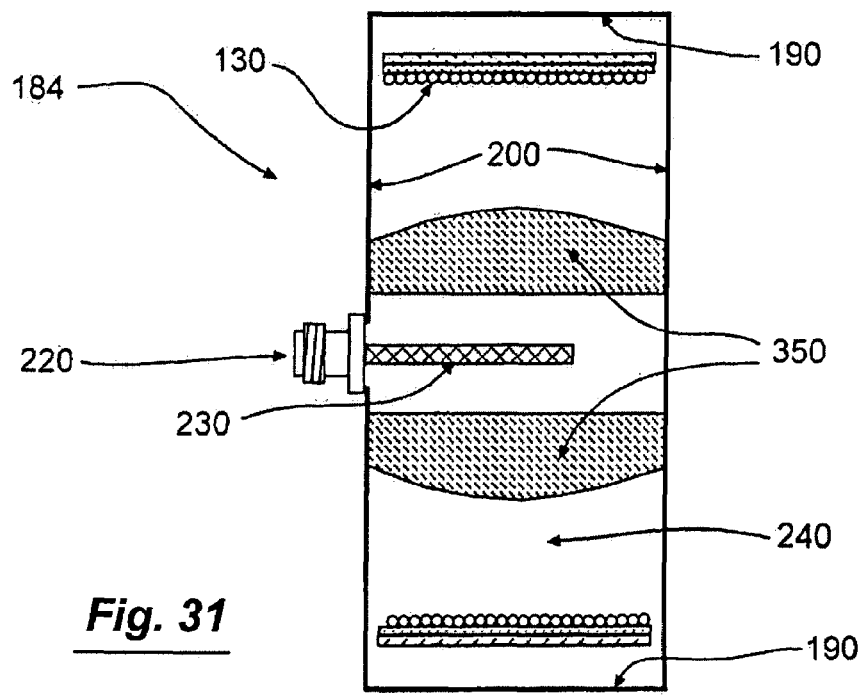
FIG. 31 is a cross-sectional view along the central axis of a chromatographic column microwave oven having a cylindrical resonant cavity in which the diameter of dielectric insert varies axially.

Varying the thickness of a cylindrical dielectric insert along its length in a chromatographic column microwave oven alters the rate of microwave absorption along the length of a column heating element in the oven. FIG. 31 shows the cross-sectional view of a chromatographic column microwave oven 184 along its central axis having all of the same elements as the oven 180 shown in FIG. 24, except the dielectric 250 is replaced with a dielectric 360 having a thickness that varies along its length.

The effective radii R(z) of a column heating element 130 and Ro(z) of a cavity wall 190 differ from the physical radii if the dielectric constant varies from the center of the cavity and out as it does when a dielectric insert is used. The electric field strength will decrease more through a given thickness of dielectric material in oven 184 than through an equivalent thickness of air or vacuum because its dielectric constant is higher. Thus, when a dielectric cylinder is used, Ro(z) and R(z) are greater than the physical lengths. If d(z) is the thickness of the dielectric 360 at a point z along its length, then the effective electrical radii of the column heating element 130 and the metal cylinder 190 depend on d(z) as well as z (i.e., R(z,d(z)) and Ro(z,d(z)) respectively). This effect was ignored when describing the oven embodiments 181, 182, and 183 because the thickness of dielectric 250 did not vary along its length. By varying the thickness of dielectric 360 along its length, the temperature profile of the column in column heating element 130 is similarly altered.

FIGS. 28–31 show different oven embodiments in which the geometry of one of the elements is varied axially to adjust the axial distribution of microwave absorption in the respective column heating elements. The specific curvature shown for each varied element in these figures levels out the rate of electric field absorption in a column heating element as compared to that in the oven 180 shown in FIGS. 24 and 25, for which the temperature profile is as shown in FIG. 26. The curvature is reversed if the column heating element absorbs more energy from the magnetic field than from the electric field because the magnetic field strength in $TM_{010}$ resonators increases from a minimum at the center of the cavity to a maximum at the outer cylindrical boundary. This is the opposite of the electric field which decreases from a maximum at the center of the cavity to a minimum at the outer cylindrical boundary.

There is one other way to alter the rate of microwave energy absorption of the column heating element along its length. The rate of power absorption of a point in the column heating element is a function of the electromagnetic field strength and of the loss factor of the column heating element. The specific relationship is described by the following equation:

$$P_{av} = \omega \epsilon_0 \epsilon''_{eff} E_{rms}^2 + \omega \mu_0 \mu''_{eff} H_{rms}^2 \quad (5)$$

where: $\omega$ is the angular frequency of the electromagnetic radiation, $\epsilon_0$ is the permittivity of free space, $\epsilon''_{eff}$ is the dielectric loss factor, $E_{rms}$ is the rms electric field strength, $\mu_0$ is the permeability of free space, $\mu''_{eff}$ is the magnetic loss factor, and $H_{rms}$ is the rms magnetic field strength.

By varying the dielectric or magnetic loss factor of a column heating element along the its length such that one has $\epsilon''_{eff}(z)$ or $\mu''_{eff}(z)$, the axial power absorption and the resulting temperature profile of the column in the column heating element are similarly altered. It may not be practical to achieve perfect isothermal conditions along the length of a chromatographic column assembly in a microwave oven owing to the interaction of the microwave absorbing material and the electromagnetic field. However, temperature variations can certainly be minimized such that conditions substantially equivalent to isothermal conditions are achieved.

The usage of thermally conductive material within the column heating element can help redistribute thermal energy if there are variations in temperature within the column heating element. Thus, thermally conductive material can be used to augment and improve the effectiveness of the various methods described herein for controlling the rate of microwave energy absorption throughout a column heating element. Thermally conductive material used in a column heating elements in chromatographic column microwave oven must not be electrically conductive or it will disrupt the proper operation of the oven.

Figure 32:
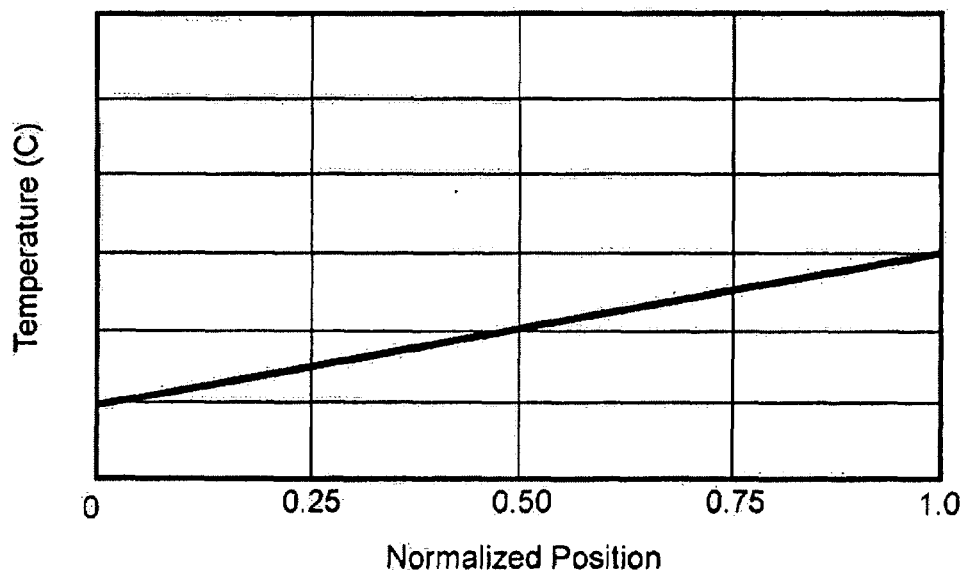
FIG. 32 is a graph showing a linearly increasing column temperature profile.
Figure 33:
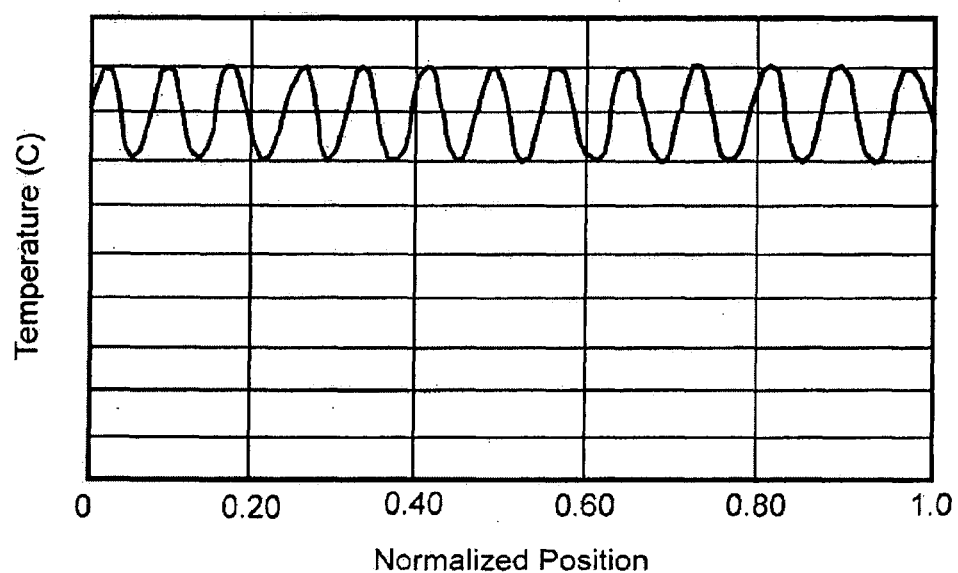
FIG. 33 is a graph showing a periodic column temperature profile.

Isothermal temperature profiles are usually used in chromatographic analyses. In fact, no other profile is used within the large resistively heated ovens used in most gas chromatographs. However, other temperature profiles can be achieved within the chromatographic column microwave ovens taught herein. For example, a microwave oven could be designed utilizing the methods and apparatus taught herein to achieve a linear temperature profile in a chromatographic column as illustrated in FIG. 32. Another useful temperature column profile that can be readily obtained with the microwave ovens described herein but which cannot be achieved in existing chromatographic column ovens is a periodically varying profile such as that shown in FIG. 33.

A periodically varying column temperature profile can improve the separation of components having small retention time differences because these components can pass many times through a temperature zone critical to separation during a single analysis. In a standard chromatographic oven using conventional temperature ramping programs, the critical temperature zone can only be passed through one time. Consider two compounds for which R1 represents the retention time of a first compound in a given chromatographic column and R2 represents the retention time of a second compound. Assume, that the boiling point of the first compound is higher than that of the second compound. The ratio of retention times of the two compounds R1/R2 forms the basis for their separation. At temperatures well above and well below the boiling points for the two compounds, the ratio R1/R2 is essentially one, so that no separation occurs. As the temperature of the column is increased from a cold point, the value of R1/R2 will increase until reaching a maximum at the temperature at which the compounds can most readily be separated and resolved. When a column has a periodic temperature profile, the compounds pass through the temperature corresponding to the maximum value of R1/R2 many times during a single analysis instead of just once, thereby improving separation and resolution.

All of the methods described herein to alter the axial microwave absorption distribution of a column heating element can be used to engineer a specific temperature profile along a chromatographic column including essentially isothermal, linear, or periodic profiles.

Figure 34:
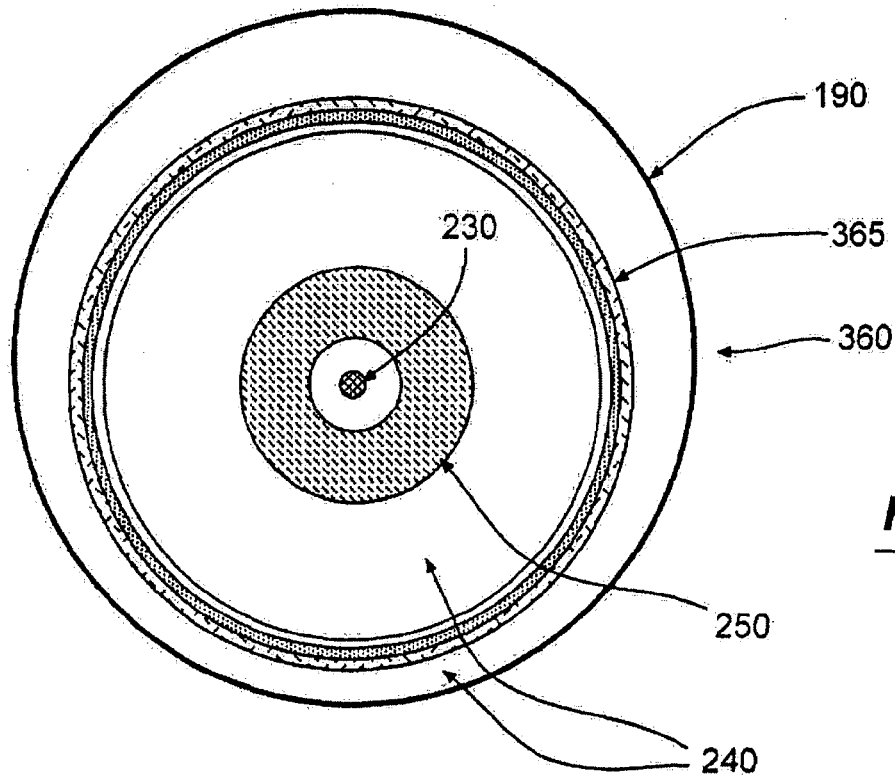
FIG. 34 is a radial cross-sectional view of a chromatographic column microwave oven wherein the column heating element is positioned off center within the oven in order to establish a periodic column temperature profile.

There are several other simple methods with which a periodic column temperature profile can be achieved in a microwave oven as taught herein. One method is to physically offset an element of the chromatographic column microwave oven from the center of the oven in order to displace the central axis of the column heating element from the central axis of the electromagnetic field. FIG. 34 shows the radial cross section of an embodiment of a chromatographic column microwave oven 360 in which the column heating element 365 has been offset from the geometric center of the oven. Such an offset will result in a temperature profile along each column coil in the heating element 360. This temperature profile will be repeated in each subsequent coil resulting in an overall periodic column temperature profile. A similar effect would be achieved if the column heating element is positioned symmetrically about the geometric center of the oven but the antenna 230 is moved off center, or the dielectric insert 250 is moved off center, or if some other object is placed off center within the oven so as to disturb the symmetry of the oven and thereby displace the center of the electromagnetic field from the central axis of the column heating element.

Figure 35:
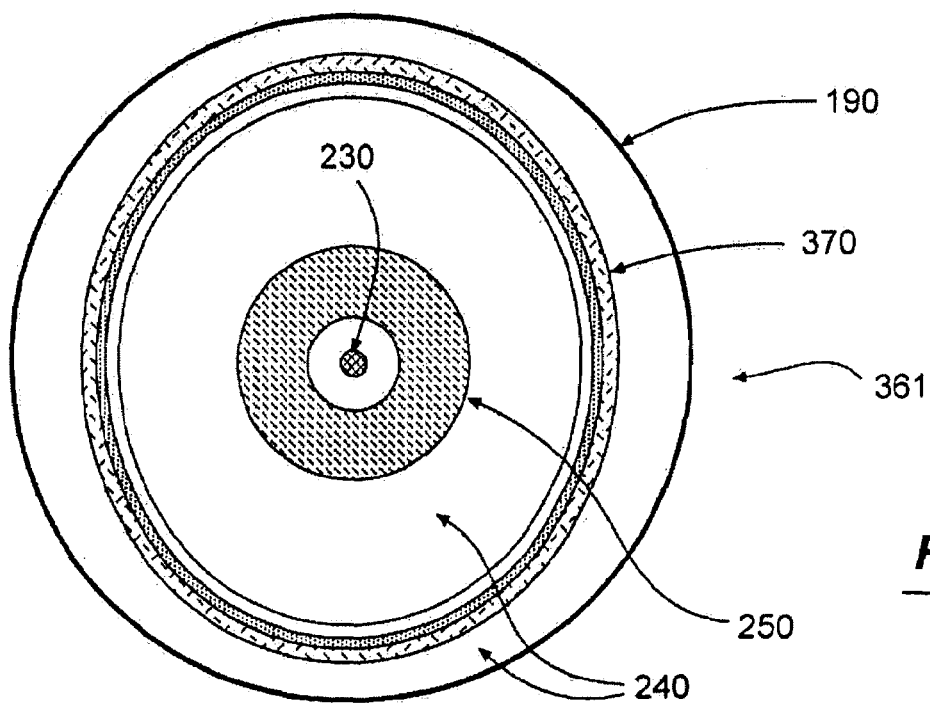
FIG. 35 is a radial cross-sectional view of a chromatographic column microwave oven wherein the column heating element has a different shape than does the oven in order to establish a periodic column temperature profile.

A second method for establishing a periodic column temperature profile is to alter the cross-sectional shape of the column heating element with respect to that of the oven so that individual coils do not trace isofield lines within the oven but rather oscillate about such lines resulting in a periodic column temperature profile. FIG. 35 shows the radial cross section of an embodiment of such a chromatographic column microwave oven 361 in which the column heating element 370 has an oval cross section while the oven walls 190 have a circular cross section. The same effect is achieved if the heating element 370 has a circular cross-section while the oven wall 190 or the dielectric insert 250 has a non-circular cross-section.

A last method for generating a periodic column temperature profile in a column heating element is to radially vary the electrical or thermal properties of the heating element so as to radially vary the heating rate that occurs in the heating element and thereby induce a periodically varying column temperature profile.

Using the chromatographic column microwave ovens taught herein, the column temperature profile can be engineered to optimize the quality of the chromatographic analyses. It should be clear that the column temperature profiles that can be established are not limited to those specifically described. Many other profiles can be created using the present invention.

Common Elements of the Chromatographic Column Microwave Oven Embodiments

A number of chromatographic column microwave oven embodiments have been described heretofore in this invention including coaxial microwave ovens and circular cylindrical resonant cavity ovens. Each of these oven embodiments may require implementation of at least one of the techniques taught for modifying the axial electromagnetic field gradient to make it a practical and useable chromatographic column microwave oven. There are certain common characteristics of useful chromatographic column microwave ovens as taught in this invention with which controlled column temperature profiles can be achieved: (1) Each oven is a single mode structure. Multiple modes and the uncertain electromagnetic field distribution that result therefrom are avoided. (2) The cross sectional geometry of each oven about its central axis results in an electromagnetic field distribution characterized by smoothly varying, continuous isofield lines oriented about an axis which is typically collinear with the geometric central axis of the oven. A chromatographic column coiled in a column heating element which traces these isofield lines is thus exposed to an electromagnetic field strength that is constant over the length of each individual column coil. Consequently, each such coil absorbs microwave energy at substantially the same rate at all points along its length. Each single chromatographic column coil is thus an isotherm or very nearly so given the small change in axial position between adjacent coils. Similarly, a column heating element that is placed in the oven in such a way that each coil of column traces a line which oscillates about the isofield lines is exposed to a periodically varying electromagnetic field strength that results in an oscillatory column temperature profile.

Figure 36:
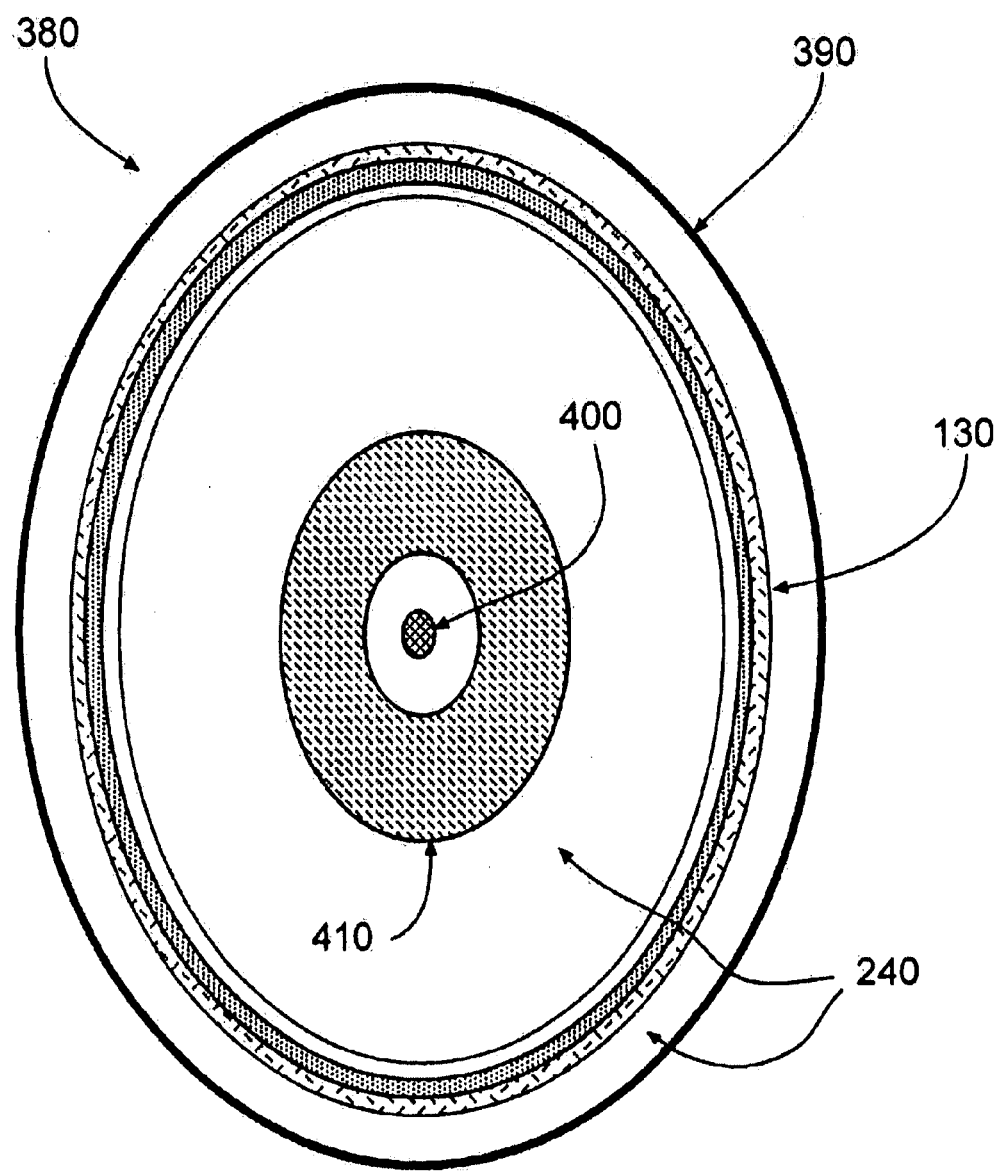
FIG. 36 is a cross-sectional view along the central axis of a chromatographic column microwave oven having an elliptical shape rather than a cylindrical shape.

All of the chromatographic column ovens described heretofore have circular cross sections perpendicular to the central axis as have the associated column heating elements. It is certainly possible to deviate from a circular structure and still have each column coil be an isotherm. A column coil will be an isotherm if it follows an isofield line in the oven. FIG. 36 shows the cross section of an elliptical chromatographic column oven 380 perpendicular to its central axis wherein the outer metal enclosure 390, the optional dielectric 410, and the antenna 400 are all elliptical. The electromagnetic field lines within the oven 380 will tend to follow the elliptical shape of the metal enclosure 390. As the column heating element 130 is elliptical, each column coil within the heating element 130 will still be an isotherm It should be understood that the present invention incorporates all chromatographic column microwave oven structures within which individual column coils either: (a) closely follow isofield lines within the oven such that the temperature varies little along the length of each column coil; or (b) oscillate about such isofield lines within the oven such that the temperature varies periodically along the length of the column coils.

(3) To achieve the desired chromatographic column temperature profile in a microwave oven, the electromagnetic field gradient from one coil of the column in the column heating element to the next must be sufficient to achieve the desired temperature difference from one coil to the next. If conditions approaching isothermal conditions are desired in the column, then the rate of microwave absorption must be substantially equal over the whole length of the column. To achieve this, the oven must be constructed using the techniques taught in this patent to expose the column heating element to the appropriate electromagnetic field strength along its length.

Compact Chromatographic Column Microwave Oven

As noted previously, chromatographic columns are very small—having diameters as little as 0.1 mm. All chromatographic column microwave oven embodiments described heretofore heat thin, cylindrical column heating elements which can be treated as two dimensional surfaces over which desired temperature conditions are established. These heating elements are thin because the column itself has a small diameter and because the column coil is only one or at most a few column layers in thickness. Problems associated with slow thermal conductivity in insulating materials are minimized with such column heating elements. However, even smaller microwave ovens can be constructed if the chromatographic column is bundled more tightly together or etched into a rigid substrate such as silicon.

Radiative heat loss from the chromatographic column during the heating cycle can be greatly reduced by providing the oven cavity with an infrared-reflective interior surface. For example, the interior surface of the cavity can be made of polished aluminum or steel.

Figure 37:
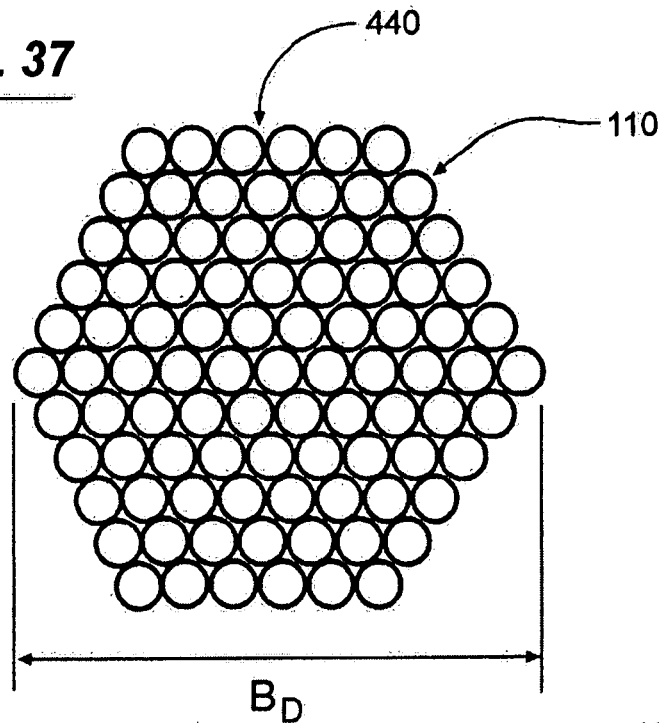
FIG. 37 is the cross-sectional view of a tightly bundled coil of chromatographic column.
Figure 38:
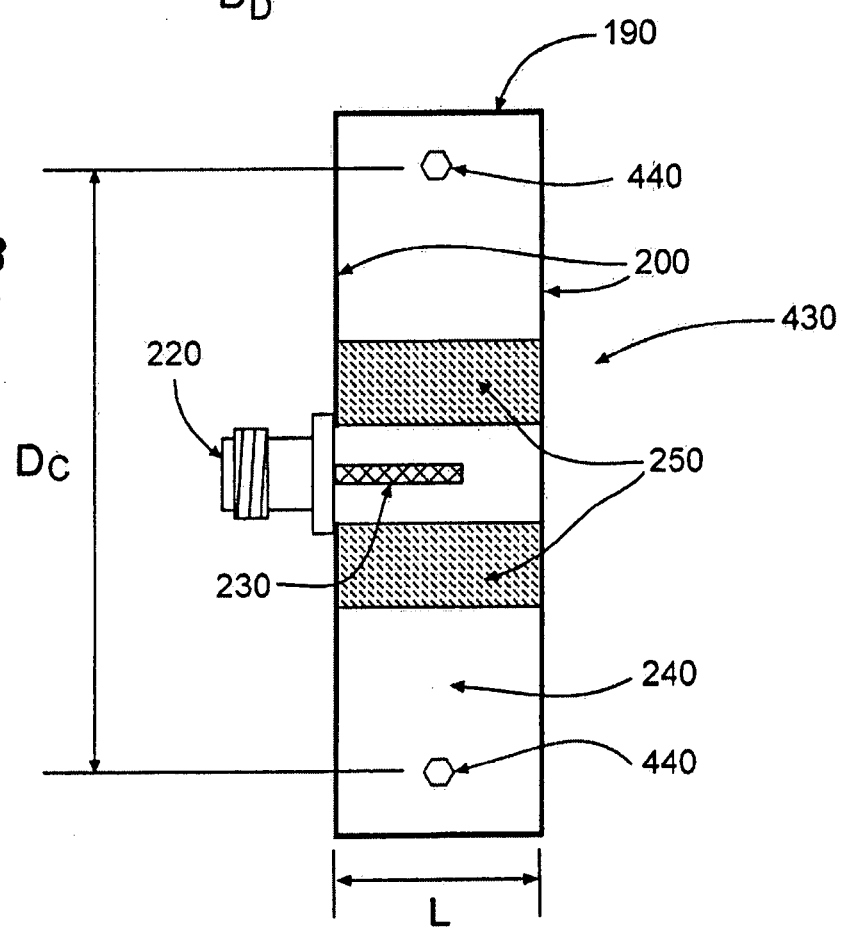
FIG. 38 is a cross-sectional view along the central axis of a compact chromatographic column microwave oven.

FIG. 37 shows the cross section of a chromatographic column 110 tightly packed into a coiled chromatographic column bundle 440 where the diameter of the filament bundle is denoted $B_D$. When packed in this manner, a 50 m long 0.32 mm diameter column coiled into loops 12.5 cm in diameter can be packed into a bundle for which $B_D$ is approximately 4.1 mm. FIG. 38 shows the cross section of a chromatographic column microwave oven 430 along its central axis in which a column bundle 440 having a major diameter $D_C$ is heated. The oven 430 has the same components as does the oven 180 shown in FIGS. 24 and 25 except for the substitution of column bundle 440 for column heating element 130. Column bundle 440 must contain microwave absorbing material if it is to absorb microwave energy and be heated in the oven 430. This microwave absorbing material can be incorporated into the column 110 itself, or dispersed within the column bundle 440 adjacent to the column 110.

Because $B_D$ is so small, the length L of oven 430 can be smaller than is possible with the other oven embodiments described in this invention. The axial length of the heating section could be as small as 5 to 10 mm though the diameter would still be at least several centimeters.

Though $B_D$ of a column bundle 440 is very small, the electromagnetic field strength to which it is exposed in the oven 430 will still vary over its cross section unless its loss factor is so small as to make it impractical for microwave heating purposes. Consequently, there will be variation in the rate at which microwave energy is absorbed in a column bundle 440 and the temperature will vary along the length of column 110. This variation cannot be corrected by changing the geometry of the oven 430.

Because the filament 440 is as small as it is, thermal energy redistributes itself relatively quickly to establish a thermal equilibrium approaching isothermal conditions. Carrier gas flowing within the column 110 further helps to redistribute heat within the bundle 440. Adding thermally conductive material to the column bundle 440 will accelerate the rate at which thermal equilibrium is reached and ensure that the equilibrium approaches isothermal conditions as closely as possible. While it may not be possible to achieve true isothermal conditions in the chromatographic column microwave oven 430, it is physically the most compact oven embodiment using commercially available capillary columns taught in this invention.

Connecting the Column Ends to the Injector and Detector

To incorporate the chromatographic column microwave oven embodiments taught herein into the rest of a gas chromatograph, the ends of the column must be connected to the injector and detector assemblies respectively, neither of which is conveniently placed in the microwave oven. These column ends must be kept at a temperature at least as high as the bulk of the column being heated in the microwave oven to prevent cold spots which, if present, severely degrade the performance of the GC. The injector and detectors themselves are maintained at temperatures above that of most of the column.

Figure 39:
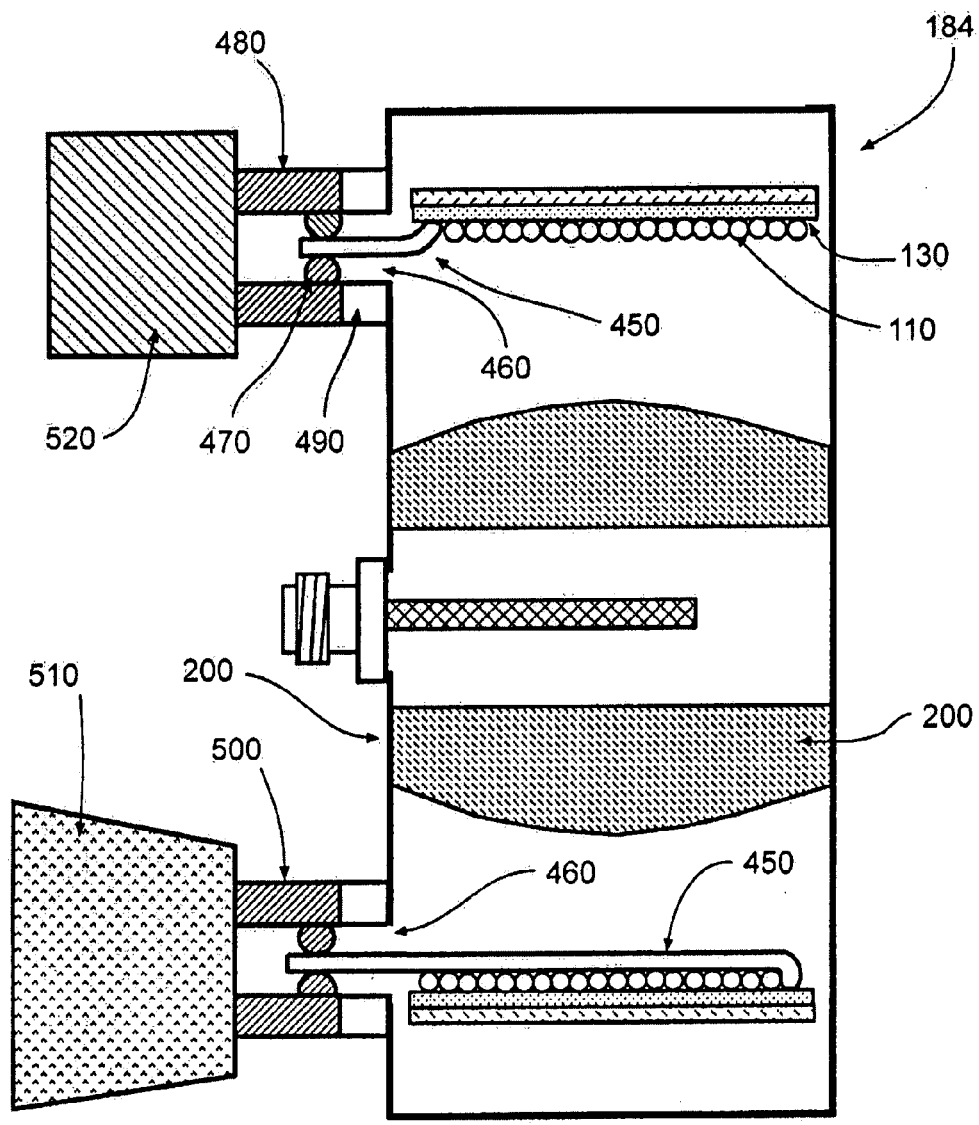
FIG. 39 is a cross-sectional view along the central axis of a chromatographic column microwave oven illustrating how the ends of the chromatographic column are connected into the injector and detector assemblies.

FIG. 39 shows how the chromatographic column microwave oven 184 can be incorporated into a chromatograph without inducing cold spots. The column ends 450 of the column 110 leave the microwave oven 184 through the holes 460 in the metal end cap 200 and enter the adapters 500. The adapters 500 provide mechanical connections between the chromatographic column microwave oven 184 and the injector 510 and the detector 520 respectively Each adapter 500 consists of: (1) a metal fitting 480 which is kept in intimate thermal contact with the injector 510 or the detector 520 housings; (2) a chromatographic column ferrule seal 470 which fits tightly within the metal fitting 480 and through which the column end 450 protrude; and (3) a thermal insulator fitting 490 which fits tightly between the metal fitting 480 and the end cap 200. The ferrule seal 470 is kept in thermal contact with the metal housing 480 so that it is essentially the same temperature as the injector 510 or the detector 520 respectively. The column ends 450 should not come into physical contact with any parts between the ferrule seal 470 and the column heating element 130 as any such parts are likely to be colder than the column ends 450 and therefore will conduct heat away from the column ends 450 creating cold spots in the column. The insulator fitting 490 slows the flow of heat from the metal fitting 480 to the end cap 200. Excess heat in the end cap 200 can slow the cooling rate of the oven 184 after the heating cycle is completed.

The interior of the oven 184 should be vacuum tight. The ferrule seal 470 is used as a vacuum seal on the exterior of both the column ends 450. Thus, the interior of the column 110 is not depressurized and the carrier gas and sample to be analyzed can pass freely through the column 110 from the injector 510 to the detector 520. The ferrule seal 470 is vacuum sealed to the metal fitting 480 which in turn is vacuum sealed to the insulator fitting 490. Finally, the insulator fitting 490 is vacuum sealed with the end cap 200. These different seals isolate the interior of the oven 184 from the injector 510 and the detector 520 and make it possible to operate the oven 184 in vacuum.

Figure 40:
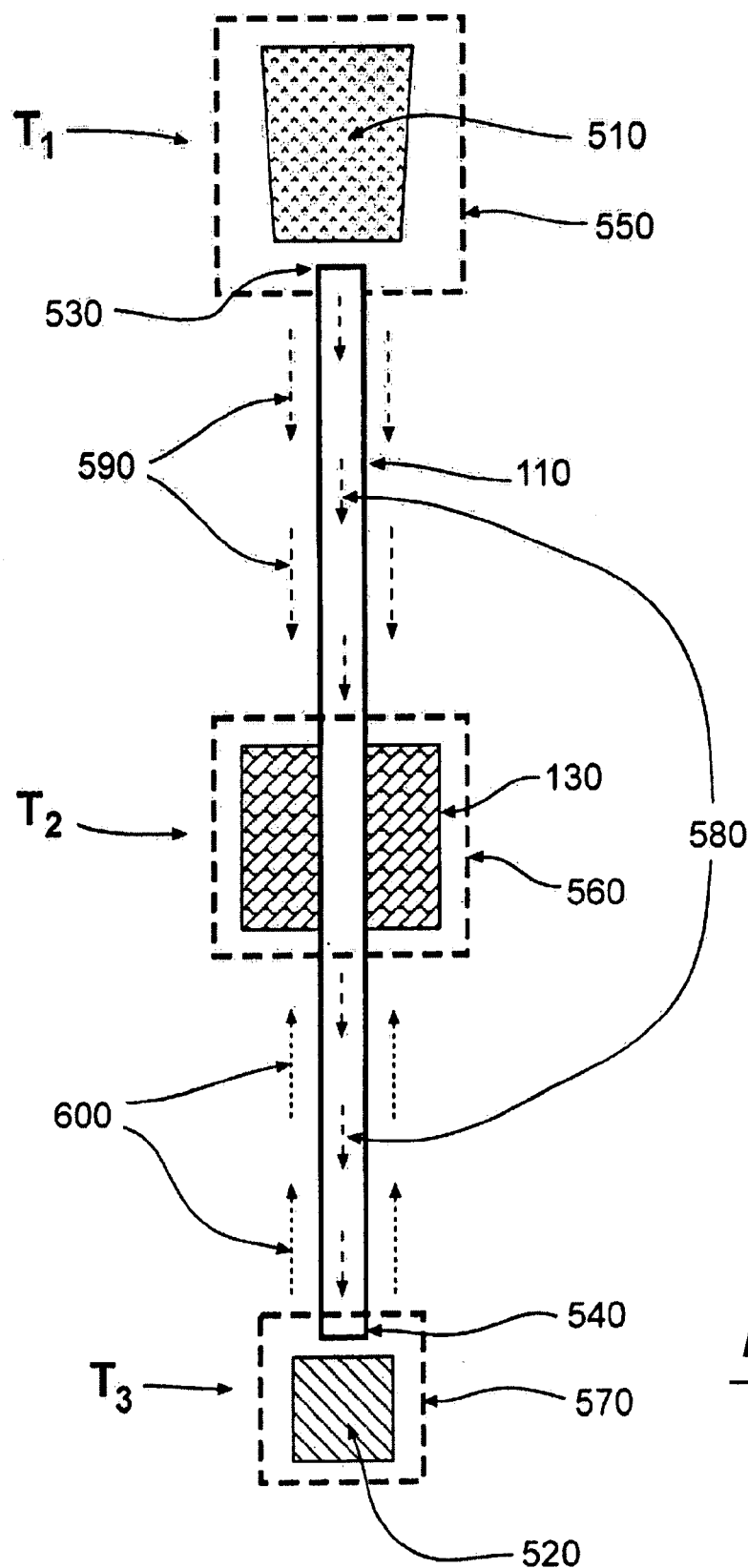
FIG. 40 is a diagram illustrating how the heat flows in the column within a microwave oven.

Several thermal processes occur within the structure illustrated in FIG. 39 that heat the column ends 450 while operating the chromatographic column microwave oven 184 even though the column ends 450 may not be heated directly by the column heating element 130. These processes are illustrated in FIG. 40.

Block 550 designates one isothermal region maintained at temperature T1. Block 550 includes the injector 510 and the proximal column end 530 of chromatographic column 110. Block 560 designates a second isothermal region (assuming an isothermal temperature profile for this description) having a temperature T2. Block 560 includes the column heating element 130. Block 570 designates a third isothermal region maintained at temperature T3. Block 570 includes the detector 520 and the distal column end 540 of chromatographic column 110. In a typical chromatography application, the detector 520 is kept hotter than the injector 510 which in turn is kept hotter than most of the chromatographic column 110, giving T3>T1>T2.

Thermal conduction and convection processes transfer thermal energy to those lengths of column 110 not heated directly in the blocks 550, 560, or 570. These processes are significantly more efficient if the chromatographic column microwave oven is operated in vacuum conditions.

Conduction

The thermal energy 590 is conducted along the walls of the column 110 from the block 550 to the block 560 because T1 is greater than T2. A similar flow of thermal energy 600 is conducted from the block 570 to the block 560 in the walls of the column 110. The thermal conduction processes 590 and 600 are very slow unless the column 110 includes a thermally conductive material to improve the thermal transfer rate.

Convection

A significantly faster heating mechanism for the column ends than direct conduction is convection from the carrier gas 580 flowing in the column 110. The carrier gas 580 flowing into the column 110 from the injector 510 will be the same temperature as the injector—T1. The flowing carrier gas stream 580 rapidly heats the length of column 110 lying between the isothermal blocks 550 and 560. Once the carrier gas stream 580 reaches the isothermal block 560, it rapidly comes to an equilibrium temperature of T2. The carrier gas stream 580 flowing from the block 560 rapidly heats the length of column 110 lying between the isothermal blocks 560 and 570. If the lengths of the column 110 between the isothermal blocks 550 and 560 and between the blocks 560 and 570 respectively are surrounded by relatively cool air, most of the thermal energy in the column will be lost to the air and the column ends will not be heated significantly by the described conduction and convection processes. This is yet another reason for operating the chromatographic column microwave ovens taught herein in vacuum conditions.

Figure 41:
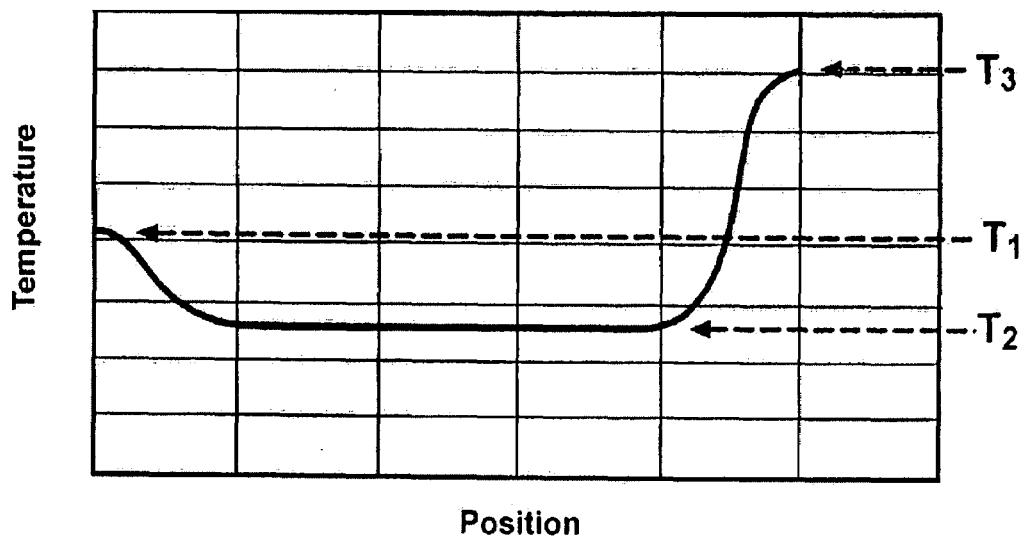
FIG. 41 is a graph illustrating the end-to-end temperature profile along a column heated within a microwave oven.

At thermal equilibrium, the temperature profile established along the entire length of the column 110 in a chromatographic column microwave oven as taught herein is similar to that established along a column in a conventional chromatographic oven. The profile is illustrated in the graph shown in FIG. 41 in which the x-axis represents the position along the length of the column 110 and the y-axis represents the column temperature. The x-axis is not to scale as the relative length of the column maintained at T2 would typically be much longer than the rest of the column. Starting from the left side of the graph, the temperature of the proximal end of the column 110 is equal to T1 which is the temperature of the injector 510. Moving to the right, the temperature of the column 110 drops to a temperature of T2 which is the temperature of the column heating element 130. The temperature of the column 110 is equal to T2 through the whole of the column heating element 130. After the column heating element 130, the temperature of the column 110 increases to a temperature at its distal end of T3 which is the temperature of the detector 520. Along the whole length of the column 110, there are no cold spots at which the temperature drops below T2.

Maximizing Thermal Efficiency in the Oven

The total amount of thermal energy that a chromatographic column oven needs to supply to a column heating element to attain a desired temperature is described by the following equation:

$$P_{TOT} = \Sigma M_i C_{pi} \Delta T/t + P_{CONV} + P_{COND} + P_{RAD} \tag{6}$$

where: $P_{TOT}$ is the total thermal power input of the oven, $M_i$ is the mass of each part 'i' in the oven that is to be heated, $C_{pi}$ is the specific heat of each part 'i', $\Delta T/t$ is the target rate of temperature increase per unit time, $P_{CONV}$ is the heat transferred from the heated parts of the oven to other parts and to the environment by convection processes.

$P_{COND}$ is the heat transferred from the heated parts of the oven to other parts and to the environment by direct thermal conduction mechanisms. $P_{RAD}$ is the heat transferred from the heated parts of the oven to other parts and to the environment by radiative processes.

As is clear from Eq. (6), the energy requirements of a chromatographic column oven can be minimized by: (1) minimizing the mass of the material that is heated so as to minimize the energy required to increase its temperature and (2) minimizing the thermal energy losses from the heated portions of the oven. Direct microwave heating of an appropriately designed column heating element makes it possible to reduce the mass of the material to be heated to little more than that of a standard chromatographic column. Thus, a chromatographic column microwave oven can minimize the amount of power needed to heat up a column. To achieve maximum efficiency, thermal losses from the column heating element must also be minimized.

As described previously, thermal losses via convection are best minimized by removing most of the air from the interior of the chromatographic column microwave oven. Even a modest vacuum of 75 Torr will reduce convection losses by 90%.

Thermal conduction losses from the heated portion of the column heating element to the walls of the oven are easily reduced by properly designing the mechanical support assembly which holds the column heating element within the oven. The mechanical support should be constructed from materials which can withstand exposure to high temperature, have low thermal conductivity, do not absorb microwave energy appreciably, and which will not disturb the electromagnetic field distribution within the microwave oven. Appropriate materials include many ceramics such as aluminum oxide and high temperature plastics such a polyimide. In addition, the cross sectional area of the mechanical supports which physically connect the heated portion of the column heating element to the oven walls should be reduced as much as is practical to minimize the flow path through which thermal energy can conduct to the oven walls.

When thermal loss via convection and conduction have been reduced as described, radiative losses from the column heating element represent the most significant source of thermal loss from the column. Radiative losses from the column heating element are directly proportional to the surface area of the heating element and the emissivity of the material on the surface of the heating element. The surface area of the heating element is most easily reduced by wrapping the chromatographic column into a bundle as illustrated in FIG. 37 and utilized in oven 430 as shown in FIG. 38. Reducing the emissivity of the heating element is not very practical, however.

Emissivity is a unitless coefficient having a value between 0 and 1. It represents how much a given material radiates at a given temperature as compared to a perfect black body source which has an emissivity value of 1. Electrically non-conducting materials such as plastic and ceramic typically have emissivity values of 0.9 or greater. As these materials are the most suitable for usage in a column heating element in chromatographic column microwave oven, it is not practical to significantly reduce direct radiative losses of a column heating element by using materials with low emissivity values. However, radiative losses can be reduced indirectly.

Most radiation emitted from a hot column heating element will strike the interior surface of the metal walls of the microwave oven. Most metals have emissivity values less than 0.2 and so are poor emitters of thermally induced radiation. But they are good reflectors of this same radiation because the reflection coefficient for different materials is related to (1-emissivity). Consequently, most of the thermal energy radiated by a column heating element which strikes the metal walls of the oven is not absorbed by the walls but is reflected back into the oven. Thus, if the emissivity of the interior surface of the microwave oven walls is minimized, then the radiative loss from the column heating element will similarly be minimized because most of the energy radiated by the heating element will be internally reflected in the oven until it strikes a surface with a high emissivity value where it will be absorbed. Most thermal radiation emitted by the column heating element will find its way back to the column heating element. The bath of thermal radiation with the oven also helps heat the column ends.

The emissivity of the interior walls of the oven can be minimized by: (1) using a material with a low emissivity value such as aluminum, gold, copper or silver; and (2) by polishing the walls to reduce surface roughness. A well polished gold surface has an emissivity value of less than 0.02. The entire wall need not be made of a precious metal such as gold to achieve the desired effect. A thickness on only a few micrometers is sufficient.

When all of the measures are taken to reduce thermal losses, a high efficiency chromatographic column microwave oven is achieved. Less than 100 W of microwave power are required to maintain the temperature of a typical 60 m chromatographic column at 350° C. as compared to more than 1500 W with a typical resistively heated chromatographic oven. With so little energy to be dissipated, the walls of the oven do not get very warm even when uninsulated. This is a significant advantage as compared to other column heating methods.

Controlling the Microwave Source Used to Drive the Oven

Figure 42:
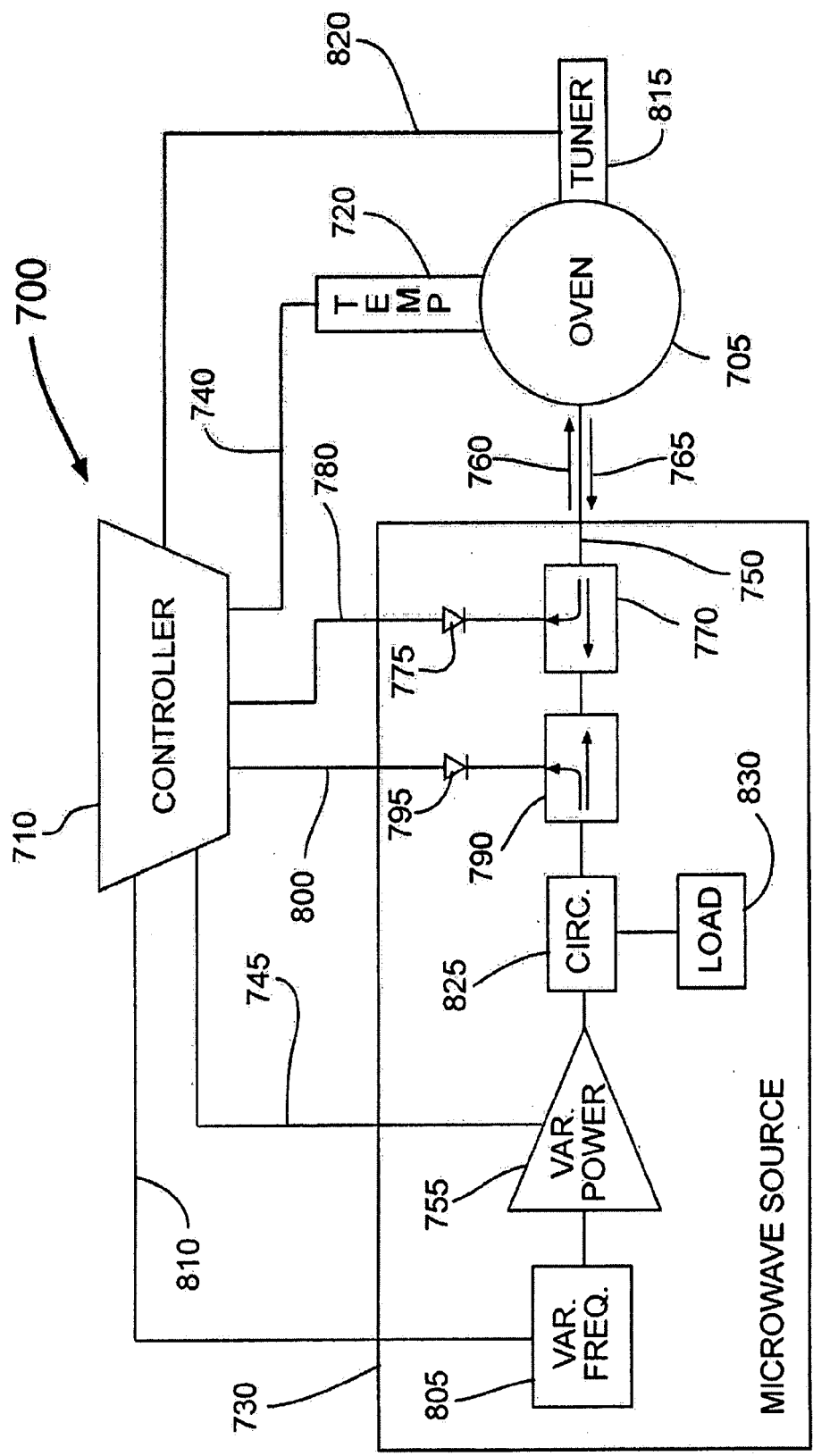
FIG. 42 shows an system which can control the temperature of a column in a chromatographic column microwave oven and which can control the efficiency of the microwave power source.

A chromatograph which includes a chromatographic column microwave oven must continuously control the temperature of the column heating element in the oven in order to generate useful temperature ramps. Continuous oven temperature control is achieved via control of the microwave source used to generate the microwave signal that is transmitted into the oven. FIG. 42 shows a system 700 capable of: (1) controlling how much microwave power is transmitted to a chromatographic column microwave oven; and (2) controlling the power efficiency of the microwave source. The main components of system 700 are a microwave oven 705, a controller 710, a temperature sensor 720, and a microwave source 730. The oven 705 is any microwave oven used to heat a chromatographic column. The controller 710 is understood to be any electronic system or computer capable of receiving input signals and generating output signals in response to the inputs in accordance with preprogrammed instructions. The temperature sensor 720 is any temperature measurement apparatus with which the temperature of the chromatographic column within oven 700 can be determined. The microwave source 730 is any microwave signal generator capable of producing enough microwave power to heat a chromatographic column in oven 705. For the purposes of this description, the microwave source 730 includes all components used to generate, amplify, attenuate, modulate, monitor, or otherwise alter the microwave signal transmitted to the oven 705.

The controller 710 is connected to the temperature sensor 720 by a signal line 740. The controller 710 is connected to the microwave source 730 by a signal line 745. The microwave source 730 generates and transmits a microwave power signal 760 to the oven 705 via a transmission line 750. The temperature sensor 720 measures the temperature within the oven 705 and transmits a corresponding signal to the controller 710 via signal line 740. If the temperature is too low, the controller 710 increases the microwave power signal 760 being transmitted to the oven 705 by adjusting a variable power element 755 within the microwave source 730 via control line 745. Similarly, if the temperature is too high, the microwave power signal 760 is correspondingly reduced. The variable power element 755 is any component by which the output power of the microwave source 730 can be adjusted, including but not limited to variable gain amplifiers, variable attenuators, and circuits which essentially turn the microwave power on and off such that the total microwave output power is modulated by controlling the duty cycle. Together, the controller 710, temperature sensor 720, and variable power element 755 comprise a closed temperature control loop.

Unless the oven 705 and microwave source 730 are tuned carefully, much of the microwave power signal 760 generated and transmitted by the microwave source 730 is reflected by the oven 705 back to the microwave source 730 where it is dissipated as useless heat. The reflected microwave signal 765 can even damage the microwave source 730. Various optional elements can be added to the system 700 to improve overall efficiency and prevent damage in the microwave source 730 caused by excessive reflected power.

As shown in FIG. 42, a directional coupler 770 couples a small portion of the reflected microwave signal 765 to a detector 775 which generates a signal indicating to the reflected power level. This signal is transmitted to a controller 710 by signal line 780. Similarly a directional coupler 790 samples a small portion of the microwave power signal 760 to the detector 795 which generates a signal related to the outgoing microwave power level. This signal is transmitted to the controller 710 by signal line 800. Given the signals from signal lines 780 and 800 indicative of the reflected and outgoing power levels respectively, the controller 710 can continuously determine how much microwave power is being transmitted into the oven 705 and how much is being reflected back to the microwave source 730.

The proportion of the microwave power reflected by the oven 705 is determined by how close the input impedance of the oven 705 matches the output impedance of the microwave source 730. The impedance match is primarily determined by the match between the microwave frequency generated by the microwave source 730 and the resonant frequency of the oven 705—the closer the respective frequencies, the less microwave energy is reflected by the oven 705. The resonant frequency of the oven 705 may vary with time. It may also vary with the temperature in the oven. Most importantly, it may vary with the type and size of the chromatographic column heated in the oven 705. By continuously varying the microwave frequency of the microwave source 730 to approximately match the resonant frequency of the oven 705, the efficiency of the microwave source 730 can be optimized. Two methods may be used to optimize efficiency and both are shown in FIG. 42.

Using the first efficiency optimization method, a controller 710 is connected to a variable frequency element 805 within the microwave source 730 by control line 810. The variable frequency element 805 is any component by which the frequency of the microwave source 730 can be varied including voltage controlled oscillators and mechanical tuning elements. The controller 710 varies the reflected microwave signal 765 by adjusting the variable frequency element 805 via the control line 810 until the reflected power signal measured on the signal line 780 is minimized, thereby indicating that the resonant frequency of the oven 705 matches the output frequency of the microwave source 730.

The second method for improving the efficiency of the system 700 is to tune the resonant frequency of the oven 705 to match the output frequency of the microwave source 730. Tuning the oven frequency can be performed using a tuning element added to the oven 705. As shown in FIG. 42, the controller 710 is connected to an oven tuning element 815 by control line 820. The oven tuning element 815 is any device capable of changing the resonant frequency of the oven 705 including, for example, a retractable metal pin protruding into the oven 705. Adjusting the length of the pin in the oven 705 adjusts the resonant frequency of the oven 705. The controller 710 varies the reflected microwave signal 765 by adjusting the oven tuning element 815 using the control line 820 until the reflected power signal measured on signal line 780 is minimized, thereby indicating that the resonant frequency of the oven 705 matches the output frequency of the microwave source 730.

Even with the reflected microwave signal 765 minimized, the microwave source 730 can be damaged or destroyed if the reflected microwave signal 765 is excessive. Damage to the microwave source 730 can be eliminated by including an optional circulator 825 in the microwave source 730 as shown in FIG. 42. The circulator 825 redirects most of the reflected microwave signal 765 into a matched load 830, which dissipates the reflected microwave signal 765.

Measuring the Temperature in the Oven

Measuring the temperature of a column in a chromatographic column microwave oven operated in vacuum conditions is more difficult than measuring the temperature of a conventional chromatographic oven. Most temperature measurement methods use: (1) a temperature sensor that is placed where it will come to thermal equilibrium with an object to be measured; and (2) metal wires to transmit information from the sensor to some remote electronics for processing. Such a configuration is problematic in a microwave oven because the metal wires can disturb the electromagnetic field within the oven and because they can act as undesirable antennas which transmit microwave radiation out of the oven. Such problems can be minimized if the signal lines from the temperature sensor run perpendicular to the electric field lines within the microwave oven. Metal wires perpendicular to the electromagnetic field lines in a microwave oven are essentially invisible to the electromagnetic field in the microwave oven. They do not disturb the field nor do they draw energy from it.

Figure 43:
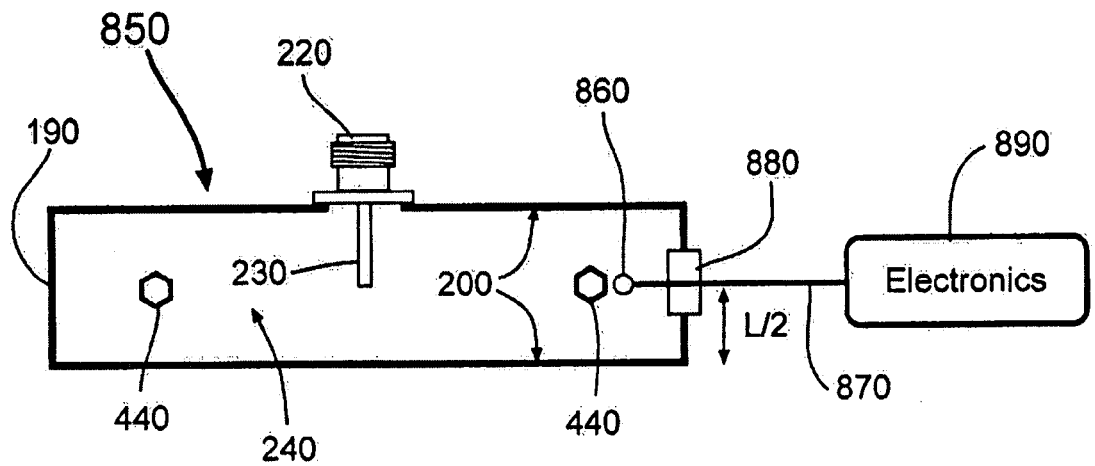
FIG. 43 is a cross-sectional view along the central axis of a chromatographic column microwave oven which utilizes a temperature sensor placed in thermal contact with the column heating assembly.

FIG. 43 shows the cross section of a chromatographic column microwave oven 850 along its central axis which utilizes a temperature sensor to measure the temperature of the column heating element 440. The oven 850 is identical to the oven 430 shown in FIG. 38 without an optional dielectric insert 250. The temperature sensor 860 is placed in contact with or in proximity to the column heating element 440 such that it is in thermal equilibrium with the column heating element 440. The temperature sensor 860 is any temperature measurement device such as a thermocouple or RTD for which proper operation requires that the measurement element must be at or near the same temperature as the object to be measured. One or more signal wires 870 transmit the signal from the temperature sensor 860 through an air tight connector 880 in the oven wall 190 to external electronics 890 for signal processing. The isofield lines in the oven 850 are circumferential as described by Eq. (4). Thus, the signal wires 860 should lie along a radial line in oven 850 so as to be perpendicular to the electric field lines. In addition, the signal lines 860 should be placed approximately halfway between the end caps 200 or at point L/2 along the side wall 190.

An alternative temperature measurement means is a non-contact, infrared temperature measurement device. An infrared temperature sensor measures the temperature of objects by analyzing the infrared radiation they give off. Such a measurement can be made remotely. Remote measurement is advantageous for a chromatographic column microwave oven because the temperature measurement means will not disturb the operation of the oven. Another advantage of infrared temperature measurement devices is that they have a faster response time than do temperature measurement means for which the temperature sensor must be in thermal equilibrium to make a measurement. A faster response time makes it easier to accurately control the temperature of a column heating element during fast temperature ramps.

Figure 44:
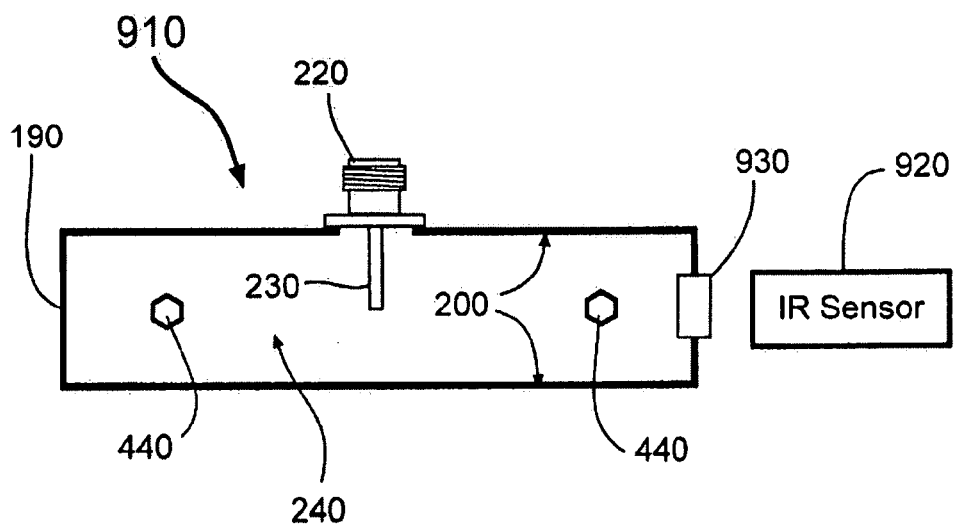
FIG. 44 is a cross-sectional view along the central axis of a chromatographic column microwave oven which utilizes an infrared temperature sensor placed outside the oven to measure the temperature of the column heating element.

FIG. 44 shows the cross section of a chromatographic column microwave oven 910 along its central axis which utilizes an infrared temperature sensor 920 to measure the temperature of column heating element 440. The oven 910 is identical to the oven 430 shown in FIG. 38 without the optional dielectric insert 250. The temperature sensor 920 is placed outside the oven 910. It is exposed to the infrared radiation given off by the column heating element 440 through an infrared transparent window 930 placed in the oven wall 190. Alternatively, the window could also be placed in one of the end caps 200. The window 930 should be sealed so that vacuum conditions can be maintained within the oven 910.

Cooling the Oven

A vacuum pump can be employed to pump the air out of the chromatographic column microwave oven so that the column heating element can be heated most efficiently. After a heating cycle has been completed, however, the column heating element must be cooled in preparation for a new analysis.

Column heating elements taught herein have low thermal mass. Similarly, chromatographic column microwave ovens taught herein are capable of high efficiency operation such that little thermal energy is dissipated into the oven itself. As a whole, very little thermal energy needs to be removed from such an oven and column heating element to cool them down. Conventional chromatographic ovens use large, high flow rate fans for cool down. Even so, they do not cool down very quickly because the ovens contain so much thermal energy. Conversely, the chromatographic column microwave ovens taught herein can be cooled rapidly with a modest flow of air. In fact, the vacuum pump itself can be used to cool the system.

Most vacuum pumps can be used to draw a steady flow rate of air when connected to the open atmosphere. Thus, to cool a chromatographic column microwave oven, the vacuum pump can be used to suck air through the oven rather than to pump air out of the oven.

Figure 45:
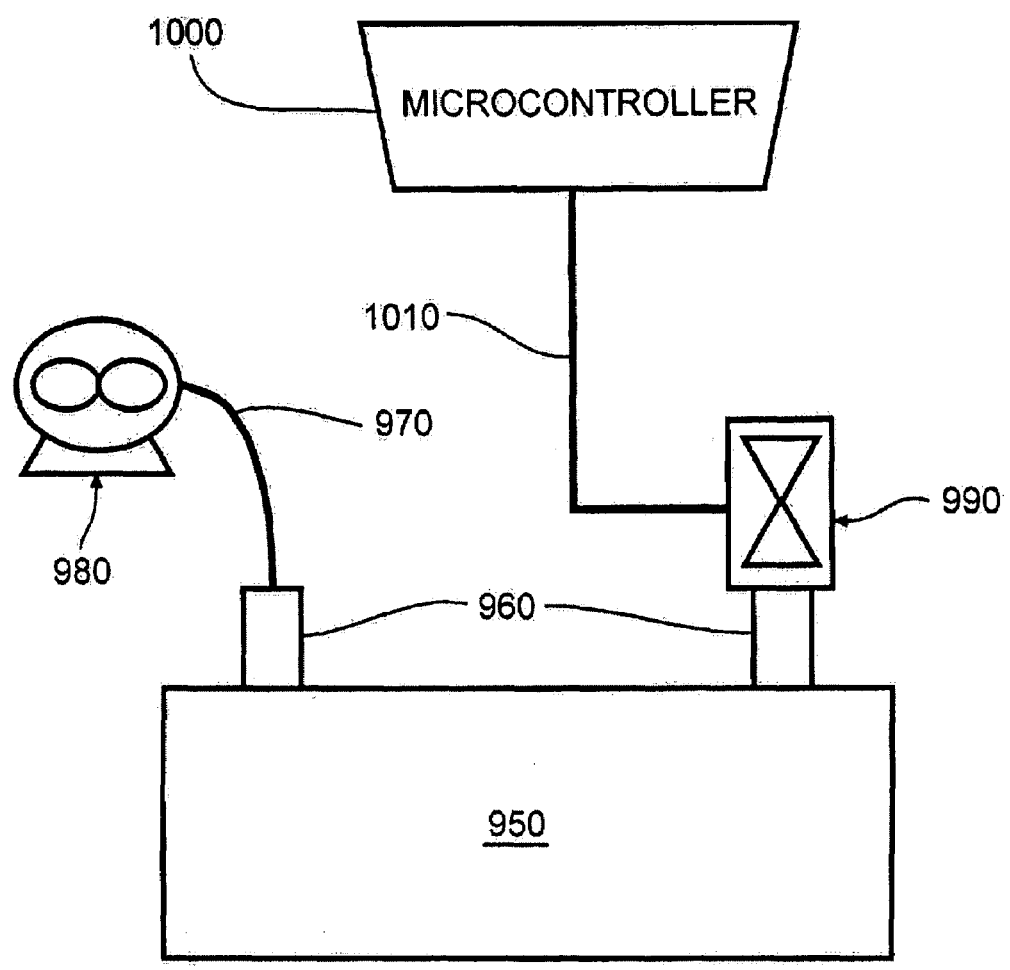
FIG. 45 shows a systems which utilizes a single vacuum pump to establish a vacuum in a chromatographic column microwave oven during a heating cycle and to cool the oven during a cooling cycle.

FIG. 45 illustrates a system utilizing one and the same vacuum pump to establish vacuum conditions during a heating cycle and to cool the oven down during a cooling cycle. The oven 950 is any oven built in accordance with the teaching of this invention. The oven 950 has two pneumatic ports 960 through which air can pass freely in and out of the oven. One port 960 is connected to an air hose 970 which in turn is connection to the vacuum pump 980. The second, inlet port 960 has a valve 990. When a vacuum condition is to be established in the oven 950, the valve 990 is closed and the vacuum pump 980 removes most of the air from the oven 950. When the oven 950 is to be cooled, the valve 990 is opened and the vacuum pump 980 draws air through the inlet port and oven 950 to remove thermal energy and thereby cool the chromatographic column. If the valve 990 is an electronic valve, it can be controlled automatically with a controller/computer 1000 via control line 1010 such that the heating and cooling cycles are fully coordinated with the other functions of the analytical instrument into which the oven system is built.

Preventing Plasma Formation in the Oven

It is possible to generate a plasma in a low pressure gas by exposing the gas to a high-strength electromagnetic field. Such a plasma can be induced in a chromatographic column microwave oven when operated in vacuum conditions because very high electromagnetic field strengths can be generated at the tip of the antenna used to transmit microwave energy into the oven. Such a plasma can be quite destructive as it can induce very high temperatures in the antenna. Consequently measures should be taken to prevent the formation of a plasma in a chromatographic column microwave oven.

Figure 46:
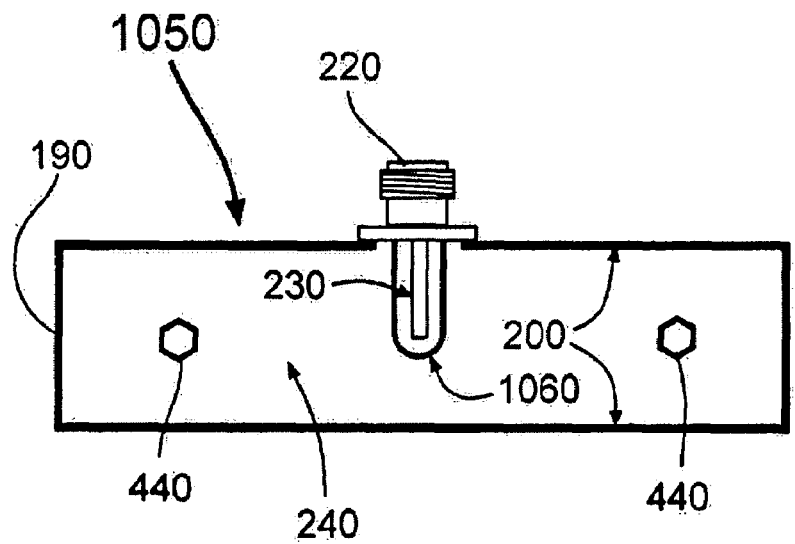
FIG. 46 is a cross-sectional view along the central axis of a chromatographic column microwave oven which utilizes a dielectric sheath on the antenna to prevent the formation of a plasma in the oven.

FIG. 46 shows the cross section of a chromatographic column microwave oven 1050 along its central axis built to prevent the formation of a plasma on antenna 230. The oven 1050 is identical to the oven 430 shown in FIG. 38, without an optional dielectric insert 250. The antenna 230 is covered at least in part with a dielectric sheath 1060 that isolates those portions of the antenna where the electromagnetic field strength is high enough to generate a plasma when vacuum conditions are present within the oven 1050. The dielectric sheath 1060 should be made of a material that is electrically non-conductive and does not absorb microwave energy, such as ceramic or polyimide.

Figure 47:
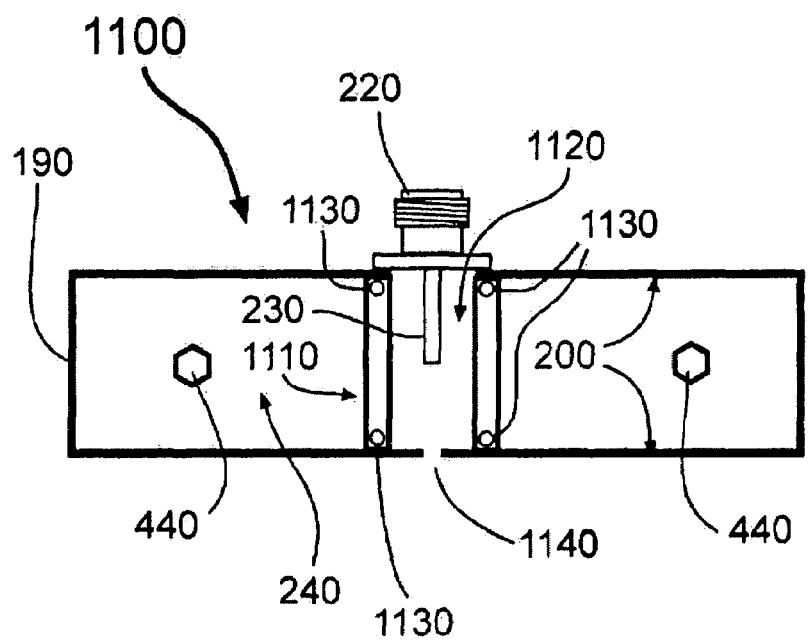
FIG. 47 is a cross-sectional view along the central axis of a chromatographic column microwave oven which utilizes a dielectric sleeve around the antenna to prevent the formation of a plasma in the oven.

FIG. 47 shows the cross section of a second chromatographic column microwave oven 1100 along its central axis built to prevent the formation of a plasma on the antenna 230. The oven 1100 is identical to the oven 430 shown in FIG. 38 without an optional dielectric insert 250. The oven 1100 contains a dielectric sleeve 1110 having an interior diameter larger than the outer diameter of antenna 230 such that there is a gap 1120 between the two. The dielectric sleeve 1110 can be a simple cylindrical tube as shown in FIG. 46 covering all or part of the antenna 230, or it could be a tube with one closed end and one open end. The dielectric sleeve 1110 should be made of a material that is electrically non-conductive and that does not absorb microwave energy such as ceramic or polyimide. The dielectric sleeve 1110 and dielectric insert 250 could be combined into a single part.

The dielectric sleeve 1110 has one or more vacuum seals 1130 to isolate the gap 1120 from the rest of the interior of oven 240. Atmospheric conditions can thus be maintained in the gap 1120 even when vacuum conditions exist elsewhere inside the oven 1100. Because the gas at the surface of antenna 230 is at atmospheric conditions and not vacuum conditions, no plasma is formed at the antenna 230 during operation. An added advantage of this oven 1100 is that air in the gap 1120 can help cool the antenna 230 and dielectric sleeve 1110 if they get hot. It is even possible to draw air through the gap 1120 to cool these parts if optional holes 1140 are opened up in the oven at either end of the dielectric sleeve 1110.

Transmitting Microwaves into the Oven

Figure 48:
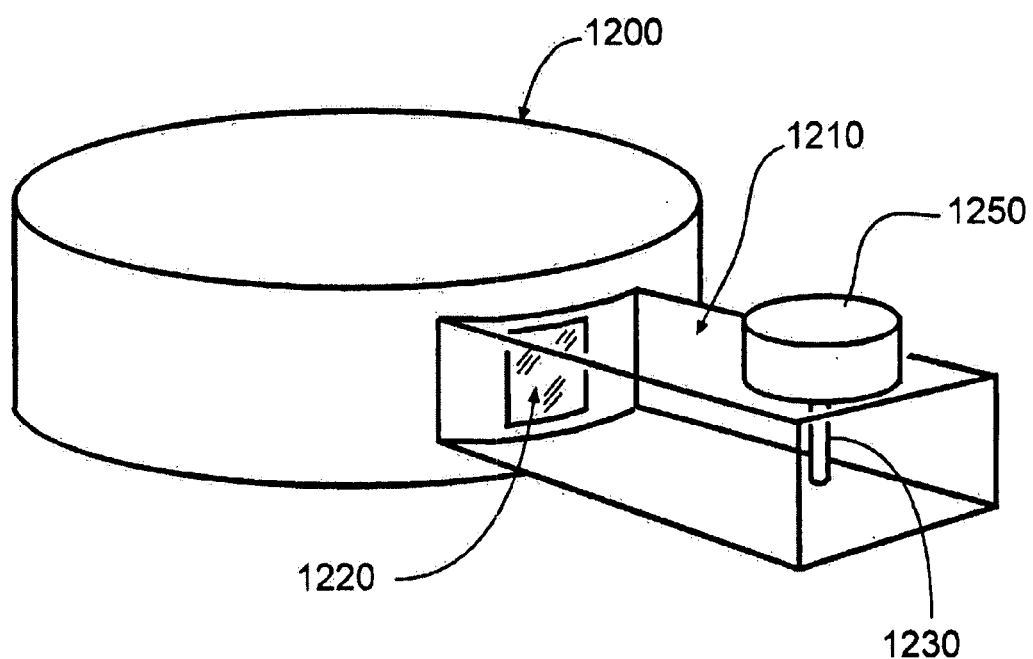
FIG. 48 shows a chromatographic column microwave oven which uses an aperture and waveguide transmitter to transmit microwave power into the oven rather than an antenna.

All chromatographic column microwave oven embodiments described herein use an antenna to transmit microwave energy directly into the oven. There are other types of transmitters by which microwave energy can be transmitted into the oven. For example, an aperture can be cut in the wall of the oven through which microwave energy can be transmitted from an external waveguide apparatus into the chromatographic microwave oven. FIG. 48 shows an external view of a chromatographic column microwave oven 1200 built with an aperture transmitter rather than an antenna transmitter. The oven 1200 can be any of the chromatographic column microwave ovens taught herein. A waveguide 1210 is connected to the external wall of oven 1200. An aperture 1220 is cut into the side wall of the oven 1200 such that electromagnetic energy propagating down the waveguide 1210 can be transmitted from the waveguide 1210 into the oven 1200 through the aperture 1220. The aperture 1220 can be an open hole or it may be a dielectric window through which electromagnetic waves can pass. Microwave energy is transmitted into the waveguide 1210 via an antenna 1230. Optionally, the antenna 1230 can be the launcher of a magnetron microwave source 1240.

Generally, any type of microwave transmitter mechanism can be used with the chromatographic column microwave ovens taught herein. The specific transmitter used to introduce microwave energy into a given oven is not a central feature of this invention.

Figure 49:
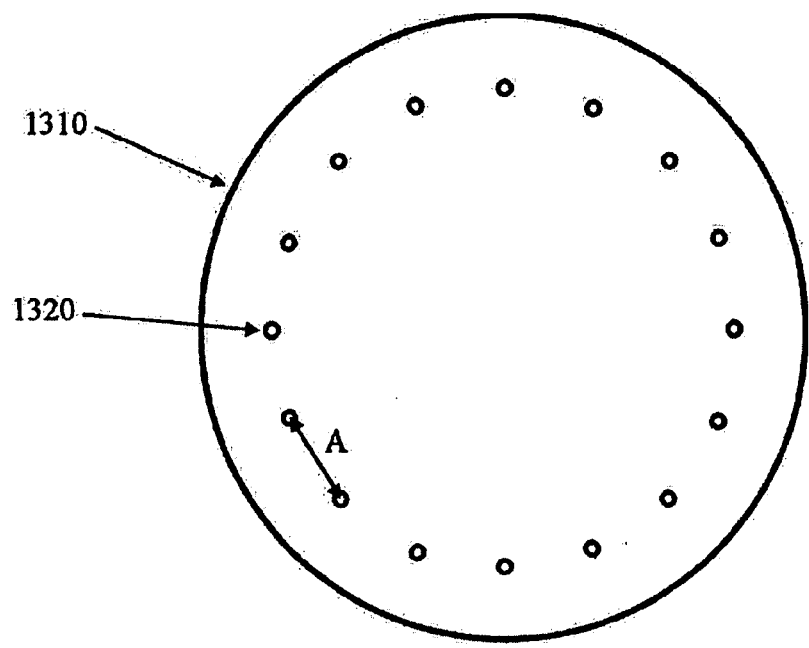
FIG. 49 shows an end cap with a large number of holes distributed symmetrically about its center.
Figure 50:
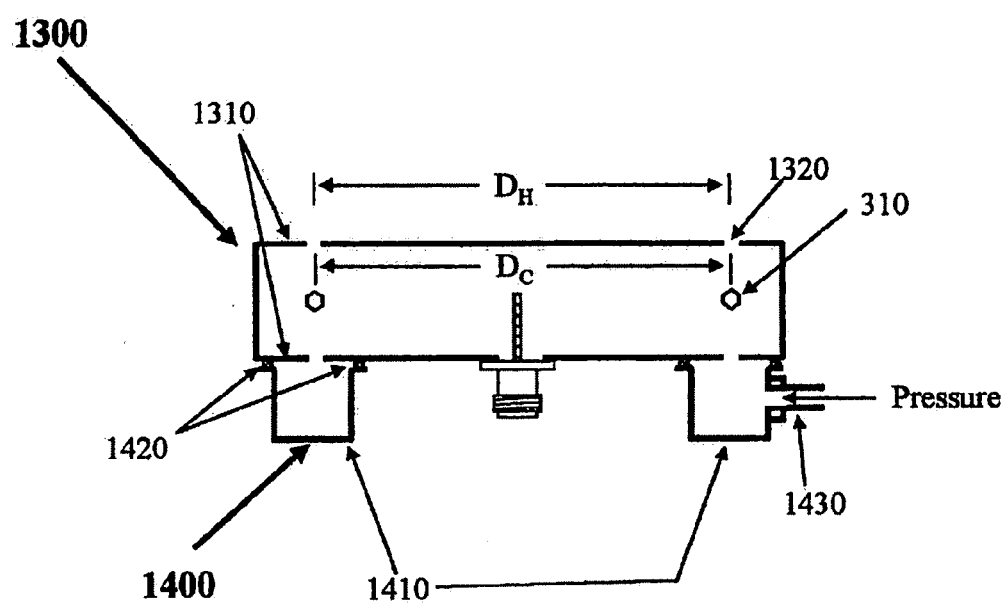
FIG. 50 is cross-sectional views along the central axis of chromatographic column microwave ovens in which the column heating bundle can be cooled rapidly and evenly.

FIG. 49 shows an end cap 1310 that is well suited for even cooling of a chromatographic column in a chromatographic column microwave oven. The end cap 1310 has numerous holes 1320 through it that are evenly spaced about the center of the end cap 1310. The distance between adjacent holes, A, should typically be no greater than three times the internal axial height of the oven in which the end cap 1310 is used. FIG. 50 shows the cross sections an oven 1300 and an air flow assembly 1400 along their central axes. The oven 1300 is identical to the oven 300 shown in FIG. 38, though it could be any oven built in accordance with the teaching of this invention, except that the two end caps 200 in oven 300 are replaced with the two end caps 1310.

The diameter $D_H$ of the circle of holes 1320 is essentially the same as the diameter $D_B$ of the column bundle (not shown) so as to force the air flowing axially through the oven 1300 to flow right past the column bundle (not shown). The air flow assembly 1400 is used to channel air to all of the holes 1320 in one end cap 1310. The air flow assembly 1400 includes a circular round channel 1410 (shown in cross section), two circular air tight seals 1420, and a pneumatic port 1430. The air flow assembly 1400 is held in place about the axial center of the oven 1300 on one end cap 1310. When configured as shown in FIG. 50, pressurized air flowing into the pneumatic port 1430 will be forced to flow substantially evenly through the holes 1320 in one end cap 1310, flow axially through the oven 1300 past the column bundle 310, and finally flow out of the oven 1300 through the holes 1320 in the second end cap 1310. The combination of the oven 1300 and the airflow assembly 1400 provides extremely efficient cooling of column bundle (not shown) because all the cooling air is forced to flow right around the column bundle (not shown). The cooling is also very quick because the air flow is substantially equal around column bundle (not shown) so the thermal equilibration time needed after cooling is dramatically reduced. When used to perform a negative temperature ramp, coolant from a cryogenic cooling source such as a tank of liquid nitrogen or nitrogen supplied from a refrigeration unit is supplies through the port 1430, cools the column and then exits from the holes 1320 in the plates 1310.

Figure 51:
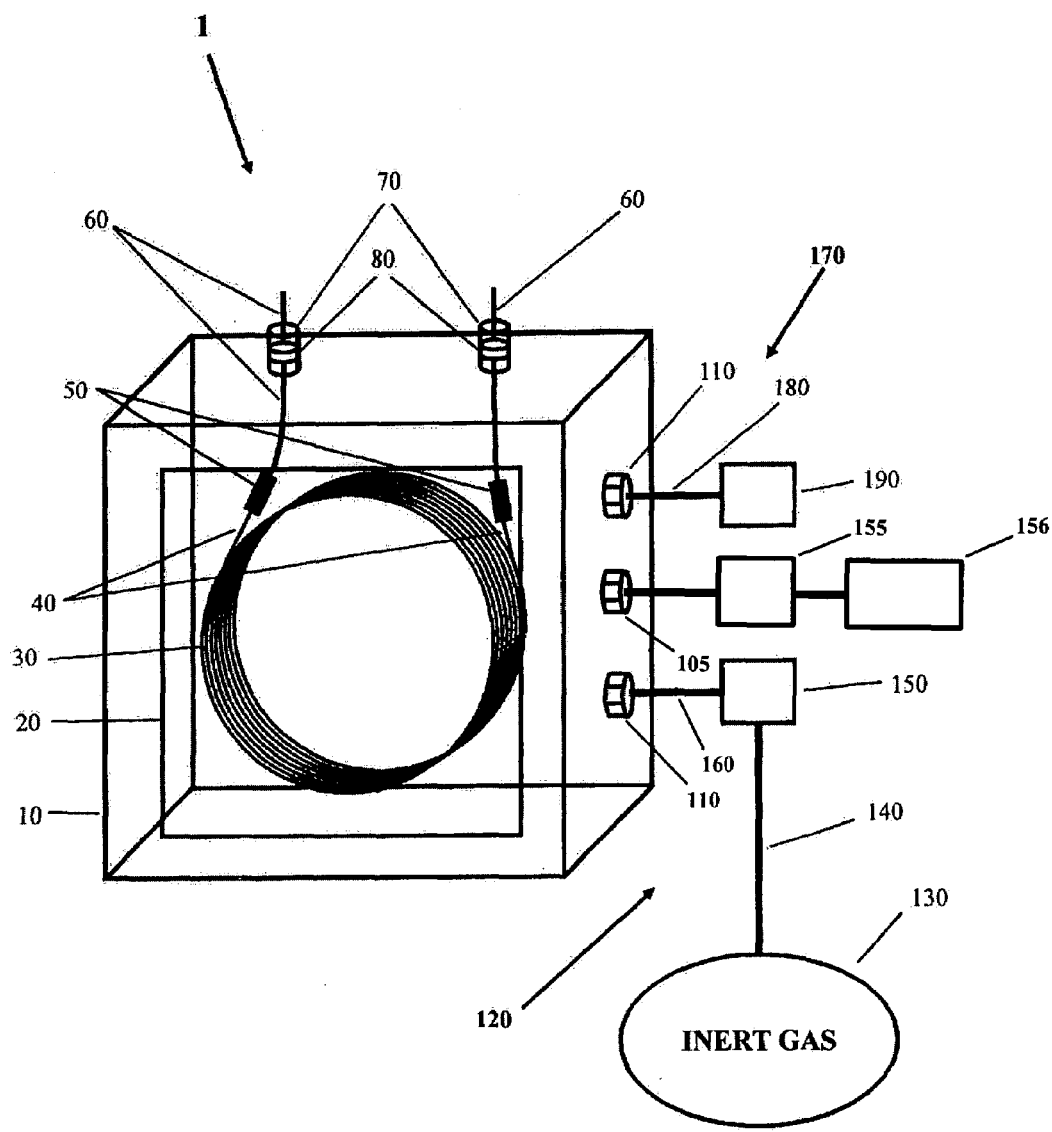
FIG. 51 shows a perspective view of a gas chromatograph column oven system constructed in accordance with the present invention in which a column is heated in an inert gas environment.

FIG. 51 shows GC column oven system 1 that maintains an inert gas within the oven enclosure 10 when it is heated. The oven enclosure 10 is any container that physically delimits an inner volume of space from the exterior of the container. The interior of the oven enclosure 10 is pneumatically sealed from the exterior so as to prevent the flow of gas from the exterior into the interior of the oven enclosure 10. The exact shape of the oven enclosure 10 and the manner in which it is sealed are not material to the invention described herein. The oven enclosure 10 contains at least one door or access port 20 through which a user can access the inside of the oven enclosure 10 for service or to install a column. When closed, the access port 20 is pneumatically sealed so that gas external to the oven enclosure 10 does not enter the oven enclosure 10 through the door nor through the gap between the edges of the access port 20 and the walls of the oven enclosure 10. The column 30 is contained within the oven enclosure 10.

Two sample line ports 70 are provided in the walls of the oven enclosure 10 through which sample line tubes carrying the chemical sample to be analyzed by the GC enter and exit the oven enclosure 10. The sample tubes may be the column ends 40 of column 30 or separate transfer lines 60. If transfer lines 60 are used as is shown in FIG. 51, the ends of the two transfer lines 60 within the oven enclosure 10 are pneumatically connected to the column ends 40 with column unions 50. The transfer lines 60, the column unions 50, and the column 30 comprise a single, pneumatically sealed sample tube through which chemical samples and carrier gas can flow freely from one end to the other without contaminating or being contaminated by the gaseous atmosphere within the oven enclosure 10. The sample line ports 70 include sample line seals 80 that substantially prevent the flow of external ambient air into the oven enclosure 10 through the sample line ports 70.

Two gas ports, inlet gas port 100 and outlet gas port 110, are provided in the walls of the oven enclosure 10 through which gas may flow into and out of the interior of the oven enclosure 10. Inlet gas port 100 is connected to inert gas supply 120 such that inert gas can flow into and fill the oven enclosure 10. Inert gas shall refer herein to any gas or gas mixture that is substantially free of oxygen such as nitrogen, carbon dioxide, helium, neon, or argon. The inert gas supply 120 shall comprise any combination of equipment that together supply inert gas at a pressure higher than that of the interior of the oven enclosure 10. The assembly 170 also includes a second inlet gas port 105 for supplying a coolant to the column 30. The second inlet gas port 105 is connected to a coolant controller 155 which is in turn connected to a coolant supply 156, such as a tank of liquid nitrogen. All of the controllers 150, 155 and 190 can be used under computer control to supply a desired amount of coolant at a desired flow rate and temperature so as to achieve a desired negative temperature ramp. Again, under many circumstance, the coolant flow rate at a given temperature is coupled with microwave heating all under computer control to achieve any desired negative temperature ramp or to hold the column at a given low temperature.

For example and as shown in FIG. 51, the inert gas supply 120 may comprise pressurized inert gas reservoir 130, flow line 140, the flow controller 150, and flow line 160 that are connected in series and through which inert gas flows. The inert gas reservoir 130 is any pressurized tank, bottle, or equivalent container of inert gas.

For the purposes of this invention, a flow controller shall be any device or combination of devices that can be used to measure, regulate, or control the flow of gas in a flow line including pressure sensors, valves, flow meters, and flow regulators. The gas outlet port 110 is connected to the gas exhaust system 170. The gas exhaust system 170 shall comprise any combination of equipment that together controls the flow of gas from the oven enclosure 10. For example and as shown in FIG. 51, the gas exhaust system 170 comprises the flow line 180 and the flow controller 190 that are connected in series and through which gas can flow from the oven enclosure 10 in a regulated manner.

When a column 30 is installed into the oven enclosure 10, the access port 20 must be opened resulting in oxygen contamination within the oven enclosure 10. To prevent unnecessary waste of inert gas while the access port 20 is open, flow controller 150 stops the flow of inert gas into oven enclosure 10. After the column 30 is installed and the access port 20 closed, oxygen in the oven enclosure 10 must be substantially removed prior to heating the column 30. Oxygen can be purged from the oven enclosure 10 by simultaneously opening the flow controllers 150 and 190 and allowing inert gas to freely flow through the oven enclosure 10 until the oxygen is substantially removed. Alternatively, the flow controllers 150 and 190 can be opened asynchronously. First, the first flow controller 150 is opened and the second flow controller 190 is closed which effectively pressurizes the oven enclosure 10. Inert gas mixes with the atmospheric gas contained therein. Second, the first flow controller 150 is closed and the second flow controller 190 is opened allowing the pressurized gas mixture to flow from the oven enclosure 10. By repeating this process, the oxygen in the oven enclosure 10 is rapidly diluted and effectively eliminated.

Inert gas can be used to speed up the cooling cycle after a heating cycle is completed. Opening the flow controllers 150 and 190 either synchronously or asynchronously during the cooling cycle allows cool inert gas from the inert gas supply 120 to flow through the oven enclosure 10 thereby accelerating the cooling rate of the column 30 contained therein. Alternatively, cool ambient air could be circulated through the oven enclosure 10 to cool it down. Using ambient air could reduce the volume of inert gas needed to operate the GC column oven systems taught herein that utilize accelerated cooling methods.

Once an inert gas environment is established within the oven enclosure 10, it can be maintained without contamination in one of two ways. First, the interior of the oven enclosure 10 can be completely sealed from its exterior so that no unwanted gas flows into or out of the oven enclosure 10. In practice, it may be difficult to achieve a perfect pneumatic seal. With an imperfect seal, oxygen could slowly leak into the oven enclosure 10 from the atmosphere and contaminate the inert gas environment contained therein. A second method for preventing oxygen contamination is to use the flow controller 150 in the inert gas supply 120 to maintain a positive pressure (with respect to the atmospheric pressure) of inert gas within the oven enclosure 10. Maintaining a positive pressure within oven enclosure 10 ensures that oxygen does not leak into the oven enclosure 10 even if there were small pneumatic leaks in the oven enclosure 10. The flow of gas would at all times be from the interior of the oven enclosure 10 to the exterior. For the purposes of this invention, the oven enclosure 10 shall be considered pneumatically sealed even if it contains small leaks provided that a) the leakage rate of oxygen into the oven is not large enough to substantially increase the degradation of the column 30 and/or b) the leakage rate of inert gas from a positively pressured oven enclosure 10 is not large enough to substantially increase the volume of inert gas required to maintain the inert gas environment within the oven enclosure 10.

During the heating cycle, the gas within the oven enclosure 10 will increase in temperature. If the oven enclosure 10 is pneumatically sealed, the pressure within the oven enclosure 10 could increase during the heating cycle. This pressure can be relieved using the flow controller 190 within the gas exhaust system 170. The flow controller 190 can release gas when the internal pressure of the oven enclosure 10 exceeds a threshold value, thus limiting the maximum potential pressure within the oven enclosure 10. If cooling gas is not circulated through the oven enclosure 10 during the cooling cycle to accelerate cooling, then the pressure within the oven enclosure 10 would similarly decrease as the temperature of the inert gas within the oven enclosure 10 decreases. This could result in a negative pressure (with respect to atmospheric pressure) forming within the oven enclosure 10 drawing oxygen into the oven. Using the flow controller 150 to maintain a positive pressure within the oven enclosure 10 prevents this potential oxygen ingress when the oven is cooling.

Heaters, fans, baffles, or other devices well known in the art may be added to the GC column oven system 1 to enable heating capabilities, to improve cooling rates, or to otherwise improve operating performance. However, such additional equipment is not an essential part of the invention taught herein and as such is not described. As should be clear to those skilled in the art, any such device can be added to the GC column oven system 1 provided that care is taken where appropriate to utilize pneumatic seals to substantially prevent oxygen ingress into the oven enclosure 10 while it or the column 30 is being heated.

Typical chromatographic columns are mounted on cylindrical fixtures that are 15 to 20 cm in diameter and up to 7 cm in height. An oven enclosure 10, like that shown in FIG. 51, built to accommodate such column fixtures would have an internal volume in excess of 5 liters. Such an oven enclosure requires substantial volumes of inert gas to purge oxygen from the enclosure after a column is installed or to cool down after a heating cycle is completed. A smaller oven enclosure reduces the volume of inert gas needed to purge the enclosure after a column change. A smaller oven enclosure also reduces the thermal mass of the system and thereby reduces the consumption of inert gas that would be needed to cool the system down. To make the oven enclosure smaller, the chromatographic column must be smaller.

Figure 52:
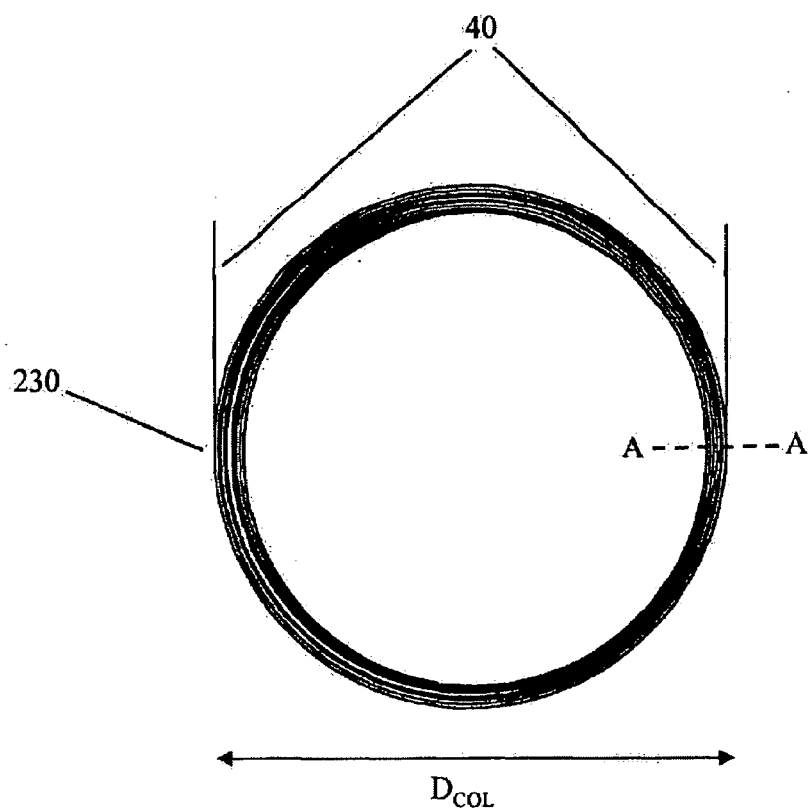
FIG. 52 shows a tightly wound chromatographic column bundle.
Figure 53:
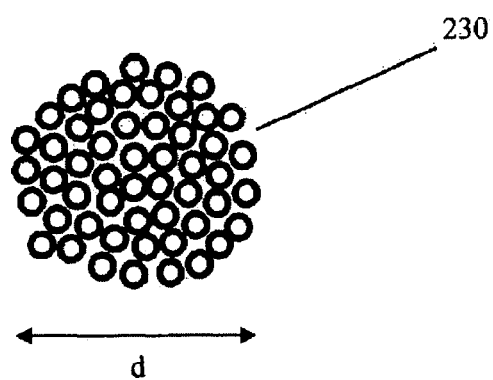
FIG. 53 shows the cross-section of a tightly wound column bundle.

FIG. 52 shows a column bundle 230 where a chromatographic column is wound tightly together to form a bundled coil and thereby minimize its physical size. FIG. 53 shows a view of the column bundle 230 across the section marked A—A in FIG. ('316) 2. A 30 m, 0.32 µm ID column coiled in the manner illustrated in FIG. 52 could have a major diameter '$D_{COL}$' of less than 8 cm and a cross sectional diameter 'd' of less than 6 mm. It shall be understood that the exact geometry of the column bundle 230 is not a critical aspect of this invention. Column bundle 230 shall refer to any chromatographic column packaged to achieve a small physical size.

Figure 54:
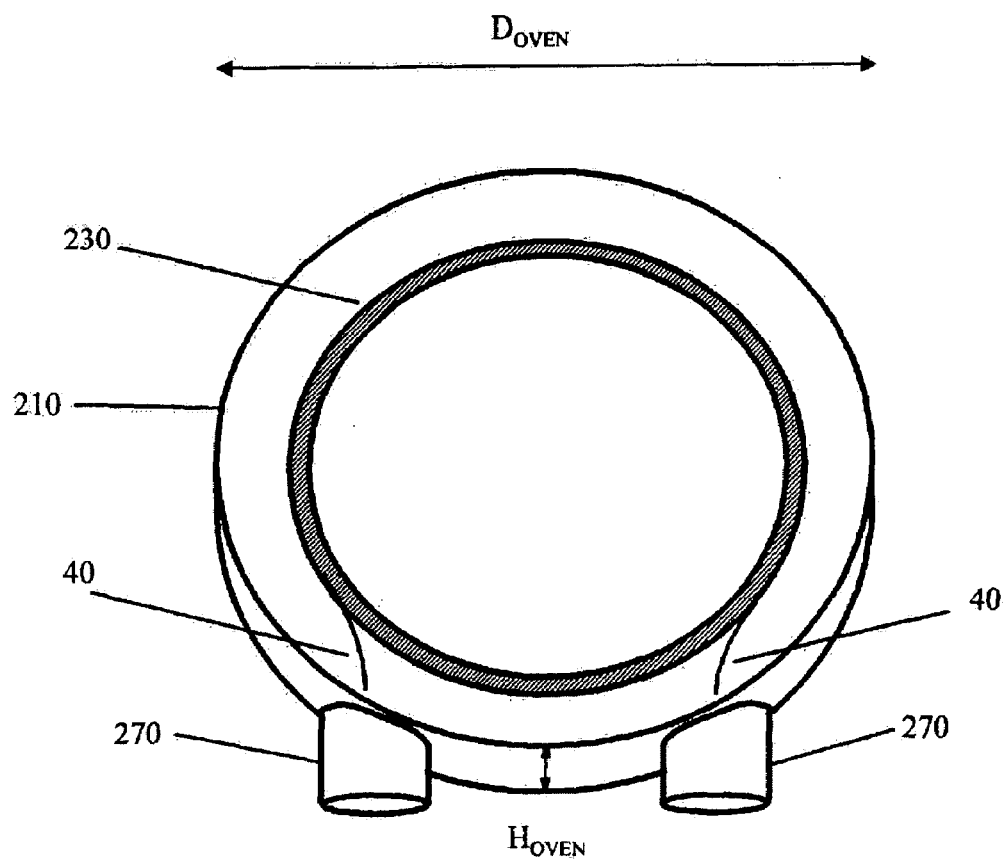
FIG. 54 shows a perspective view of an oven enclosure and a tightly wound column bundle.

FIG. 54 shows an oven enclosure 210 having a substantially annular cavity that can be used to contain and heat the column bundle 230. The oven enclosure 210 could have an internal diameter '$D_{OVEN}$' of less than 10 cm and an internal height '$H_{OVEN}$' of less than 1.5 cm resulting in an internal volume of less than 0.12 liters. The precise shape of the oven enclosure 210 is not an essential feature of this invention. The oven enclosure 210 can be any compact, pneumatically sealed enclosure designed to take advantage of the small size of the column bundle 230 contained therein and thereby reduce the volume of inert gas needed to operate the GC column oven system.

Figure 55:
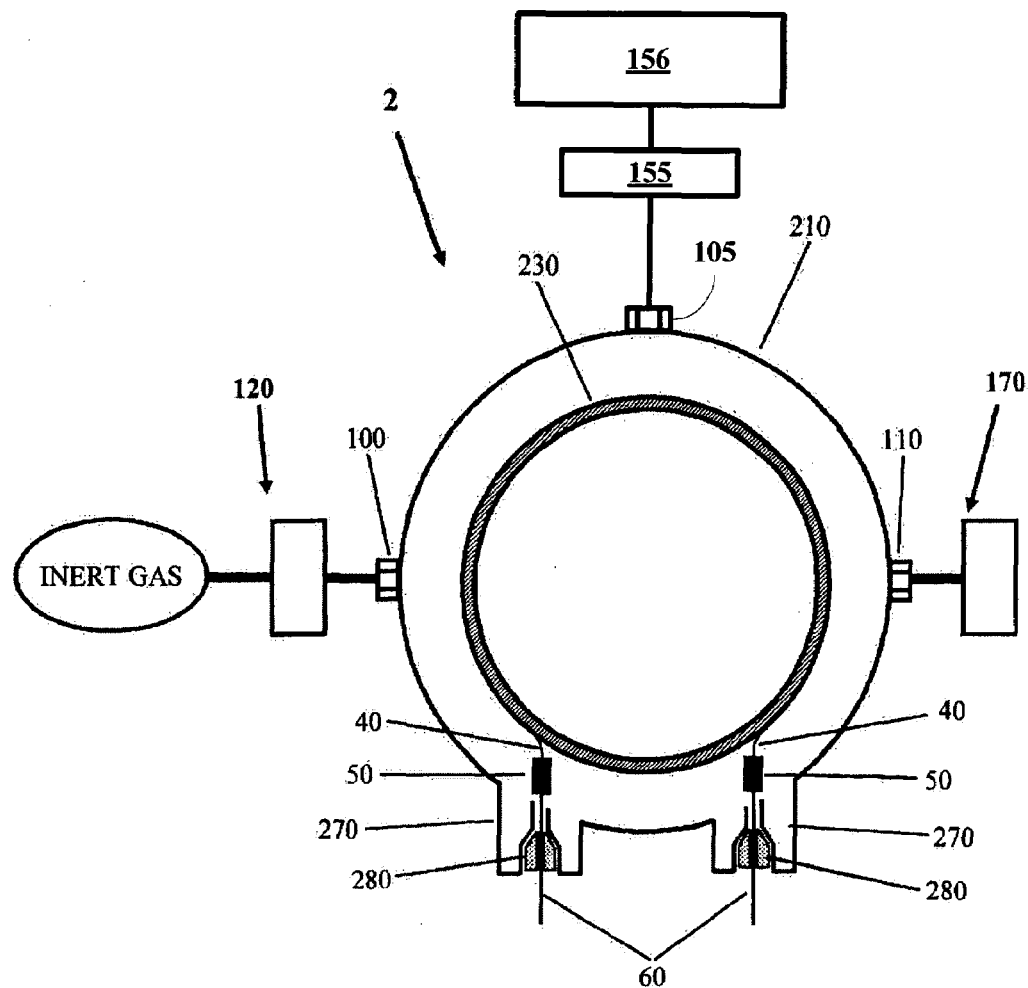
FIGS. 55 and 56 show two different cross sectional views of a gas chromatograph column oven system constructed in accordance with the present invention in which a tightly wound column bundle is heated in an inert gas environment.
Figure 56:
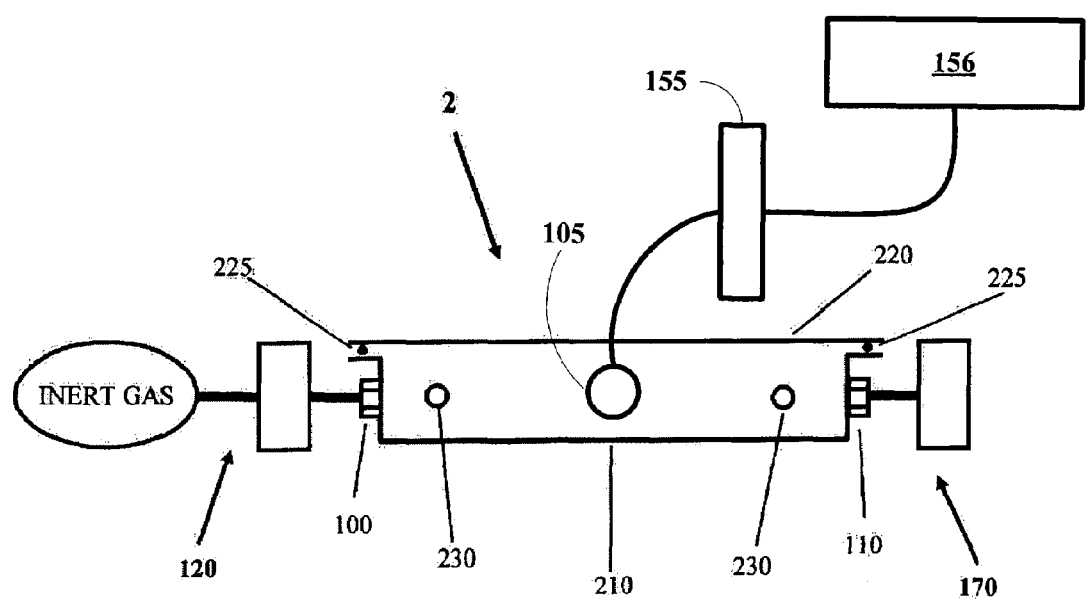

FIGS. 55 and 56 [FIGS. 5 and 6] are orthogonal, cross sectional views of a preferred embodiment of this invention. The GC column oven system 2 includes the oven enclosure 210 and the column bundle 230 as shown in FIG. ('316) 4. The oven enclosure 210 has an access port 220 that can be removed such that a user can access the inside of the oven enclosure 210 for service or to install the column bundle 230. The pressure seal 225, placed between the access port 220 and the oven enclosure 210, provides a pneumatic seal between the two. The pressure seal 225 can be any suitable sealing device such as an elastomeric o-ring. Again, the coolant supply assembly including port 105, controller 155 and coolant supply 156 are shown. By adjusting the flow rate of the coolant and the temperature of the coolant, a desired negative temperature ramp can be produced in the column to facilitate separation of lower boiling components from higher boiling components and/or to separate components having boiling points within a narrow temperature range. By using a cryogenic coolant such as liquid nitrogen or nitrogen gas formed from a controlled boiling of liquid nitrogen, subambient temperature end points can be achieved. Moreover, carefully controlling the rate of cooling can not only achieve a desired rate of cooling and the achievement of a desired low temperature endpoint, the controlled cooling can also be used to hold the column at a desired temperature, especially, a low temperature. Under certain conditions, both cooling and heating (microwave energy heating) must be used simultaneously, intermittently, periodically or under any combination of on/off periodic heating and/or cooling to achieve either a desired cooling or heating ramp or to achieve a desired hold, especially a hold at a subambient temperature. Such protocols that utilize negative temperature ramps to go below ambient temperature or the include a subambient temperature hold are ideally suited for separating low molecular weight components or components having similar boiling points—component that all boil in a narrow temperature range. Such temperature ranges are 50° C. or less, preferably, 25° C. or less, particularly, 10° C. or less, more particularly, 5° C. or less and especially, 2.5° C. or less.

Two sample line ports 270 are provided in the walls of the oven enclosure 210 through which sample lines can enter or exit through the wall of the oven enclosure 210. The sample line ports 270 contain sample line seals 280 that substantially prevent the flow of external ambient air into the oven enclosure 210 through the sample line ports 270. The sample line seals 280 can be any suitable sealing devices such as ferrules. As is shown in FIGS. 5 and 6, two transfer lines 60 enter oven enclosure 210 through the sample line ports 270 and the sample line seals 280. The transfer lines 60 are connected to the column ends 40 of the column bundle 230 with column unions 50 such that the combination comprises a single, pneumatically sealed sample tube through which chemical samples and carrier gas can flow freely from one end to the other without contaminating or being contaminated by the gaseous atmosphere within the oven enclosure 210.

Gas inlet port 100 and gas outlet port 110 are provided in the walls of the oven enclosure 210 and provide means through which gas can flow in and out of the oven enclosure 210. Inert gas supply 120 is connected to the gas inlet port 100 and supplies inert gas to the interior of the oven enclosure 210. Gas exhaust system 170 is connected to the gas outlet port 120 and controls the flow of gas out of the oven enclosure 210.

The effective thermal mass of the GC column oven system 2 can be further reduced if the thermal energy in the heating system is deposited directly in the column bundle 230 and not into the oven enclosure 210 because the column bundle 230 has much less thermal mass. If the oven enclosure 210 is also thermally isolated from the column bundle 230, it stays cool even when the column bundle 230 is hot. In such a configuration, the primary function of the oven enclosure 210 is to pneumatically isolate the column bundle 230 from oxygen and not to provide a means to heat the column bundle 230.

A chromatographic column can be directly heated in a variety of ways independently of the oven enclosure 210 and coiled into the column bundle 230 illustrated in FIGS. 52 and 53. The column could be heated by a resistively heated wire that is coiled up together with the column in the column bundle 230 shown in FIG. 52. The column could be enclosed within a metal sheath that resistively heats the column. The column/metal sheath can be coiled tightly in the manner illustrated in FIG. 52. The column could have microwave absorber embedded into it so that it could be directly heated by microwave energy. Many methods known to those skilled in the art can be used to directly heat a chromatographic column substantially independently of the column oven enclosure.

The exact method by which a column is heated is not a critical aspect of the invention taught herein. For the purposes of this invention, it shall be understood that the oven enclosure 210 shall refer to any physical enclosure used to pneumatically isolate the column bundle 230 from the atmosphere exterior to the oven enclosure 210. The oven enclosure 210 may or may not be part of the systems used to heat the column bundle 230. It shall also be understood that the column bundle 230 shall refer to any tightly bundled column or column/heater combination designed to achieve small size. The column bundle 230 may include direct heating means such as microwave absorbers or resistively heated wires or sheaths without deviating from the teaching of this patent.

When direct column heating means are utilized, the column bundle 230 can be passively cooled as quickly as a column can be cooled using active, convective cooling in conventional GC column ovens. Direct dissipation to the environment is fast enough to shed the minimal thermal energy in the column bundle 230. Even faster cooling rates can be achieved with small volumes of inert gas flowing into the oven enclosure 210 during cooling cycles. Thus, the GC column oven system 2 can significantly enhance the maximum operating temperature and lifetime of the column without sacrificing cooling rates using only modest volumes of inert gas.

All references cited herein are incorporated herein by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for improving separation efficiencies comprising the step of:
    providing a gas chromatography (GC) apparatus comprising:
        a microwave oven adapted to heat the GC column and including:
            a GC column having:
                a continuous phase material forming a wall surrounding an interior space for containing a chromatography sample and
                a microwave absorbing material contained in the continuous phase material,
            a microwave source,
            a temperature sensor,
            a microwave source controller adapted to control a microwave power to the microwave oven by the microwave source and to control a power efficiency of the microwave source,
            a coolant source, and
            a coolant source controller adapted to control a flow rate of the coolant, and
    performing one or a first plurality of positive temperature ramps, where each positive temperature ramp comprises raising a current temperature of the GC column from a lower start temperature or a first plurality of lower start temperatures to a higher stop temperature or a first plurality of higher stop temperatures at a positive controlled rate or at a first plurality of controlled rates, and
    performing one or a second plurality of negative temperature ramps, where each negative temperature ramp comprises lowering a current temperature of the GC column from a higher start temperature or a second plurality of higher start temperatures to a lower stop temperature or a second plurality of lower stop temperatures at a negative controlled rate or at a second plurality of controlled rates,
    where the negative temperature ramp improves the separation of lower boiling components from higher boiling components or the improve the separation of components having boiling points within a narrow temperature range.

2. The method claim 1, wherein an order of the positive ramps and the negative ramps are designed to achieve a desired separation efficiency.

3. The method of claim 1, farther comprising the steps of:
    holding the GC column at each higher stop temperature for a positive ramp hold time and at each lower stop temperature for a negative ramp hold time by supplying a coolant to the GC column and irradiating the GC column with microwave energy under temperature maintaining conditions.

4. The method of claim 3, wherein the under temperature maintaining conditions comprises a coolant flow rate at a given coolant temperature coupled with microwave heating under computer control to maintain the GC column at each bold temperature.

5. The method of claim 1, wherein at least one lower stop temperature is a subambient temperature.

6. The method of claim 1, wherein the coolant is nitrogen and the coolant supply is a liquid nitrogen tank.

7. The method of claim 1, wherein the narrow temperature range is 10° C. or less, each hold time is from about 0 minutes to about 30 minutes, and each positive or negative temperature ramp comprises a heating rate or cooling rate between about 1° C./minutes and about 300° C./minute.

8. The method of claim 1, wherein the narrow temperature range is 10° C. or less, cacti hold time is from about 0.1 minutes to about 20 minutes, and each positive or negative temperature ramp comprises a heating rate or cooling rate between about 1° C./minutes and about 20° C./minute.

9. The method of claim 1, wherein the narrow temperature range is 10° C. or less, each hold time is from about 0.5 minutes to about 10 minutes, and each positive or negative temperature ramp comprises a heating rate or cooling rate between about 1° C./minutes and about 150° C./minute.

* * * * *